US008865629B2

(12) United States Patent
Sohn et al.

(10) Patent No.: US 8,865,629 B2
(45) Date of Patent: *Oct. 21, 2014

(54) LIBRARY OF TRANSLATIONAL FUSION PARTNERS FOR PRODUCING RECOMBINANT PROTEINS AND TRANSLATIONAL FUSION PARTNERS SCREENED THEREFROM

(75) Inventors: Jung-Hoon Sohn, Daejeon (KR);
Eui-Sung Choi, Daejeon (KR);
Jung-Hoon Bae, Daejeon (KR);
Mi-Kyung Shin, Daejeon (KR);
Sung-Sook Yoon, Daejeon (KR);
Chang-Soo Chun, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 1524 days.

This patent is subject to a terminal disclaimer.

(21) Appl. No.: 11/914,437

(22) PCT Filed: Jul. 13, 2006

(86) PCT No.: PCT/IB2006/003102
§ 371 (c)(1),
(2), (4) Date: Dec. 8, 2008

(87) PCT Pub. No.: WO2007/015178
PCT Pub. Date: Feb. 8, 2007

(65) Prior Publication Data
US 2009/0181425 A1 Jul. 16, 2009

(30) Foreign Application Priority Data
Jul. 15, 2005 (KR) .......................... 10-2005-0064402

(51) Int. Cl.
| C40B 20/04 | (2006.01) |
| C40B 30/06 | (2006.01) |
| C40B 50/06 | (2006.01) |
| C12P 21/02 | (2006.01) |
| C12N 15/81 | (2006.01) |
| C07K 14/39 | (2006.01) |
| C12N 15/10 | (2006.01) |

(52) U.S. Cl.
CPC ............... *C12P 21/02* (2013.01); *C12N 15/81* (2013.01); *C07K 14/39* (2013.01); *C12N 15/1086* (2013.01)
USPC ................................... 506/4; 506/10; 506/26

(58) Field of Classification Search
USPC ................................................. 506/4, 10, 26
See application file for complete search history.

(56) References Cited

U.S. PATENT DOCUMENTS

| 5,037,760 A | 8/1991 | Smith et al. |
| 5,536,637 A * | 7/1996 | Jacobs .......................... 435/6.17 |
| 5,952,171 A | 9/1999 | McCarthy et al. |
| 6,136,569 A * | 10/2000 | Baker et al. ................ 435/91.41 |
| 6,150,098 A | 11/2000 | Zhang et al. |
| 6,228,590 B1 | 5/2001 | Baker |
| 6,548,633 B1 | 4/2003 | Edwards et al. |
| 7,029,842 B2 | 4/2006 | Duffner et al. |
| 2002/0127557 A1 | 9/2002 | Tan et al. |
| 2004/0110939 A1 | 6/2004 | Edwards et al. |
| 2007/0275385 A1 | 11/2007 | Sohn et al. |

FOREIGN PATENT DOCUMENTS

| CN | 001468317 A | 1/2004 | |
| EP | 1 170 366 A1 | 1/2002 | |
| WO | WO 97/40146 A1 | 10/1997 | |
| WO | WO 99/49028 * | 9/1999 | ............. C12N 15/10 |
| WO | WO 99/49028 A1 | 9/1999 | |
| WO | WO 01/00806 A2 | 1/2001 | |
| WO | WO 01/77315 A1 | 10/2001 | |
| WO | WO 02/072821 A2 | 9/2002 | |
| WO | WO 2007/015178 A2 | 2/2007 | |

OTHER PUBLICATIONS

Baldari, C., et al., "Differential stability of human interleukin 1 beta fragments expressed in yeast," Protein Eng. 1:433-437, JRL Press Limited (1987).
Broekhuijsen, M.P., et al., "Secretion of heterologous proteins by *Aspergillus niger*: Production of active human interleukin-6 in a protease-deficient mutant by KEX2-like processing of a glucoamylase-hIL6 fusion protein," *J Biotechnol.* 31:135-145, Elsevier Science Publishers B.V. (Nov. 1993).
Contreras, R., et al., "Efficient KEX2-like Processing of a Glucoamylase-Interleukin-6 Fusion Protein by *Aspergillus nidulans* and Secretion of Mature Interleukin-6," *Bio/Technology* (N.Y.) 9:378-381, Nature Pub. Co. (Apr. 1991).
Crosier, P.S., et al., "In Situ Hybridization Screen in Zebrafish for the Selection of Genes Encoding Secreted Proteins," *Developmental Dynamics* 222:637-644, Wiley-Liss, Inc. (2001).
Dorner, A.J., et al., "Overexpression of GRP78 mitigates stress induction of glucose regulated proteins and blocks secretion of selective proteins in Chinese hamster ovary cells," *The EMBO Journal* 11:1563-1571, Oxford University Press (1992).
Dorner, A.J., et al., "Reduction of Endogenous GRP78 Levels Improves Secretion of a Heterologous Protein in CHO Cells," *Molecular and Cellular Biology* 8:4063-4070, American Society for Microbiology (1988).
Downing, K.J., et al., *Staphylococcus aureus* nuclease is a useful secretion reporter for mycobacteria, *Gene* 239:293-299, Elscience Science B.V. (1999).
Eckart, M.R. and Bussineau, C.M., "Quality and authenticity of heterologous proteins synthesized in yeast," *Curr Opin Biotechnol.* 7:525-530, Current Biology Ltd. (Oct. 1996).
Ferguson, D.A., et al., "Selective Identification of Secreted and Transmembrane Breast Cancer Markers using *Escherichia coli* Ampicillin Secretion Trap," *Cancer Res* 65:8209-8217, American Association for Cancer Research (2005).
Nplio Galliciotti, G., et al., "Signal-sequence Trap in Mammalian and Yeast Cells: A Comparison," *J. Membrane Biol.* 183:175-182, Springer-Verlag (2001).

(Continued)

Primary Examiner — Amber D Steele
(74) Attorney, Agent, or Firm — Sterne, Kessler, Goldstein & Fox P.L.L.C.

(57) ABSTRACT

The invention relates to techniques for the rapid screening of suitable translational fusion partners (TFPs) capable of inducing secretory production of recombinant proteins, especially proteins that are difficult to produce using conventional recombinant production methods.

30 Claims, 30 Drawing Sheets

(56) References Cited

OTHER PUBLICATIONS

Goo, J.H., et al., "Selection of *Arabidopsis* genes encoding secreted and plasma membrane proteins," *Plant Molecular Biology* 41:415-423, Kluwer Academic Publishers (1999).

Gouka, R.J., et al., "Efficient production of secreted proteins by *Aspergillus*: progress, limitations and prospects," *Appl Microbiol Biotechnol*. 47:1-11, Springer-Verlag (Jan. 1997).

Harmsen, M.M., et al., "Overexpression of binding protein and disruption of the *PMR1* gene synergistically stimulate secretion of bovine prochymosin but not plant Thaumatin in yeast," *Appl Microbiol Biotechnol*. 46:365-370, (Nov. 1996).

Hayano, T., et al., "Protein disulfide isomerase mutant lacking its isomerase activity accelerates protein folding in the cell," *FEBS Lett*. 377:505-511, Federation of European Biochemical Societies (Dec. 1995).

Hsu, T.-A., et al., "Effects of Co-expressing Chaperone BiP on Functional Antibody Production in the Baculovirus System," *Protein Expr Purif*. 5:595-603, Academic press, Inc. (Dec. 1994).

Jacobs, K.A., et al., "A genetic selection for isolating cDNAs encoding secreted proteins," *Gene* 198:289-296, Elsevier Science B.V. (1997).

Jeenes, D.J., et al., "A truncated glucoamylase gene fusion for heterologous protein secretion from *Aspergillus niger*," *FEMS Microbiol Lett*. 107:267-272, Federation of European Microbiological Societies (Mar. 1993).

Kjeldsen, T., et al., "Prepro-Leaders Lacking N-linked Glycosylation for Secretory Expression in the Yeast *Saccharomyces cerevisiae*," *Protein Expr Purif*: 14:309-316, Academic Press (Dec. 1998).

Kjeldsen, T., et al., "Synthetic Leaders with Potential BiP Binding Mediate High-Yield Secretion of Correctly Folded Insulin Precursors from *Saccharomyces cerevisiae*," *Protein Expr Purif*. 9:331-336, Academic Press (Apr. 1997).

Klein, R.D., et al., "Selection for genes encoding secreted proteins and receptors," *Proc. Natl. Acad. Sci. USA* 93:7108-7113, National Academy of Sciences (Jul. 1996).

Lee, J., et al., "Novel Secretion System of a Recombinant *Saccharomyces cerevisiae* Using an N-terminus Residue of Human IL-1β as Secretion Enhancer," *Biotechnol. Prog*. 15:884-890, American Chemical Society and American Institute of Chemical Engineers (1999).

Lim, E.M., et al., "Identification of *Mycobacterium tuberculosis* DNA Sequences Encoding Exported Proteins by Using *phoA* Gene Fusions," *J. Bacteriol*. 177:59-65, American Society for Microbiology (Jan. 1995).

MacConaill, L.E., et al., Investigation of Protein Export in *Bifidobacterium breve* UCC2003, *Appl. Environ. Microbiol*. 69:6994-7001, American Society for Microbiology (Dec. 2003).

Makrides, S.C., "Strategies for Achieving High-Level Expression of Genes in *Escherichia coli*," Microbiological Reviews 60:512-538, American Society for Microbiology (1996).

Monteoliva, L., et al., "Large-Scale Identification of Putative Exported Proteins in *Candida albicans* by Genetic Selection," *Eukaryotic Cell* 1:514-525, American Society for Microbiology (Aug. 2002).

Muesch, A., et al., "A novel pathway for secretory proteins?" *TIBS* 15:86-88, Elsevier Science Publishers Ltd. (UK)(Mar. 1990).

Roberts, I.N., et al., "Heterologous gene expression in *Aspergillus niger*: a glucoamylase-porcine pancreatic prophospholipase $A_2$ fusion protein is secreted and processed to yield mature enzyme," *Gene* 122:155-161, Elsevier Science Publishers B.V. (Dec. 1992).

Robinson, A.S., et al., "Protein Disulfide Isomerase Overexpression Increases Secretion of Foreign Proteins in *Saccharomyces cerevisiae*," *Bio/Technology* (NY) 12:381-384, Nature Pub. Co. (Apr. 1994).

Robinson, A.S., et al., "Reduction of BiP Levels Decreases Heterologous Protein Secretion in *Saccharomyces cerevisiae*," *J. Biol. Chem*. 271:10017-10022, American Society for Biochemistry and Molecular Biology (1996).

Sagt, C.M.J., et al., "Introduction of an N-Glycosylation Site Increases Secretion of Heterologous Proteins in Yeasts," *Applied and Environmental Microbiology* 66:4940-4944, American Society for Microbiology (2000).

Schultz, L.D., et al., "Using Molecular Genetics to Improve the Production of Recombinant Proteins by the Yeast *Saccharomyces cerevisiae*," *Ann NY Acad Sci*. 721:148-157, New York Academy of Sciences (May 1994).

Surpili, M.J., et al., "A yeast-based model system for cloning secreted and membrane proteins," *An Acad Bras Cienc* 74:599-608, Academia Brasileira De Ciencias (2002).

Takahashi, S., et al., "Function of the prosequence for in vivo folding and secretion of active *Rhizopus oryzae* lipase in *Saccharomyces cerevisiae*," *Appl Microbiol Biotechnol*. 55:454-462, Springer Verlag (May 2001).

Tan, N.S., et al., "Engineering a novel secretion signal for cross-host recombinant protein expression," *Protein Eng*. 15:337-345, Oxford University Press (2002).

Wang, H. and Ward, M., "Molecular characterization of a PDI-related gene *prpA* in *Aspergillus niger* var. *awamori*," *Curr Genet* 37:57-64, Springer-Verlag (Jan. 2000).

Ward, P.P., et al., "A system for production of commercial quantities of human lactoferrin: a broad spectrum natural antibiotic," *Bio/Technology* (NY). 13:498-503, (May 1995).

Ward, M., et al., "Improved Production of Chymosin in *Aspergillus* by Expression as a Glucoamylase-Chymosin Fusion," *Bio/Technology* 8:435-440, Nature Pub. Co. (1990).

NPL38 International Search Report for International Appl. No. PCT/KR2004/003517, Korean Intellectual Property Office, mailed Apr. 7, 2005.

International Search Report for International Appl. No. PCT/IB2006/003102, Korean Intellectual Property Office, mailed Mar. 30, 2003.

Abécassis, V. et al., "High efficiency family shuffling based on multistep PCR and in vivo DNA recombination in yeast: statistical and functional analysis of a combinatorial library between human cytochrome P450 1A1 and 1A2," *Nucleic Acids Research* 28 (20 e88):1-10, Oxford University Press, England (2000).

Juge, N., et al., "Comparison of barley malt α-amylase 1 and 2: construction of cDNA hybrids by in vivo recombination and their expression in yeast," *Gene* 130:159-166, Elsevier Science Publishers N.V., Netherlands (1993).

Oldenburg, K.R., et al., "Recombination-mediated PCR-directed pplasmid construction in vivo in yeast," *Nucleic Acids Research* 25(2):451-452, Oxford University Press, England (1997).

\* cited by examiner (A)   (B)

A

B

LIBRARY OF TRANSLATIONAL FUSION
PARTNERS FOR PRODUCING
RECOMBINANT PROTEINS AND
TRANSLATIONAL FUSION PARTNERS
SCREENED THEREFROM

BACKGROUND OF THE INVENTION

1. Field of the Invention

This invention is in the field of recombinant protein expression. In particular, the invention relates to techniques for the rapid screening of suitable translational fusion partners (TFPs) capable of inducing secretory production of recombinant proteins, especially proteins that are difficult to produce using conventional recombinant production methods.

2. Related Art

The recombinant expression of proteins of interest is a widely used; procedure to produce large quantities of proteins for research purposes or for therapeutic and other commercial uses. A variety of recombinant expression systems are known in the art, including bacterial, yeast, and mammalian host cell systems, and many different proteins have been successfully produced in these systems. However, there are also many proteins that are not easily produced using available expression systems, resulting in little or no protein expression and secretion. Methods for improving the secretion of recombinantly expressed proteins, such as overexpressing secretory factors in the host cells, using fusion proteins comprising the protein of interest fused to a well-secreted protein, and adding synthetic linker sequences, have had some success with particular proteins of interest. However, no general technique has been identified that is effective for the secretory production of all proteins.

In an effort to identify secreted proteins and novel signal sequences, several signal sequence trap systems have been developed. U.S. Pat. No. 6,228,590 describes a technique for screening for mammalian signal sequences by transforming reporter protein-deficient yeast with nucleic acids comprising mammalian coding sequences fused to a reporter protein and detecting cells that secrete the reporter protein. A similar system using invertase-deficient yeast and an invertase reporter protein is disclosed in EP0907727. Yeast-based signal sequence traps have been used to identify secreted proteins from human DNA Klein et al., *Proc. Natl. Acad. Sci. USA* 93:7108 (1996); Jacobs et al., *Gene* 198:289 (1997)), mouse DNA (Gallicioti et al., *J. Membrane Biol.* 183:175 (2001)), zebrafish DNA (Crosier et al, *Dev. Dynamics* 222: 637 (2001)), *Arabidopsis* DNA (Goo et al., *Plant Mol. Biol.* 41:415 (1999)), potato DNA (Surpili et al., *Anais de Academia Brasileira de Ciencias* 74:599 (2002)), and *Candida albicans* DNA (Monteoliva et al., *Eukaiyotic Cell* 1:514 (2002)). Similar trap systems have been developed using mammalian host cells (Gallicioti et al., *J. Membrane Biol.* 183:175 (2001)) and bacterial host cells (Ferguson et al., *Cancer Res.* 65:8209 (2000). Reporter proteins that have been used in signal sequence traps include invertase (Klein et al., *Proc. Natl. Acad. Sci. USA* 93:7108 (1996)), alpha amylase (U.S. Pat. No. 6,228,590), acid phosphatase (PHQ5) (Surpili et al., *Anais de Academia Brasileira de Ciencias* 74:599 (2002)), and β-lactamase Ferguson et al., *Cancer Res.* 65:8209 (2000).

A method for identifying translational fusion partners (TFPs) useful for secretion of a target protein is disclosed in WO 2005/068658. The method comprises (i) obtaining a plurality of host cells transformed with a variety of vectors comprising a library of nucleic acid fragments and a target protein-encoding nucleotide sequence fused with a reporter protein-encoding nucleotide sequence, wherein the host cells are deficient in the reporter protein, and (ii) identifying a TFP library from the host cells, wherein the TFP library comprises nucleic acid fragments which individually induce the secretion of the target protein.

SUMMARY OF THE INVENTION

The present invention relates to a rapid and efficient automatic screening method for the identification of TFPs that are effective for inducing secretion of a target protein. The invention allows any target protein to be secreted from a host cell, including target proteins that are not expressed or expressed only at low levels using traditional recombinant expression systems.

In one embodiment, the invention relates to a method of identifying a target protein specific TFP, said method comprising:

(i) co-transforming a plurality of reporter protein deficient host cells with a plurality of linear vectors and a nucleotide sequence encoding a target protein to produce a plurality of transformed host cells, wherein each of said linear vectors comprises a nucleic acid fragment from a library of nucleic acid fragments and a nucleotide sequence encoding a N-terminal amino acid-deleted reporter protein, and wherein said nucleotide sequence encoding a target protein comprises, at the 3' end, a nucleotide sequence encoding the N-terminal amino acids deleted from said reporter protein in said linear vector, and at the 5' end, a linker DNA;

(ii) incubating said plurality of transformed host cells under conditions effective to allow in vivo recombination of said linear vectors and said nucleotide sequence encoding a target protein;

(iii) identifying a cell showing an activity of the reporter protein from the plurality of transformed host cells of (ii); and (iv) identifying a TFP from the cell identified in (iii);

wherein said TFP comprises a nucleic acid fragment which induces the secretion of said target protein.

Another embodiment of the invention relates to a method of identifying a target protein specific TFP library, said method comprising:

(i) co-transforming a plurality of reporter protein deficient host cells with a plurality of linear vectors and a nucleotide sequence encoding a target protein to produce a plurality of transformed host cells, wherein each of said linear vectors comprises a nucleic acid fragment from a library of nucleic acid fragments and a nucleotide sequence encoding a N-terminal amino acid-deleted reporter protein, and wherein said nucleotide sequence encoding a target protein comprises, at the 3' end, a nucleotide sequence encoding the N-terminal amino acids deleted from said reporter protein in said linear vector, and at the 5' end, a linker DNA;

(ii) incubating said plurality of transformed host cells under conditions effective to allow in vivo recombination of said linear vectors and said nucleotide sequence encoding a target protein;

(iii) identifying cells showing an activity of the reporter protein from the plurality of transformed host cells of (ii); and (iv) identifying a TFP library from the cells identified in (iii);

wherein said TFP library comprises nucleic acid fragments which individually induce the secretion of said target protein.

The invention further relates to a TFP or a library of TFPs identified by the methods of the invention.

The invention further comprises a nucleic acid fragment encoding a TFP or a library of nucleic acid fragments encoding TFPs.

The invention also includes a nucleic acid comprising a nucleotide sequence encoding a TFP and a nucleotide sequence encoding a target protein.

The invention further relates to a method of producing a target protein using a TFP of the invention.

The invention additionally relates to a linear vector comprising a nucleic acid fragment from a library of nucleic acid fragments and a nucleotide sequence encoding a N-terminal amino acid-deleted reporter protein.

The invention also comprises a plurality of reporter protein-deficient host cells transformed with the library of linear vectors and a nucleotide sequence encoding a target protein of the invention.

BRIEF DESCRIPTION OF THE
DRAWINGS/FIGURES

The above and other objects, features and advantages of the present invention will be more clearly understood from the following detailed description taken in conjunction with the accompanying drawings.

FIG. 1 shows a process for deleting the invertase gene and a pop-out process of a selectable marker.

FIG. 2 shows zymogram analysis for invertase activity (lanes 1, 2 and 3: wild-type *Saccharomyces cerevisiae* Y2805; and lanes 4, 5 and 6: invertase-deficient strain (*S. cerevisiae* Y2805Δsuc2).

FIG. 3 photographically shows the growth of yeast cells according to carbon sources (SUC2: wild-type *S. cerevisiae* Y2805; and Δsuc2: invertase-deficient strain (*S. cerevisiae* Y2805Δsuc2).

FIG. 4 shows the results of Southern blotting for the deletion of the invertase gene (lanes 1 and 2: *S. cerevisiae* Y2805 (ura3 SUC2); lanes 3 and 4: *S. cerevisiae* Y2805Δsuc2U (URA3Δsuc2); and lanes 5 and 6: *S. cerevisiae* Y2805Δsuc2 (ura3Δsuc2).

FIG. 5 photographically shows the growth of yeast cells containing plasmids pYGAP-SNS-SUC2, pYGAP-HSA-SUC2, and pYGAP-hIL2-SUC2, on glucose and sucrose media, respectively.

Figure 18:
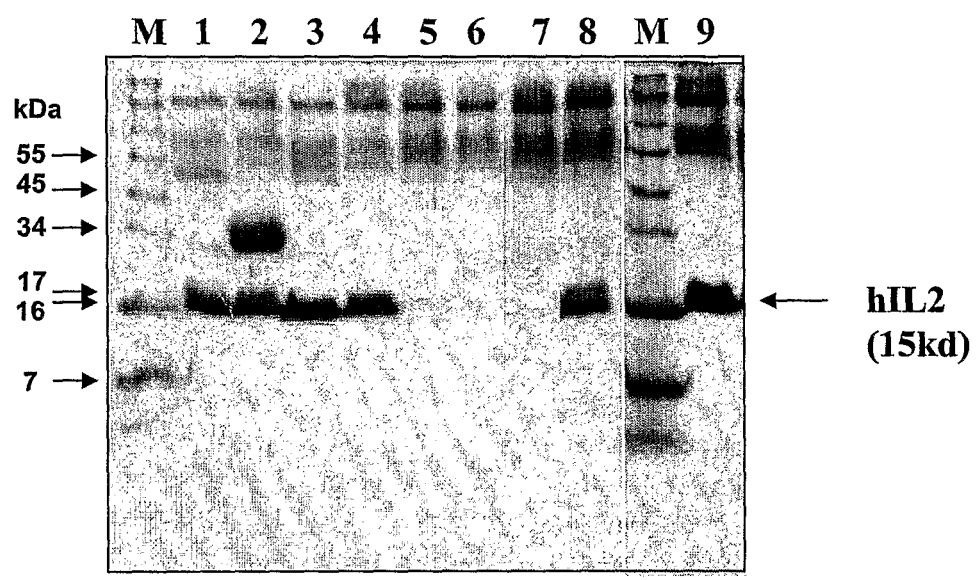

FIG. 18 shows the results of SDS-PAGE of culture supernatants of yeast cells secreting human IL2 (lane M: protein size marker; lane 1: culture supernatant of yeast cells containing pYIL-KRT1-4 (WO 2005/068658) as a control for IL2 secretion; lane 2: culture supernatant of yeast cells containing pYGT9-IL2; lane 3: culture supernatant of yeast cells containing pYGT21-IL2; lane 4: culture supernatant of yeast cells containing pYGT13-IL2; lane 5: culture supernatant of yeast cells containing pYGT17-IL2; lane 6: culture supernatant of yeast cells containing pYGT25-IL2; lane 7: culture supernatant of yeast cells containing pYGT19-IL2; lane 8: culture supernatant of yeast cells containing pYGT18-IL2; lane 9: culture supernatant of yeast cells containing pYGT27-IL2).

Figure 19:
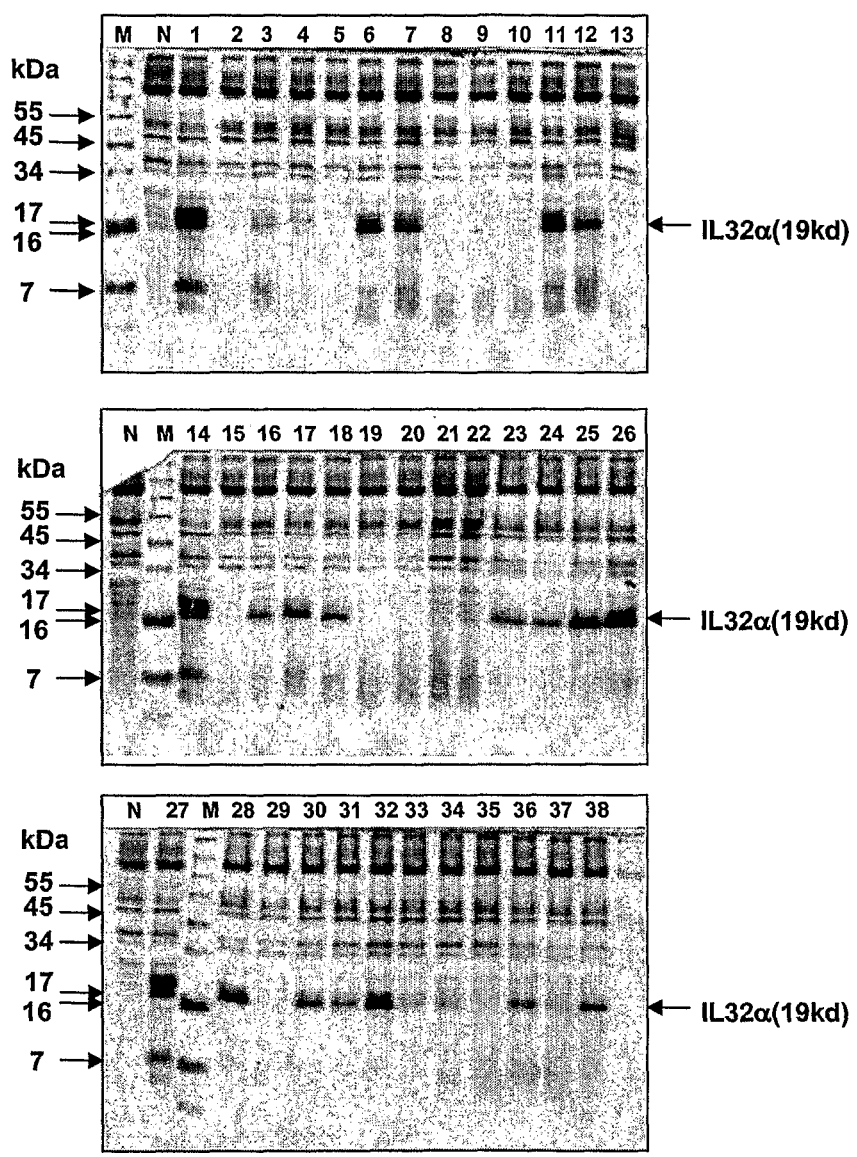

FIG. 19 shows the result of SDS-PAGE of culture supernatants of 38 yeast transformants obtained from the TFP selection process for human IL32α (lane M: protein size marker; lane N: untransformed cell as a negative control; lane 1 to 38: yeast transformants).

Figure 20:
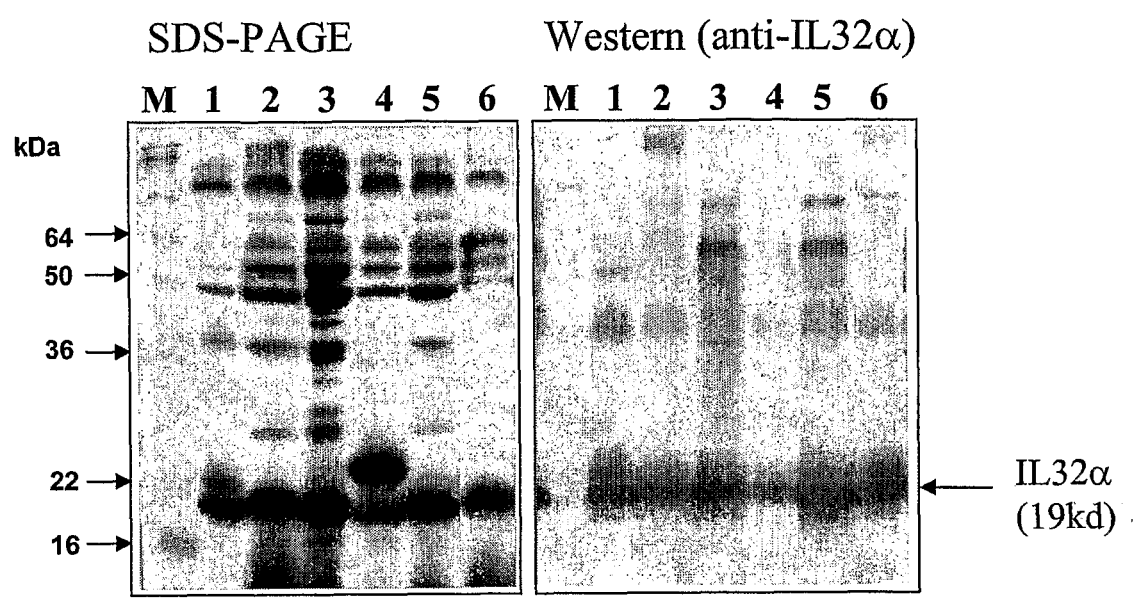

FIG. 20 shows the results of $DS-PAGE and Western blotting of culture supernatants of yeast cells secreting human IL32α (lane M: protein size marker; lane 1: culture supernatant of yeast cells containing pYGT3-IL32α; lane 2: culture supernatant of yeast cells containing pYGT21-IL32α; lane 3: culture supernatant of yeast cells containing pYGT13-IL32α; lane 4: culture supernatant of yeast cells containing pYGT25-IL32α; lane 5: culture supernatant of yeast cells containing pYGT22-IL32α and lane 6: culture supernatant of yeast cells containing pYGT11-IL32α).

Figure 21:
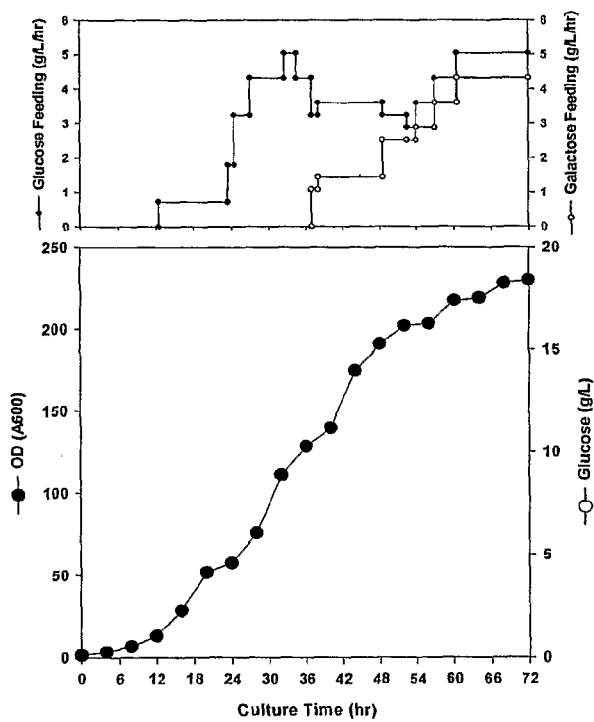
Figure 21:
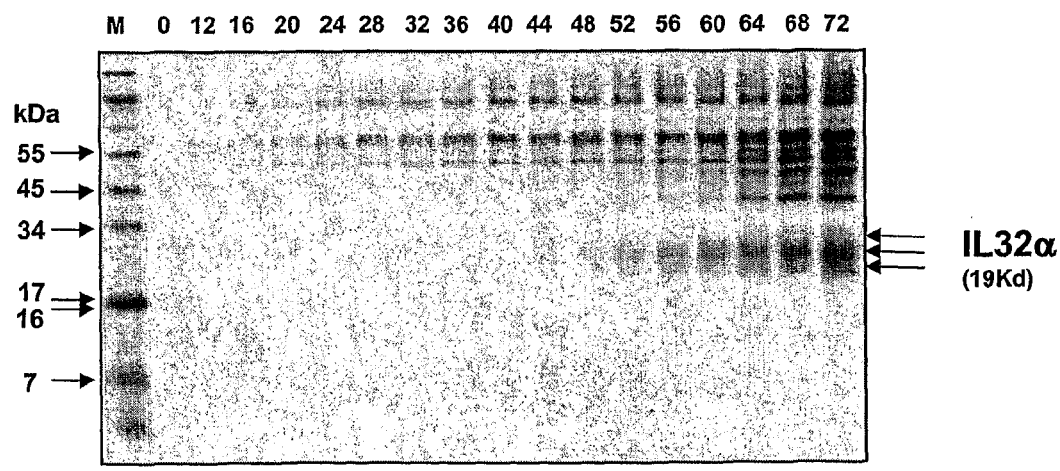

FIG. 21 shows (A) a profile for fed-batch fermentation of a recombinant yeast strain containing pYGT3-hIL32α and (B) the results of SDS-PAGE for analyzing proteins secreted into the medium according to fermentation time.

Figure 22:
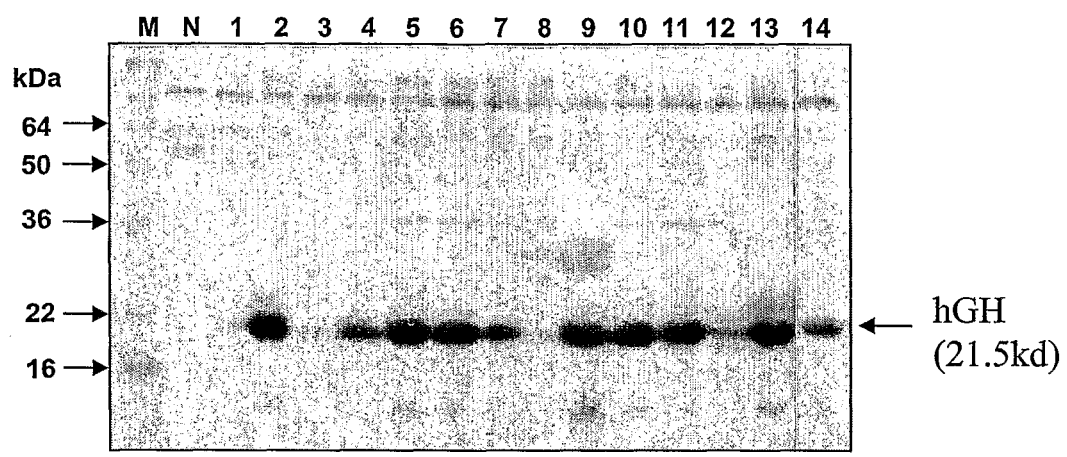
Figure 22:
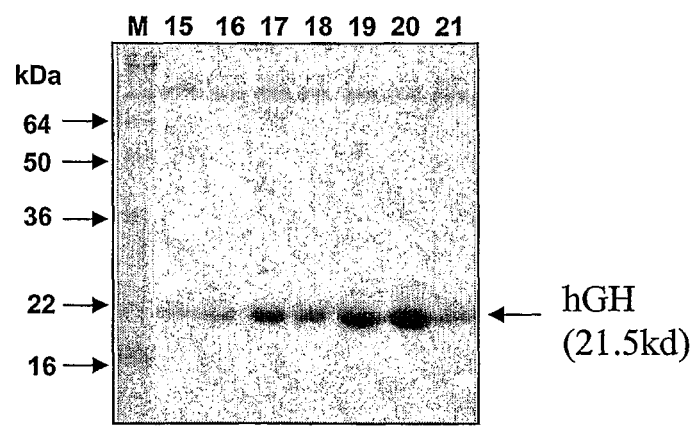

FIG. 22 shows the results of SDS-PAGE of culture supernatants of yeast cells secreting human growth hormone (lane M: protein size marker; lane N: culture supernatant of untransformed yeast cells as a negative control; lane 1: culture supernatant of yeast cells containing pYGT1-hGH, lane 2: pYGT2-hGH; lane 3: pYGT3-hGH; lane 4: pYGT4-hGH; lane 5: pYGT5-hGH; lane 6: pYGT6-hGH; lane 7: pYGT7-hGH; lane 8: pYGT8-hGH; lane 9: pYGT9-hGH; lane 10: pYGT21-hGH; lane 11: pYGT13-hGH; lane 12: pYGT25-hGH; lane 13: pYGT17-hGH; lane 14: pYGT22-hGH; lane 15: pYGT32-hGH; lane 16: pYGT19-hGH; lane 17: pYGT27-hGH; lane 18: pYGT11-hGH; lane 19: pYGT40-hGH; lane 20: pYGT43-hGH; lane 21: pYGT44-hGH.

Figure 23:
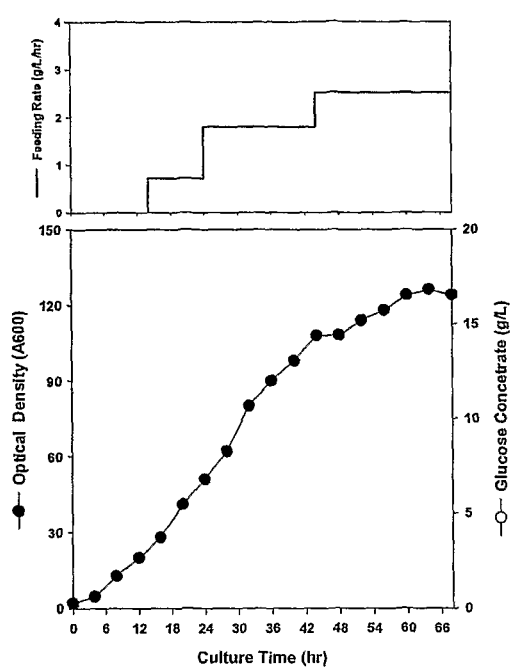
Figure 23:
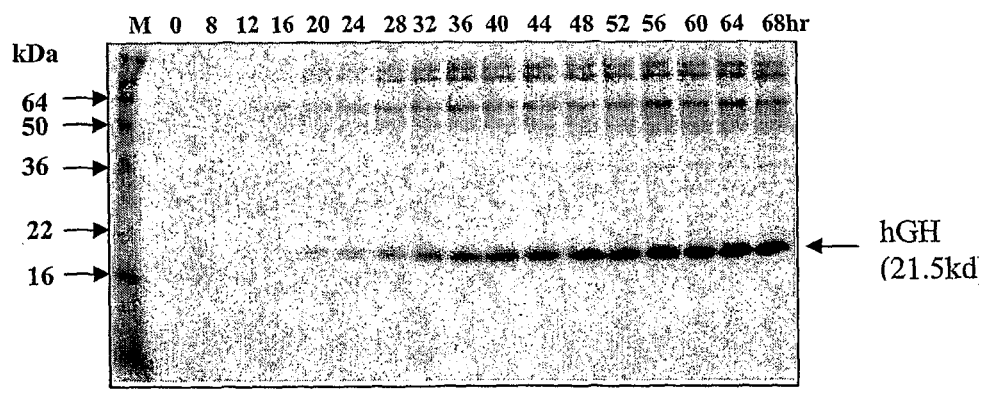

FIG. 23 shows (A) a profile for fed-batch fermentation of a recombinant yeast strain containing pYGT18-hGH and (3) the results of SDS-PAGE for analyzing proteins secreted into the medium according to fermentation time.

Figure 24:
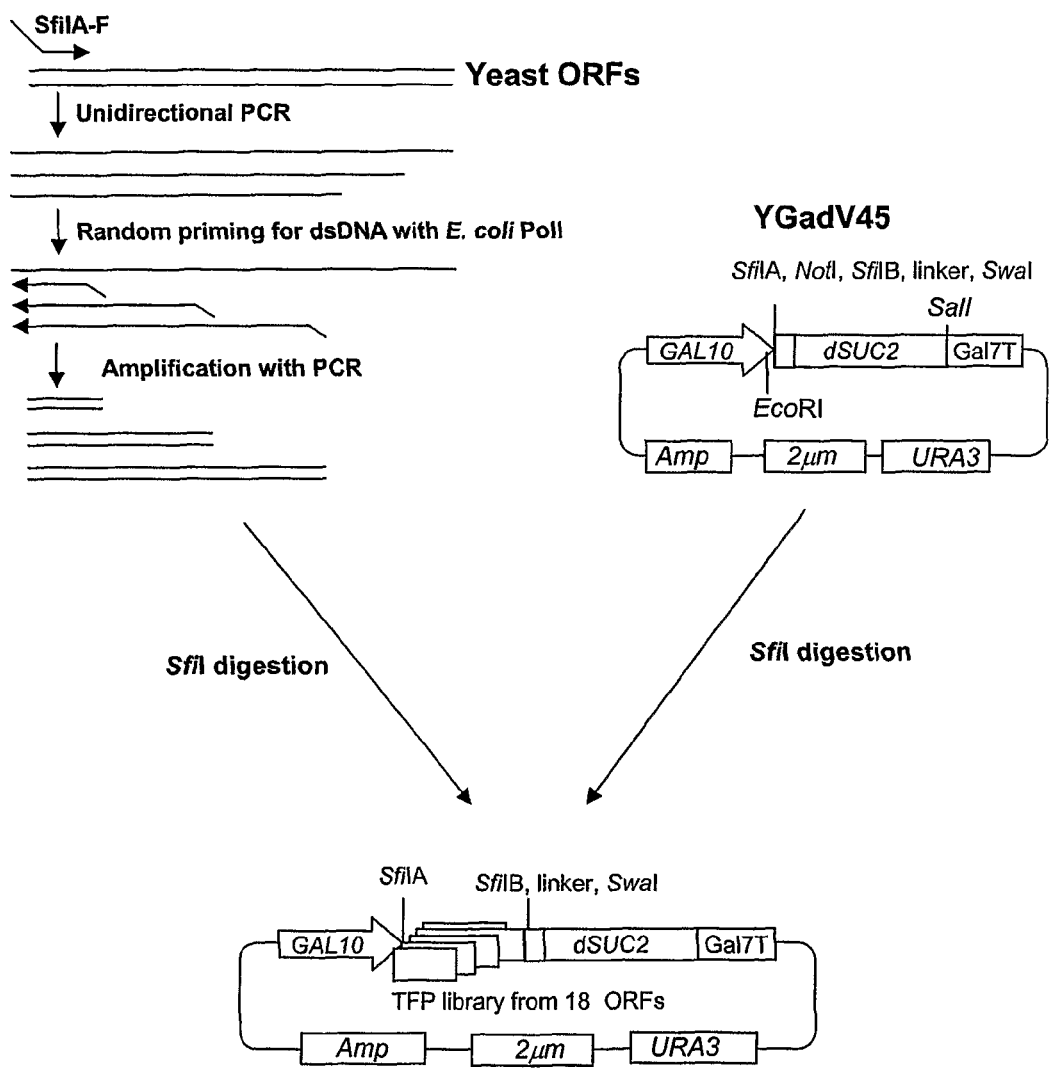

FIG. 24 shows a procedure for the construction of a TFP library from selected ORFs using a unidirectional deletion method.

Figure 25:
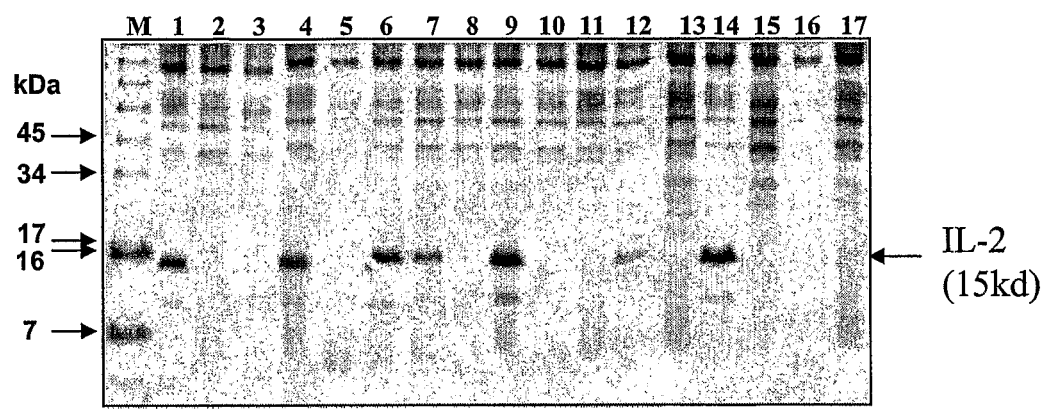
Figure 25:
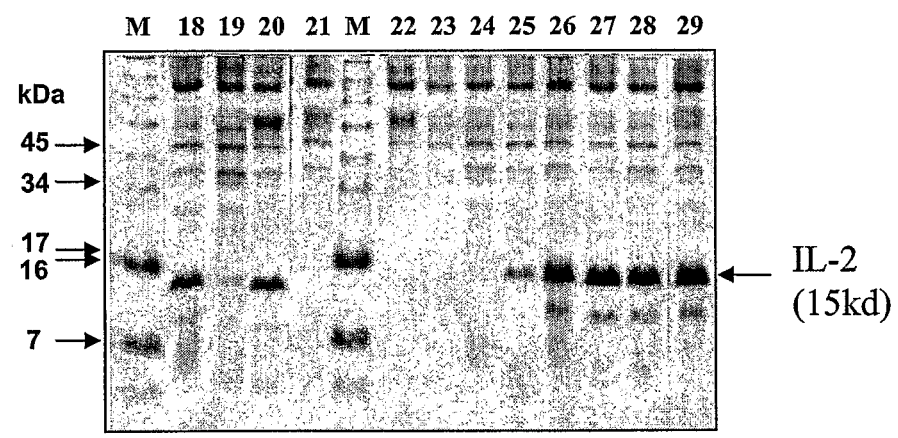

FIG. 25 shows the results of SDS-PAGE of culture supernatants of randomly selected yeast transformants transformed with the unidirectional-deleted TFP library constructed from the ORFs selected by BLAST search.

Figure 26:
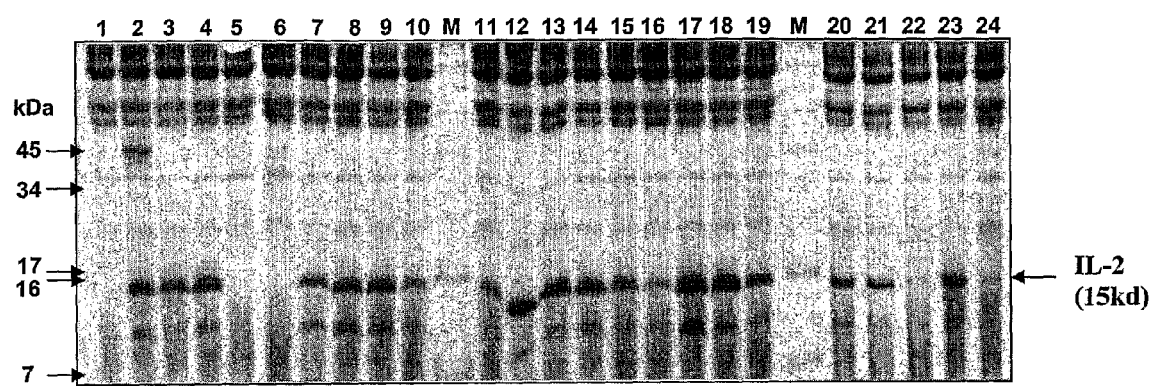

FIG. 26 shows the results of SDS-PAGE of culture supernatants of randomly selected yeast transformants transformed with the unidirectional-deletion TFP library constructed from 35 selected ORFs.

Figure 27:
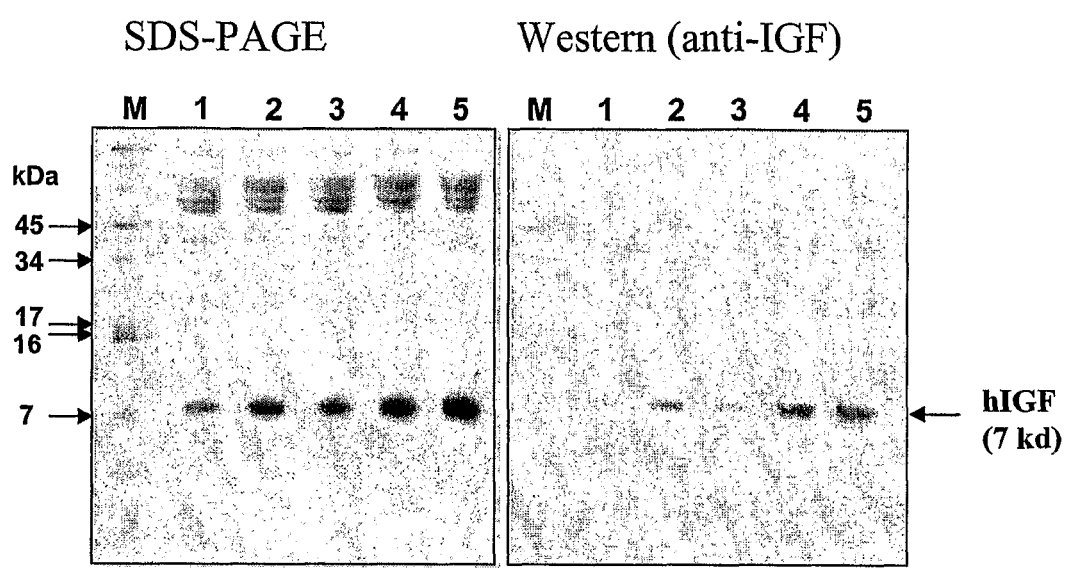

FIG. 27 shows the results of SDS-PAGE and Western blotting (anti-; hIGF) of culture supernatants of yeast cells secreting human insulin-like growth factor (Lane M; protein size marker; lane 1: culture supernatant of yeast cells containing pYGa-MFa-hIGF; lane 2: pYGa-T1α-IGF; lane 3: pYGa-T2α-IGF; lane 4: pYGa-T3α-IGF; lane 5: pYGa-T4α-IGF).

Figure 28:
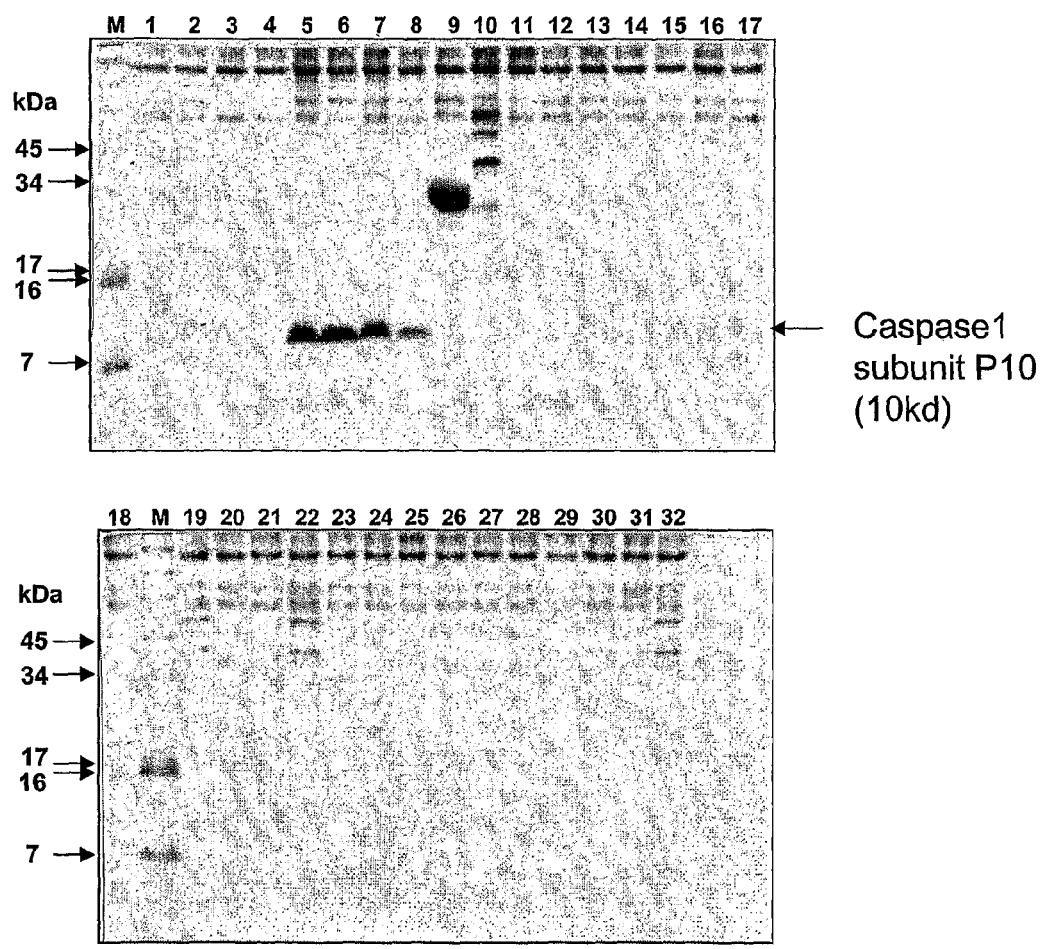

FIG. 28 shows the results of SDS-PAGE of culture supernatants of yeast cells transformed with TFP vectors for the secretion of human caspase-11 subunit P10 (lane M: protein size marker; lane 1: culture supernatant of yeast cells with pYGT1-hP10; lane 2: pYGT2-hP10; lane 3: pYGT3-hP10; lane 4: pYGT4-hP10; lane 5: pYGT5-hP10; lane 6: pYGT6-hP10; lane 7: pYGT7-hP10; lane 8: pYGT8-hP10; lane 9: pYGT9-hP10; lane 10: pYGT21-hP10; lane 11: pYGT13-hP10; lane 12: pYGT25-hP10; lane 13: pYGT17-hP10; lane 16: pYGT22-hP10; lane 18: pYGT18-hP10; lane 19: pYGT33-hP10; lane 20: pYGT19-hP10; lane 21: pYGT27-hP10; lane 22: pYGT11-hP10; lane 24: pYGT39-hP10; lane 25: pYGT40-hP10; lane 28: pYGT43-hP10; lane 29: pYGT44-hP10; lane 32: negative control).

Figure 29:
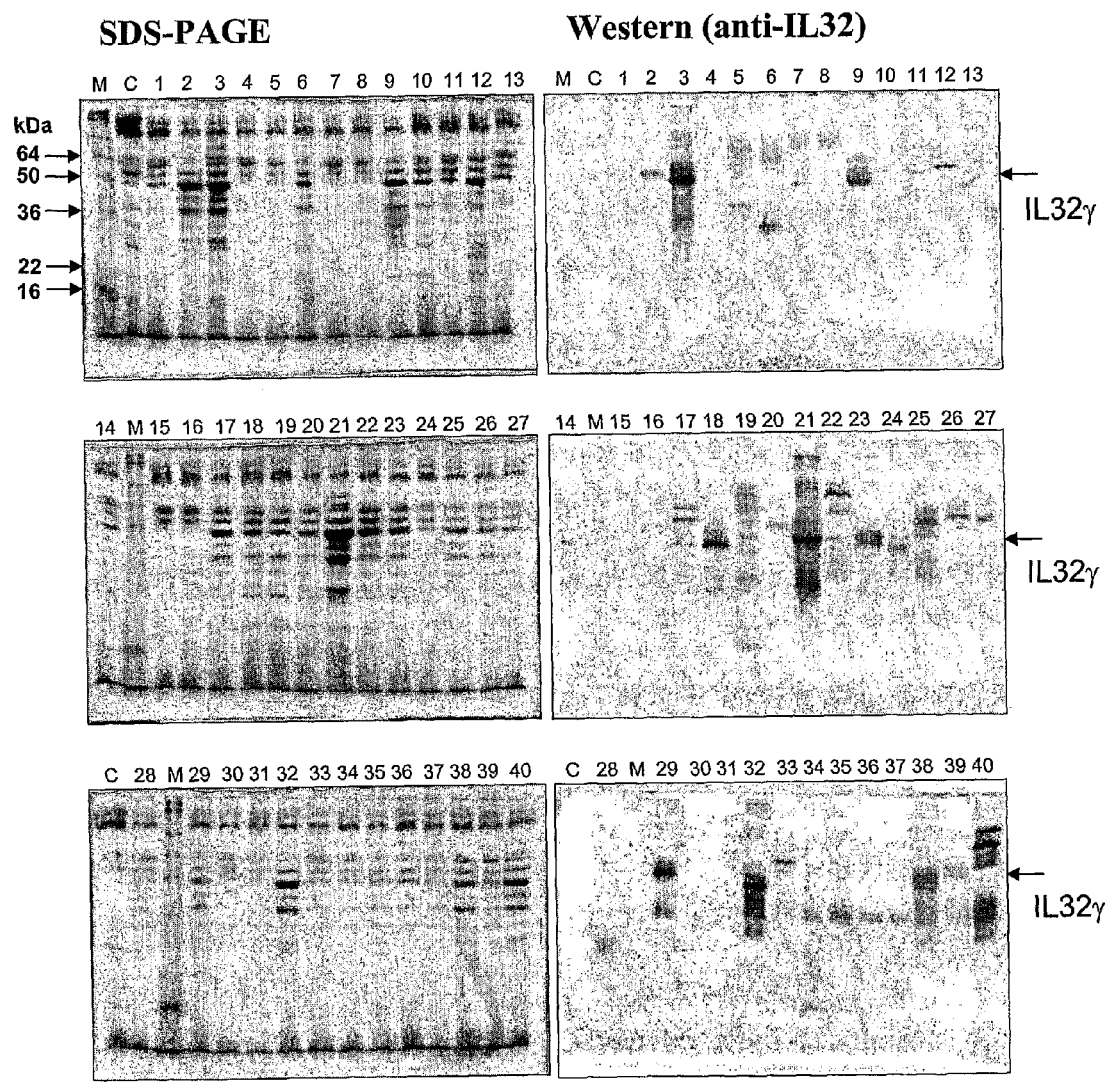

FIG. 29 shows the results of SDS-PAGE and Western blotting (anti-IL32) of culture supernatants of yeast cells secreting human interleukin 32 gamma (lane M: protein size marker; lane C: culture supernatant of untransformed yeast cells as a negative control; lane 1: pYGT1-IL32γ; lane 2: pYGT2-IL32γ; lane 3: pYGT3-IL32γ; lane 4: pYGT4-IL32γ; lane 5: pYGT5-IL32γ; lane 6: pYGT6-IL32γ; lane 7: pYGT7-IL32γ; lane 8: pYGT8-IL32γ; lane 9: pYGT9-IL32γ; lane 10: pYGT21-IL32γ; lane 11: pYGT13-IL327; lane 12: pYGT25-IL32γ; lane 13: pYGT17-IL32γ; lane 16: pYGT22-IL327; lane 18: pYGT18-IL32γ; lane 19: pYGT33-IL32γ; lane 20: pYGT19-IL32γ; lane 21: pYGT27-IL32γ; lane 22: pYGT11-IL32γ; lane 24: pYGT39-IL32γ; lane 25: pYGT40-IL32γ; lane 28: pYGT43-IL32γ; lane 29: pYGT44-IL32γ; lane 33: pYGT48-IL32γ; lane 35: pYGT50-IL32γ; lane 36: pYGT51-IL32γ; lane 37: pYGT52-IL32γ; lane 39: pYGT54-IL32γ).

Figure 30:
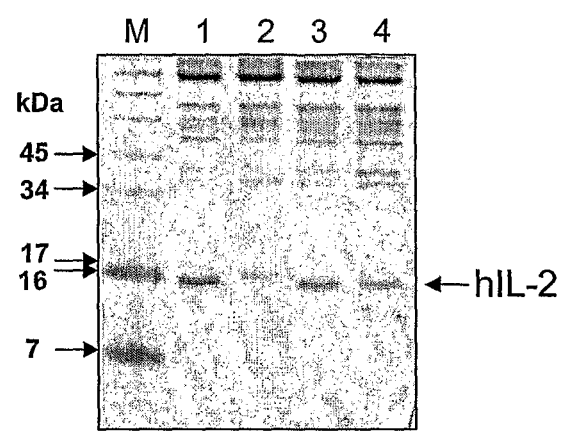

FIG. 30 shows the results of SDS-PAGE of culture supernatants of yeast cells secreting human interleukin-2 (lane M: protein size marker; lane 1: culture supernatant of yeast cells containing YGaSW-pSUN-IL2; lane 2: YGaSW-pSED-IL2; lane 3: YGaSW-pUNK-IL2; lane 4: YGaSW-pMUC-IL2).

DETAILED DESCRIPTION OF THE INVENTION

The present invention addresses the need for a rapid and efficient screening technique for identification of a TFP specifically applicable to a target protein for maximal secretion of the target protein. While the invention is useful to optimize the recombinant expression of any protein, it is particularly useful to enable the production of proteins that cannot be produced on a large scale and/or at low cost due to their low level of expression in known expression systems.

In one embodiment, the invention relates to a method of identifying a target protein specific TFP, said method comprising:

(i) co-transforming a plurality of reporter protein deficient host cells with a plurality of linear vectors and a nucleotide sequence encoding a target protein to produce a plurality of transformed host cells, wherein each of said linear vectors comprises a nucleic acid fragment from a library of nucleic acid fragments and a nucleotide sequence encoding a N-terminal amino acid-deleted reporter protein, and wherein said nucleotide sequence encoding a target protein comprises, at the 3' end, a nucleotide sequence encoding the N-terminal amino acids deleted from said reporter protein in said linear vector, and at the 5' end, a linker DNA;

(ii) incubating said plurality of transformed host cells under conditions effective to allow in vivo recombination of said linear vectors and said nucleotide sequence encoding a target protein;

(iii) identifying a cell showing an activity of the reporter protein from the plurality of transformed host cells of (ii); and (iv) identifying a TFP from the cell identified in (iii); wherein said TFP comprises a nucleic acid fragment which induces the secretion of said target protein.

Another embodiment of the invention relates to a method of identifying a target protein specific TFP library, said method comprising:

(i) co-transforming a plurality of reporter protein deficient host cells with a plurality of linear vectors and a nucleotide sequence encoding a target protein to produce a plurality of transformed host cells, wherein each of said linear vectors comprises a nucleic acid fragment from a library of nucleic acid fragments and a nucleotide sequence encoding a N-terminal amino acid-deleted reporter protein, and wherein said nucleotide sequence encoding a target protein comprises, at the 3' end, a nucleotide sequence encoding the N-terminal amino acids deleted from said reporter protein in said linear vector, and at the 5' end, a linker DNA;

(ii) incubating said plurality of transformed host cells under conditions effective to allow in vivo recombination of said linear vectors and said nucleotide sequence encoding a target protein;

(iii) identifying cells showing an activity of the reporter protein from the plurality of transformed host cells of (ii); and (iv) identifying a TFP library from the cells identified in (iii);

wherein said TFP library comprises nucleic acid fragments which individually induce the secretion of said target protein.

The library of nucleic acid fragments may be obtained from DNA of any type, including genomic DNA, cDNA, synthetic DNA, and recombinant DNA. Nucleic acids other than DNA may also be used, including RNA and non-naturally occurring nucleic acids.

TFPs may be identified from the DNA of any eukaryotic or prokaryotic organism, including bacteria, fungi (e.g., yeast), plants, and animals (e.g., mammals). Suitable bacteria include, but are not limited to *Escherichia* and *Bacillus* species. Suitable yeast include, but are not limited to *Candida, Debaryomyces, Hansenula, Kluyveromyces, Pichia, Schizosaccharonyces, Yarrowia, Saccharomyces, Schwanniomyces*, and *Arxula* species. Examples of specific species include *Candida utilis, Candida boidinii, Candida albicans, Kluyveroinyces lactis, Pichia pastoris, Pichia stipitis, Schizosaccharomyces pombe, Saccharomyces cerevisiae, Hansenula polymorpha, Yarrowia lipolytica, Schwanniomyces occidentalis*, and *Arxula adeninivorans*. Other fungi that may serve as a source of DNA include, but are not limited to *Aspergillus, Penicillium, Rhizopus*, and *Trichoderma* species. Plants that may serve as a source of DNA include, but are not limited to *Arabidopsis*, maize, tobacco, and potato. Suitable animals include, but are not limited to humans, mice, rats, rabbits, dogs, cats, and monkeys.

The nucleic acid fragments may be derived from the entire genome of an organism, e.g., an entire genomic or cDNA library. The fragments may also be derived from any subset of the entire genome, e.g., a subtracted library or a sized library.

In one embodiment, the nucleic acid fragments are derived from a library of pre-selected candidate TFPs, e.g., a library comprising TFPs that have been identified in previous screens. In a particular embodiment, the library of pre-selected candidate TFPs is a library of core TFPs that have been identified as effective TFPs for one or more target proteins.

In another embodiment, the library of pre-selected candidate TFPs is obtained by transforming a plurality of reporter protein-deficient host cells with a variety of vectors comprising a library of nucleic acid fragments and a reporter protein-encoding nucleic acid sequence, collecting cells that grow, isolating vectors from the cells, and isolating nucleic acid fragments from the vectors, thereby obtaining a TFP library comprising the nucleic acid fragments which individually induce secretion of the reporter protein.

In a further embodiment, the library of pre-selected candidate TFPs is derived from sequences identified in a genome database by searching for (i) genes containing a pre-secretion signal homologous with those of one or more previously identified TFPs; (ii) genes comprising a secretion signal sequence; or (iii) genes encoding proteins passing through endoplasmic reticulum (e.g., cell wall proteins, excretory proteins, plasma membrane proteins, vacuolar proteins, bud proteins).

In another embodiment, the library of pre-selected candidate TFPs is obtained by diversifying previously identified TFPs, e.g., by unidirectional deletion, mutation, addition of functional sequences (e.g., glycosylation sites) or swapping of pre- and pro-signal sequences between TFPs.

In one embodiment, the nucleic acid fragments have a size of less than 1000 base pairs, e.g., less than 700, 500, or 300 base pairs. In a further embodiment, the library of nucleic acid fragments is constructed by enzymatic cleavage of the DNA, by cDNA synthesis, or by recombinant DNA technology (e.g., unidirectional deletion, mutagenesis).

The linear vectors of the present invention may be any vector that is functional in the selected host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. The vectors of the present invention are capable of directing the expression of genes encoding target proteins to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), that serve equivalent functions.

Expression of proteins in prokaryotes may be carried out with vectors containing constitutive or inducible promoters directing the expression of the target protein-reporter protein fusion. Examples of suitable *E. coli* expression vectors include pTrc (Amrann et al., *Gene* 69:301-315 (1988)) and pET (Studier et al., GENE EXPRESSION TECHNOLOGY: METHODS IN ENZYMOLOGY 185, Academic Press, San Diego, Calif. (1990) 60-89).

For expression in yeast cells, suitable yeast expression vectors include, but are not limited to pYepSec1 (Baldari et al., *EMBO J.* 6:229-234 (1987)), pMFa (Kurjan et al., *Cell* 30:933-943 (1982)), pJRY88 (Schultz et al, *Gene* 54:113-123 (1987)), pYES2 (Invitrogen Corporation, San Diego, Calif.), and picZ (Invitrogen Corp, San Diego, Cal.).

For expression in insect cells, baculovirus expression vectors may be used. Baculovirus vectors available for expression of proteins in cultured insect cells (e.g., SF9 cells) include the pAc series (Smith et al., *Mol. Cell. Biol.* 3:2156-2165 (1983)) and the pVL series (Lucklow et al., *Virology* 170:31-39 (1989)).

In another embodiment, the host cells are mammalian cells and the vector is a mammalian expression vector. Examples of mammalian expression vectors include pCDM8 (Seed, *Nature* 329:840 (1987)) and pMT2PC (Kaufman et al., *EMBO J.* 6: 187-195 (1987)). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells, see, e.g., Chapters 16 and 17 of Sambrook et al., MOLECULAR CLONING: A LABORATORY MANUAL. 2nd ed., Cold Spring Harbor, Laboratory, Cold Spring Harbor Laboratory Press, Cold Spring Harbor, N.Y., 1989.

Preferred vectors include, but are not limited to, plasmids, phages, cosmids, episomes, viral particles or viruses, and integratable DNA fragments (i.e., fragments integratable into the host genome by homologous recombination). Preferred viral particles include, but are not limited to, adenoviruses, baculoviruses, parvoviruses, herpesviruses, poxviruses, adenoassociated viruses, Semliki Forest viruses, vaccinia, viruses, and retroviruses. Preferred expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™ (Invitrogen).

In one embodiment, expression vectors are replicable DNA constructs in which a DNA sequence encoding the target protein is operably linked or connected to suitable control sequences capable of effecting the expression of the target protein in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include, but are not limited to a transcriptional promoter, enhancers, an optional operator sequence to control transcription, polyadenylation signals, a sequence encoding suitable mRNA ribosomal binding and sequences which control the termination of transcription and translation. Such regulatory sequences are described, for example, in Goeddel; GENE EXPRES- SION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct, expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

The expression vectors of the invention can be introduced into host cells to thereby produce proteins or peptides, including fusion proteins or peptides, encoded by nucleic acids as described herein. Preferred vectors preferably contain a promoter that is recognized by the host organism. The promoter sequences of the present invention may be prokaryotic, eukaryotic or viral. Examples of suitable prokaryotic sequences include the PR and PL promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of *E. coli* and the SV40 early promoter (Benoist et al., *Nature*, 290:304-310 (1981)), which is incorporated herein by reference in its entirety). For yeast, examples of suitable promoters include, but are not limited to GAPDH, PGK, ADH, PHO5, GAL1, and GAL10. Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metallothionein.

Additional regulatory sequences can also be included in preferred vectors. Examples of suitable regulatory sequences are represented by the Shine-Dalgarno sequence of the replicase gene of the phage MS-2 and of the gene cII of bacteriophage lambda.

Moreover, suitable expression vectors can include an appropriate, marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by, the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and target protein DNA. An example of a suitable marker is dihydrofolate reductase (DHFR) or thymidine kinase (see, U.S. Pat. No. 4,399,216).

Nucleotide sequences encoding the target protein may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.* 3:280 (1983), Cosman et al., *Mol. Immunol.* 23:935 (1986), Cosman et al., *Nature* 312:768 (1984), EP-A-0367566, and WO 91/18982, each of which is incorporated herein by reference in its entirety.

The host cells used in the present invention may be any host cells know to those of skill in the art. Suitable host cells include bacterial, fungal, (e.g., yeast), plant, or animal (e.g., mammalian or insect) cells. Suitable yeast cells include *Candida*, *Debaryomyces*, *Hansenula*, *Kluyveroinyces*, *Pichia*, *Schizosaccharomyces*, *Yarrowia*, *Saccharomyces*, *Schwanniomyces*, and *Arxula* species. Specific examples include *Candida utilis*, *Candida boidinii*, *Candida albicans*, *Kluyveromyces lactis*, *Pichia pastoris*, *Pichia stipitis*, *Schizosaccharomyces pombe*, *Saccharomyces cerevisiae*, *Hansenula polymorpha*, *Yarrowia lipolytica*, *Schwannioinyces occidentalis*, and *Arxula adeninivorans*. Other suitable fungi include *Aspergillus*, *Penicillium*, *Rhizopus*, and *Trichoderma* species. Bacteria that may be used as host cells: include *Escherichia*, *Pseudomonas*, and *Bacillus* species. Suitable plant host cells include *Arabidopsis*, maize, tobacco, and potato. Animal cells include cells from humans, mice, rats, rabbits, dogs, cats, monkeys, and insects. Examples include CHO, COS 1, COS 7, BSC 1, BSC 40, BMT 10, and Sf9 cells.

In a particular embodiment, the host cells are yeast cells, and the nucleic acid fragments are isolated from the genome or cDNA of a yeast.

Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts.

Any reporter protein that is rapidly and efficiently detectable may be used in the present invention. In one embodiment, the reporter protein has an activity that can be positively selected for in order to automate the screening process. In an additional embodiment, the reporter protein is a protein that is secreted into the extracellular space, e.g., invertase, sucrase, cellulase, xylanase, maltase, amylase, glucoamylase, galactosidase (e.g., alpha-galactosidase beta-galactosidase, melibiase), phosphatase (e.g., PHO5), beta-lactamase, lipase or protease. In a particular embodiment, the secreted protein permits a cell to grow on a particular substrate. As an example of reporter system in mammalian cell, CD2/neomycin-phosphotransferase (Ceo) gene can be used as a secretion reporter in the media containing antibiotics G418 to trap the secretion pathway genes in mouse embryonic stem cells (De-Zolt et al., Nucleic Acid Res. 34:e25 (2006)).

In one embodiment, the host cells are yeast, the reporter protein is invertase and the transformed yeast cells are selected for their ability to grow on sucrose or raffinose. In another embodiment, the host cells are yeast, the reporter protein is melibiase and the transformed yeast cells are selected for their ability to grow on melibiose. In a further embodiment, the host cells are yeast, the reporter protein is amylase (e.g., an endoamylase, exoamylase, β-amylase, or glucoamylase), the yeast cells are non-amylolytic, and the transformed cells are screened for their ability to degrade starch. In an additional embodiment, the step of identifying cells showing an activity of the reporter protein occurs by using a reporter protein which provides resistance to a growth inhibitor, e.g., an antibiotic. In another embodiment, the reporter protein is a protein that can be detected visually, e.g., green fluorescent protein or luciferase. In one embodiment, the step of identifying cells showing an activity of the reporter protein occurs by using two or more reporter proteins, e.g., lipase and invertase.

The host cells of the present invention do not exhibit reporter protein activity. In one embodiment, the host cells naturally do not express the reporter protein. In other embodiments, the gene(s) encoding the reporter protein have been deleted in whole or in part or have been mutated such that the reporter protein is not expressed or is expressed in an inactive form. Methods for rendering a cell deficient in a particular protein are well known in the art and any such method may be used to prepare the host cells of the present invention (Sambrook et al., supra). For yeast, a reporter gene deficiency can be introduced using well known gene replacement techniques (Rothstein, *Meth. Enzymol.* 194:281 (1991)).

The linear vector of the invention comprises a nucleic acid fragment and a nucleotide sequence encoding a N-terminal amino acid-deleted reporter protein. The N-terminal amino acid deletion may encompass any number of amino acids as long as the deletion is sufficient to substantially eliminate reporter protein activity. For example, the deletion may encompass about 5, 10, 15, 20, 25, 30, 35, 40, 45, or 50 or more amino acids from the N-terminus of the reporter protein.

The methods of the present invention may be used with any target protein for which there is a desire for high level recombinant expression. The target protein may be one that is being studied for research purposes or one that is being produced for commercial purposes, e.g., therapeutic or industrial use. The target protein may be from any plant, animal, or microorganism, and may be naturally occurring or modified in any way, as long as it can be encoded by a nucleic acid. In one embodiment the target protein is a human protein. In another embodiment, the target protein is a cytokine, serum protein, colony stimulating factor, growth factor, hormone, or enzyme. For example, the target protein may be selected from an interleukin, coagulation factor, interferon-α, -β or -γ, granulocyte-colony stimulating factor, granulocyte macrophage-colony stimulating factor, tissue growth factor, epithelial growth factor, TGFα, TGFβ, epidermal growth factor, platelet-derived growth factor, fibroblast growth factor, follicle stimulating hormone, thyroid stimulating hormone, antidiuretic hormone, pigmentary hormone, parathyroid hormone, luteinizing hormone-releasing hormone, carbohydrate-specific enzymes, proteolytic enzymes, lipases, oxidoreductases, transferases, hydrolases, lyases, isomerases, ligases, immunoglobulins, cytokine receptors, lactoferrin, phospholipase A2-activating protein, insulin, tumor necrosis factor, calcitonin, calcitonin gene related peptide, enkephalin, somatomedin, erythropoietin, hypothalamic releasing factor, prolactin, chorionic gonadotropin, tissue plasminogen activator, growth hormone releasing peptide, thymic humoral factor, anticancer peptides, or antibiotic peptides. Specific examples include, but are not limited to human interleukin-2, human interleukin-1β, human interleukin-6, human interleukin-32α, -32β or -32γ, Factor VII, Factor VIII, Factor IX, human serum albumin, human interferon-α, -β or -γ, human granulocyte-colony stimulating factor, human granulocyte macrophage-colony stimulating factor, human growth hormone, human platelet-derived growth factor, human basic fibroblast growth factor, human epidermal growth factor, human insulin-like growth factor, human nerve growth factor, human transforming growth factor β-1, human follicle stimulating hormone, glucose oxidase, glucodase, galactosidase, glucocerebrosidase, glucuronidase, asparaginase, arginase, arginine deaminase, peroxide dismutase, endotoxinase, catalase, chymotrypsin, uricase, adenosine diphosphatase, tyrosinase, bilirubin oxidase, bovine galactose-1-phosphate uridyltransferase, jellyfish green fluorescent protein, *Candida antarctica* lipase B, *Candida rugosa* lipase, fungal chloroperoxidase, β-galactosidase, resolvase, α-galactosidase, β-glucosidase, trehalose synthase, cyclodextrin glycosyl transferase, xylanase, phytase, human lactoferrin, human erythropoietin, human paraoxonase, human growth differentiation factor 15, human galectin-3 binding protein, human serine protease inhibitor, Kunitz type 2, human Janus kinase 2, human fms-like tyrosine kinase 3 ligand, human YM1 & 2, human CEMI, human diacylglycerol acyltransferase, human leptin, human mL259, human proteinase 3, human lysozyme, human DEAD box protein 41, human etoposide induced protein 24, mouse caspase1, bovine angiogenin, and earthworm lumbrokinase.

In one embodiment, the target protein is a protein that is difficult to produce using conventional recombinant production methods, that is, a protein that is not produced at all or is only produced at low levels. In another embodiment, the target protein is one that is readily produced using known expression systems, but for which there is a desire to achieve higher levels of expression.

Nucleic acids encoding a target protein may be obtained from any source using routine techniques well known in the art, including isolation from a genomic or cDNA library, amplification by PCR, or chemical synthesis.

The nucleotide sequence encoding a target protein used in the methods of the present invention comprises at the 5' end a linker DNA that is used for in vivo recombination with the linear vectors of the invention and further comprises at the 3' end a nucleotide sequence encoding a portion of the N-terminus of the reporter protein, including the N-terminal amino acids deleted in the linear vector and sufficient additional amino acids to allow in vivo recombination between the nucleotide sequence encoding a target protein and the linear vector when they are co-transformed into the host cell. In one embodiment, the sequence encoding a portion of the N-terminus of the reporter protein comprises at least 20 base pairs that overlap with the reporter, protein-encoding sequence of the linear vector, e.g., at least 30 or 40 base pairs. The addition of the 5' linker and the 3' reporter protein sequence to the nucleotide sequence encoding a target protein may be carried out using routine recombinant DNA techniques, e.g., PCR and/or restriction enzyme cleavage and ligation.

The linker DNA of the invention must be of sufficient length and have sufficient sequence identity to a portion of the nucleotide sequence of the linear vector to allow in vivo recombination between the target protein-encoding nucleotide sequence and the linear vector when they are co-transformed into a host cell. In one embodiment, the linker DNA is more than 20 base pairs in length, e.g., more than 30 or 40 base pairs in length. In a further embodiment, the linker DNA is at least 80% identical to the corresponding sequence on the linear vector, e.g., at least 85%, 90%, 95%, or 99% identical.

In one embodiment, the linker DNA encodes a protease recognition sequence thereby allowing cleavage at the junction of the TFP and the target protein. For example, the linker DNA may encode a yeast kex2p- or Kex2-like protease recognition sequence (e.g., an amino acid sequence comprising Lys-Arg, Arg-Arg, or Leu-Asp-Lys-Arg (SEQ ID NO:214)), a mammalian furin-recognition sequence (e.g., an amino acid sequence comprising Arg-X-X-Arg), a factor Xa-recognition sequence (e.g., an amino acid sequence comprising Ile-Glu-Gly-Arg (SEQ ID NO:215)), an enterokinase-recognition sequence (e.g., an amino acid sequence comprising Asp-Asp-Lys), a subtilisin-recognition sequence (e.g., an amino acid sequence comprising Ala-Ala-His-Tyr (SEQ ID NO:216)), a tobacco etch virus protease-recognition sequence (e.g., an amino acid sequence comprising Glu-Asn-Leu-Tyr-Phe-Gln- Gly (SEQ ID NO:217)), a ubiquitin hydrolase-recognition sequence (e.g., an amino acid sequence comprising Arg-Gly-Gly) or a thrombin-recognition sequence (e.g., an amino acid sequence comprising Arg-Gly-Pro-Arg (SEQ ID NO:218)).

In another embodiment, the linker DNA encodes an affinity tag, e.g., GST, MBP, NusA, thioredoxin, ubiquitin, FLAG, BAP, 6HIS, STREP, CBP, CBD, or S-tag.

In a further embodiment, the linker DNA encodes a restriction enzyme recognition site, e.g., a SfiI site. In another embodiment, the linker DNA encodes a restriction enzyme recognition site and a protease recognition sequence (e.g., kex2p-like protease- or kex-2p-recognition sequence).

The present invention relates to a TFP identified by the methods of the invention or a derivative or fragment thereof. In one embodiment, the TFP is selected from the group consisting of TFP-9 (SEQ ID NO:29), TFP-13 (SEQ ID NO:31), TFP-17 (SEQ ID NO:33), TFP-18 (SEQ ID NO:35), TFP-19 (SEQ ID NO:37), TFP-20 (SEQ ID NO:39), TFP-21 (SEQ ID NO:41), TFP-25 (SEQ ID NO:43), TFP-27 (SEQ ID NO:45), TFP-11 (SEQ ID NO:61), TFP-22 (SEQ ID NO:63), TFP-29 (SEQ ID NO:65), TFP-34 (SEQ ID NO:67), TFP-38 (SEQ ID NO:69), TFP-39 (SEQ ID NO:129), TFP-43 (SEQ ID NO:131), TFP-44 (SEQ ID NO:133), TFP-48 (SEQ ID NO:135), TFP-52 (SEQ ID NO:137), TFP-54 (SEQ ID NO:139), TFP-40 (SEQ ID NO:175), TFP-50 (SEQ ID NO:177), TFP-51 (SEQ ID NO:179), TFP-57 (SEQ ID NO:181), TFP-58 (SEQ ID NO:183), TFP-59 (SEQ ID NO:185), TFP-5 (SEQ ID NO:200), TFP-6 (SEQ ID NO:202), TFP-7 (SEQ ID NO:204), TFP-8 (SEQ ID NO:206), PpTFP-1 (SEQ ID NO:84), PpTFP-2 (SEQ ID NO:86), PpTFP-3 (SEQ ID NO:88), and PpTFP-4 (SEQ ID NO:90) or a derivative or fragment thereof.

The invention further relates to a TFP library comprising two or more of the TFPs identified by the methods of the invention or a fragment or derivative thereof. In one embodiment, the TFP library comprises TFPs identified as effective for a particular target protein. In another embodiment, the TFP library comprises TFPs identified as effective for more than one target protein. In a particular embodiment, the TFP library comprises two or more (e.g., 4, 6, 8, 10, or 12 or more) TFPs selected from the group consisting of TFP-9 (SEQ ID NO:29), TFP-13 (SEQ ID NO:31), TFP-17 (SEQ ID NO:33), TFP-18 (SEQ ID NO:35), TFP-19 (SEQ ID NO:37), TFP-20 (SEQ ID NO:39), TFP-21 (SEQ ID NO:41), TFP-25 (SEQ ID NO:43), TFP-27 (SEQ ID NO:45), TFP-11 (SEQ ID NO:61), TFP-22 (SEQ ID NO:63), TFP-29 (SEQ ID NO:65), TFP-34 (SEQ ID NO:67), TFP-38 (SEQ ID NO:69), TFP-39 (SEQ ID NO:129), TFP-43 (SEQ ID NO:131), TFP-44 (SEQ ID NO:133), TFP-48 (SEQ ID NO:135), TFP-52 (SEQ ID NO:137), TFP-54 (SEQ ID NO:139), TFP-40 (SEQ ID NO:175), TFP-50 (SEQ ID NO:177), TFP-51 (SEQ ID NO:179), TFP-57 (SEQ ID NO:181), TFP-58 (SEQ ID NO:183), TFP-59 (SEQ ID NO:185), TFP-5 (SEQ ID NO:200), TFP-6 (SEQ ID NO:202), TFP-7 (SEQ ID NO:204), TFP-8 (SEQ ID NO:206), PpTFP-1 (SEQ ID NO:84), PpTFP-2 (SEQ ID NO:86), PpTFP-3 (SEQ ID NO:88), and PpTFP-4 (SEQ ID NO:90) or a derivative or fragment thereof.

In a further embodiment, the TFP library comprises six or more (e.g., 8, 10, 12, or 15 or more) TFPs selected from the group consisting of TFP-9 (SEQ ID NO:29), TFP-13 (SEQ ID NO:31), TFP-17 (SEQ ID NO:33), TFP-18 (SEQ ID NO:35), TFP-19 (SEQ ID NO:37), TFP-20 (SEQ ID NO:39), TFP-21 (SEQ ID NO:41), TFP-25 (SEQ ID NO:43), TFP-27 (SEQ ID NO:45), TFP-11 (SEQ ID NO:61), TFP-22 (SEQ ID NO:63), TFP-29 (SEQ ID NO:65), TFP-34 (SEQ ID NO:67), TFP-38 (SEQ ID NO:69), TFP-39 (SEQ ID NO:129), TFP-43 (SEQ ID NO:131), TFP-44 (SEQ ID NO:133), TFP-48 (SEQ ID NO:135), TFP-52 (SEQ ID NO:137), TFP-54 (SEQ ID NO:139), TFP-40 (SEQ ID NO:175), TFP-50 (SEQ ID NO:177), TFP-51 (SEQ ID NO:179), TFP-57 (SEQ ID NO:181), TFP-58 (SEQ ID NO:183), TFP-59 (SEQ ID NO:185), TFP-5 (SEQ ID NO:200), TFP-6 (SEQ ID NO:202), TFP-7 (SEQ ID NO:204), TFP-8 (SEQ ID NO:206), PpTFP-1 (SEQ ID NO:84), PpTFP-2 (SEQ ID NO:86), PpTFP-3 (SEQ ID NO:88), PpTFP-4 (SEQ ID NO:90), TFP-1 (SEQ ID NO:219), TFP-2 (SEQ ID NO:221), TFP-3 (SEQ ID NO:223), TFP-4 (SEQ ID NO:225), and TFP 32 (SEQ ID NO:208) or a derivative or fragment thereof.

The present invention further relates to a nucleic acid encoding a TFP identified by the methods of the invention or a derivative or fragment thereof. In one embodiment, the nucleic acid encodes a TFP selected from the group consisting of TFP-9 (SEQ ID NO:29), TFP-13 (SEQ ID NO:31), TFP-17 (SEQ ID NO:33), TFP-18 (SEQ ID NO:35), TFP-19 (SEQ ID NO:37), TFP-20 (SEQ ID NO:39), TFP-21 (SEQ ID NO:41), TFP-25 (SEQ ID NO:43), TFP-27 (SEQ ID NO:45), TFP-11 (SEQ ID NO:61), TFP-22 (SEQ ID NO:63), TFP-29 (SEQ ID NO:65), TFP-34 (SEQ ID NO:67), TFP-38 (SEQ ID NO:69), TFP-39 (SEQ ID NO:129), TFP-43 (SEQ ID NO:131), TFP-44 (SEQ ID NO:133), TFP-48 (SEQ ID NO:135), TFP-52 (SEQ ID NO:137), TFP-54 (SEQ ID NO:139), TFP-40 (SEQ ID NO:175), TFP-50 (SEQ ID NO:177), TFP-51 (SEQ ID NO:179), TFP-57 (SEQ ID NO:181), TFP-58 (SEQ ID NO:183), TFP-59 (SEQ ID NO:185), TFP-5 (SEQ ID NO:200), TFP-6 (SEQ ID NO:202), TFP-7 (SEQ ID NO:204), TFP-8 (SEQ ID NO:206), PpTFP-1 (SEQ ID NO:84), PpTFP-2 (SEQ ID NO:86), PpTFP-3 (SEQ ID NO:88), and PpTFP-4 (SEQ ID NO:90) or a derivative or fragment thereof. In one embodiment, the nucleic acid comprises a nucleotide sequence selected from the group consisting of SEQ ID NOS:30, 32, 34, 36, 38, 40, 42, 44, 46, 62, 64, 66, 68, 70, 85, 87, 89, 91, 130, 132, 134, 136, 138, 140, 176, 178, 180, 182, 184, 186, 201, 203, 205, or 207 or a derivative or fragment thereof.

The invention further relates to a library of nucleic acids encoding two or more TFPs identified by the methods of the invention or a derivative or fragment thereof. In one embodiment, the library of nucleic acids encodes TFPs identified as effective for a particular target protein. In another embodiment, the library of nucleic acids encodes TFPs identified as effective for more than one target protein. In a particular embodiment, the library of nucleic acids encodes two or more (e.g., 4, 6, 8, 10, or 12 or more) TFPs selected from the group consisting of TFP-9 (SEQ ID NO:29), TFP-13 (SEQ ID NO:31), TFP-17 (SEQ ID NO:33), TFP-18 (SEQ ID NO:35), TFP-19 (SEQ ID NO:37), TFP-20 (SEQ ID NO:39), TFP-21 (SEQ ID NO:41), TFP-25 (SEQ ID NO:43), TFP-27 (SEQ ID NO:45), TFP-11 (SEQ ID NO:61), TFP-22 (SEQ ID NO:63), TFP-29 (SEQ ID NO:65), TFP-34 (SEQ ID NO:67), TFP-38 (SEQ ID NO:69), TFP-39 (SEQ ID NO:129), TFP-43 (SEQ ID NO:131), TFP-44 (SEQ ID NO:133), TFP-48 (SEQ ID NO:135), TFP-52 (SEQ ID NO:137), TFP-54 (SEQ ID NO:139), TFP-40 (SEQ ID NO:175), TFP-50 (SEQ ID NO:177), TFP-51 (SEQ ID NO:179), TFP-57 (SEQ ID NO:181), TFP-58 (SEQ ID NO:183), TFP-59 (SEQ ID NO:185), TFP-5 (SEQ ID NO:200), TFP-6 (SEQ ID NO:202), TFP-7 (SEQ ID NO:204), TFP-8 (SEQ ID NO:206), PpTFP-1 (SEQ ID NO:84), PpTFP-2 (SEQ ID NO:86), PpTFP-3 (SEQ ID NO:88), and PpTFP-4 (SEQ ID NO:90) or a derivative or fragment thereof. In one embodiment, the library of nucleic acids comprises two or more (e.g., 4, 6, 8, 10, or 12 or more) of the nucleotide sequences of SEQ ID NOS:30, 32, 34, 36, 38, 40, 42, 44, 46, 62, 64, 66, 68, 70, 85, 87, 89, 91, 130, 132, 134, 136, 138, 140, 176, 178, 180, 182, 184, 186, 201, 203, 205, or 207 or a derivative or fragment thereof.

In a further embodiment, the library of nucleic acids encodes six or more (e.g., 8, 10, 12, or 15 or more) TFPs selected from the group consisting of TFP-9 (SEQ ID NO:29), TFP-13 (SEQ ID NO:31), TFP-17 (SEQ ID NO:33), TFP-18 (SEQ ID NO:35), TFP-19 (SEQ ID NO:37), TFP-20 (SEQ ID NO:39), TFP-21 (SEQ ID NO:41), TFP-25 (SEQ ID NO:43), TFP-27 (SEQ ID NO:45), TFP-11 (SEQ ID NO:61), TFP-22 (SEQ ID NO:63), TFP-29 (SEQ ID NO:65), TFP-34 (SEQ ID NO:67), TFP-38 (SEQ ID NO:69), TFP-39 (SEQ ID NO:129), TFP-43 (SEQ ID NO:131), TFP-44 (SEQ ID NO:133), TFP-48 (SEQ ID NO:135), TFP-52 (SEQ ID NO:137), TFP-54 (SEQ ID NO:139), TFP-40 (SEQ ID NO:175), TFP-50 (SEQ ID NO:177), TFP-51 (SEQ ID NO:179), TFP-57 (SEQ ID NO:181), TFP-58 (SEQ ID NO:183), TFP-59 (SEQ ID NO:185), TFP-5 (SEQ ID NO:200), TFP-6 (SEQ ID NO:202), TFP-7 (SEQ ID NO:204), TFP-8 (SEQ ID NO:206), PpTFP-1 (SEQ ID NO:84), PpTFP-2 (SEQ ID NO:86), PpTFP-3 (SEQ ID NO:88), PpTFP-4 (SEQ ID NO:90), TFP-1 (SEQ ID NO:219), TFP-2 (SEQ ID NO:221), TFP-3 (SEQ ID NO:223), TFP-4 (SEQ ID NO:225), and TFP 32 (SEQ ID NO:208) or a derivative or fragment thereof. In one embodiment, the library of nucleic acids comprises six or more (e.g., 8, 10, 12, or 15 or more) of the nucleotide sequences of SEQ ID NOS:30, 32, 34, 36, 38, 40, 42, 44, 46, 62, 64, 66, 68, 70, 85, 87, 89, 91, 130, 132, 134, 136, 138, 140, 176, 178, 180, 182, 184, 186, 201, 203, 205, 207, 209, 220, 222, 224, or 226 or a derivative or fragment thereof.

The term "fragment thereof," as applied to a TFP, refers to a polypeptide comprising of any portion of the amino acid sequence of the TFP, wherein the fragment substantially retains the ability to induce the secretion of a target protein to which it is fused.

The term "derivative thereof," as applied to a TFP, refers to a polypeptide consisting of an amino acid sequence that is at least 70% identical to the amino acid sequence of the TFP, wherein the polypeptide substantially retains the ability to induce the secretion of a target protein to which it is fused. In some embodiments, the derivative comprises an amino acid sequence that is at least 75%, 80%, 85%, 90%, 95%, 96%, 97%, 98%, or 99% identical to the amino acid sequence of the TFP. The derivative may comprise additions, deletions, substitutions, or a combination thereof to the amino acid sequence of the TFP. Additions or substitutions also include the use of non-naturally occurring amino acids.

Preferably, any substitutions are conservative amino acid substitutions. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "derivative thereof," as applied to a nucleic acid encoding a TFP, refers to a nucleic acid consisting of a nucleotide sequence that is at least 70% identical to the nucleotide sequence of the nucleic acid encoding the TFP, wherein the polypeptide encoded by the derivative substantially retains the ability to induce the secretion of a target protein to which it is fused. In some embodiments, the derivative comprises a nucleotide sequence that is at least 75%, 80%, 85%, 90%, 95%, 96%, 97%, 98%, or 99% identical to the nucleotide sequence of the nucleic acid encoding the TFP. The derivative may comprise additions, deletions, substitutions, or a combination thereof to the nucleotide sequence of the nucleic acid encoding the TFP.

Sequence identity is calculated by comparing two optimally aligned sequences over that region of comparison, determining the number of positions at which the identical amino acid residue or nucleotide occurs in both sequences to yield the number of matched positions, dividing the number of matched positions by the total number of positions in the region of comparison (i.e., the window size), and multiplying the result by 100 to yield the percentage of sequence identity. In one aspect, percent identity is calculated as the percentage of amino acid residues or nucleotides in the smaller of two sequences which align with an identical amino acid residue or nucleotide in the sequence being compared, when four gaps in a length of 100 amino acids or nucleotides may be introduced to maximize alignment (Dayhoff, in Atlas of Protein Sequence and Structure, Vol. 5, p. 124, National Biochemical Research Foundation, Washington, D.C. (1972), incorporated herein by reference). A determination of identity is typically made by a computer homology program known in the art. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482-489, which in incorporated herein by reference in its entirety).

Examples of derivatives include, but are not limited to deletion mutants (e.g., unidirectional deletion), addition of functional sequences (e.g., glycosylation sites, restriction enzyme sites), and deletion or addition (e.g., swapping) of pro-sequences or pre-sequences identified within TFPs. One of skill in the art can prepare derivatives of TFPs or nucleic acids encoding TFPs using routine mutagenesis techniques, such as those described in the references cited above, and identify derivatives that substantially retain the ability to induce the secretion of a target protein to which it is fused.

The term "substantially retains the ability to induce the secretion of a target protein to which it is fused," as used herein, refers to a fragment or derivative of a TFP which retains at least 50% of the ability of the parent TFP to induce secretion of a target protein to which it is fused. In some embodiments, at least 60, 65, 70, 75, 80, 85, 90, or 95% of the ability to induce the secretion of a target protein to which it is fused is retained. The ability to induce the secretion of a target protein may be determined by routine techniques well known in the art and described above.

One embodiment of the present invention relates to a library of nucleic acid fragments encoding TFPs, comprising 10 or more nucleic acid fragments (e.g., 50, 100, 500, 100, or 2000 or more) identified by the methods of the invention, wherein a library of pre-selected candidate TFPs was used in the screening.

Another embodiment of the present invention relates to a library of nucleic acid fragments encoding TFPs, comprising 10 or more nucleic acid fragments (e.g., 50 or 100 or more) identified by the methods of the invention, wherein a library of pre-selected candidate TFPs obtained by transforming a plurality of reporter protein-deficient host cells with a variety of vectors comprising a library of nucleic acid fragments and a nucleotide sequence encoding a reporter protein, collecting cells that grow, isolating vectors from the cells, and isolating nucleic acid fragments from the vectors, thereby obtaining a TFP library comprising nucleic acid fragments which individually induce secretion of the reporter protein, was used in the screening.

A further embodiment of the present invention relates to a library of nucleic acid fragments encoding TFPs, comprising 10 or more nucleic acid fragments (e.g., 50, 100, 500, or 1000 or more) identified by the methods of the invention, wherein a library of pre-selected candidate TFPs derived from sequences identified in a genome database by searching for (i) genes containing a pre-secretion signal homologous with those of one or more previously identified TFPs; (ii) genes comprising a secretion signal sequence, or (iii) genes encoding proteins passing through endoplasmic reticulum, was used in the screening.

A further embodiment of the present invention relates to a library of nucleic acid fragments encoding TFPs, comprising 10 or more nucleic acid fragments (e.g., 50, 100, or 500 or more) identified by the methods of the invention, wherein a library of pre-selected candidate TFPs obtained by diversifying previously identified TFPs, was used in the screening.

The present invention further relates to a nucleic acid comprising a nucleotide sequence encoding a TFP identified by the methods of the invention and a nucleotide sequence encoding a target protein. In one embodiment, the TFP is selected from the group consisting of TFP-9, TFP-13, TFP-17, TFP-18, TFP-19, TFP-20, TFP-21, TFP-25, TFP-27, TFP-11, TFP-22, TFP-29, TFP-34, TFP-38, TFP-39, TFP-43, TFP-44, TFP-48, TFP-52, TFP-54, TFP-40, TFP-50, TFP-51, TFP-57, TFP-58, TFP-59, TFP-5, TFP-6, TFP-7 and TFP-8 or a derivative or fragment thereof. In another embodiment, the target protein is selected from IL-2, IL-32, human growth hormone and human caspase-1 subunit P10. In a particular embodiment, the TFP is TFP-9, TFP-13, TFP-17, TFP-18, TFP-19, TFP-20, TFP-21, TFP-25, TFP-27, PpTFP-1, PpTFP-2, PpTFP-3, PpTFP-4 or a derivative or fragment thereof, and the target protein is IL-2. In another embodiment, the TFP is TFP-1, TFP-22, TFP-29, TFP-34 or TFP-38 or a derivative or fragment thereof, and the target protein is IL-32 alpha. In a further embodiment, the TFP is TFP-9, TFP-13, TFP-17, TFP-18, TFP-19, TFP-20, TFP-21, TFP-25, TFP-27, TFP-11, TFP-22, TFP-29, TFP-34 or TFP-38 or a derivative or fragment thereof, and the target protein is growth hormone.

The present invention further relates to methods of recombinantly producing a target protein using the TFPs of the invention. In one embodiment, the method comprises preparing a vector comprising a nucleotide sequence encoding a target protein operably linked to a nucleotide sequence encoding a TFP or a derivative or fragment thereof, transforming a host cell with the vector, and culturing the host cell under conditions in which the target protein is produced and secreted from the host cell. In one embodiment, the TFP is selected from the group consisting of TFP-9 (SEQ ID NO:29), TFP-13 (SEQ ID NO:31), TFP-17 (SEQ ID NO:33), TFP-18 (SEQ ID NO:35), TFP-19 (SEQ ID NO:37), TFP-20 (SEQ ID NO:39), TFP-21 (SEQ ID NO:41), TFP-25 (SEQ ID NO:43), TFP-27 (SEQ ID NO:45), TFP-11 (SEQ ID NO:61), TFP-22 (SEQ ID NO:63), TFP-29 (SEQ ID NO:65), TFP-34 (SEQ ID NO:67), TFP-38 (SEQ ID NO:69), TFP-39 (SEQ ID NO:129), TFP-43 (SEQ ID NO:131), TFP-44 (SEQ ID NO:133), TFP-48 (SEQ ID NO:135), TFP-52 (SEQ ID NO:137), TFP-54 (SEQ ID NO:139), TFP-40 (SEQ ID NO:175), TFP-50 (SEQ ID NO:177), TFP-51 (SEQ ID NO:179), TFP-57 (SEQ ID NO:181), TFP-58 (SEQ ID NO:183), TFP-59 (SEQ ID NO:185), TFP-5 (SEQ ID NO:200), TFP-6 (SEQ ID NO:202), TFP-7 (SEQ ID NO:204), TFP-8 (SEQ ID NO:206), PpTFP-1 (SEQ ID NO:84), PpTFP-2 (SEQ ID NO:86), PpTFP-3 (SEQ ID NO:88), and PpTFP-4 (SEQ ID NO:90) or a derivative or fragment thereof. In a further embodiment, the target protein is selected from IL-2, IL-32, human growth hormone and human caspase-1 subunit P10.

The target protein may be recombinantly produced using any expression system known in the art. Preferably, the target protein is recombinantly expressed, e.g., in bacterial, yeast, or mammalian cell cultures. Recombinant expression involves preparing a vector comprising a polynucleotide encoding the target protein, delivering the vector into a host cell, culturing the host cell under conditions in which the target protein is expressed, and separating the target protein. Methods and materials for E preparing recombinant vectors and transforming host cells using the same, replicating the vectors in host cells and expressing biologically active foreign polypeptides and proteins are discussed above and described in Sambrook et al., Molecular Cloning, 3rd edition, Cold Spring Harbor Laboratory, 2001 and Ausubel et al., Current Protocols in Molecular Biology, John Wiley & Sons, New York 3rd edition, (2000), each incorporated herein by reference.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g. resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the target protein or can be introduced on a separate vector. Cells stably transfected with the introduced nucleic acid can be identified by drug selection (e.g., cells that have incorporated the selectable marker gene will survive, while the other cells die).

The target protein may be isolated from the medium in which the host cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

If the isolated target protein is not biologically active following the isolation procedure employed, various methods for "refolding" or converting the polypeptide to its tertiary structure and generating disulfide linkages, can be used to restore biological activity. Methods known to one of ordinary skill in the art include adjusting the pH of the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. It may be required to employ a reducing agent or the reducing agent plus its oxidized form in a specific ratio, to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, 2-mercaptoethanol (bME)/dithio-b(ME). To increase the efficiency of the refolding, it may be necessary to employ a cosolvent, such as glycerol, polyethylene glycol of various molecular weights, and arginine.

In one embodiment, the present invention relates to a linear vector comprising a nucleic acid fragment from a library of nucleic acid fragments and a nucleotide sequence encoding a N-terminal amino acid-deleted reporter protein. In another embodiment, the linear vector further comprises a target protein-encoding nucleotide sequence.

The present invention further relates to a plurality of reporter protein-deficient host cells transformed with a library of linear vectors of the invention. In one embodiment, the host cells are further transformed with a nucleic acid encoding a target protein.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Preparation of Invertase-Deficient Yeast Mutant

For rapid screening of the translational fusion partners (TFP) of non-producible proteins, an automatic screening system was established through the evaluation of cell growth in a sucrose medium using yeast invertase as a reporter.

Figure 1:
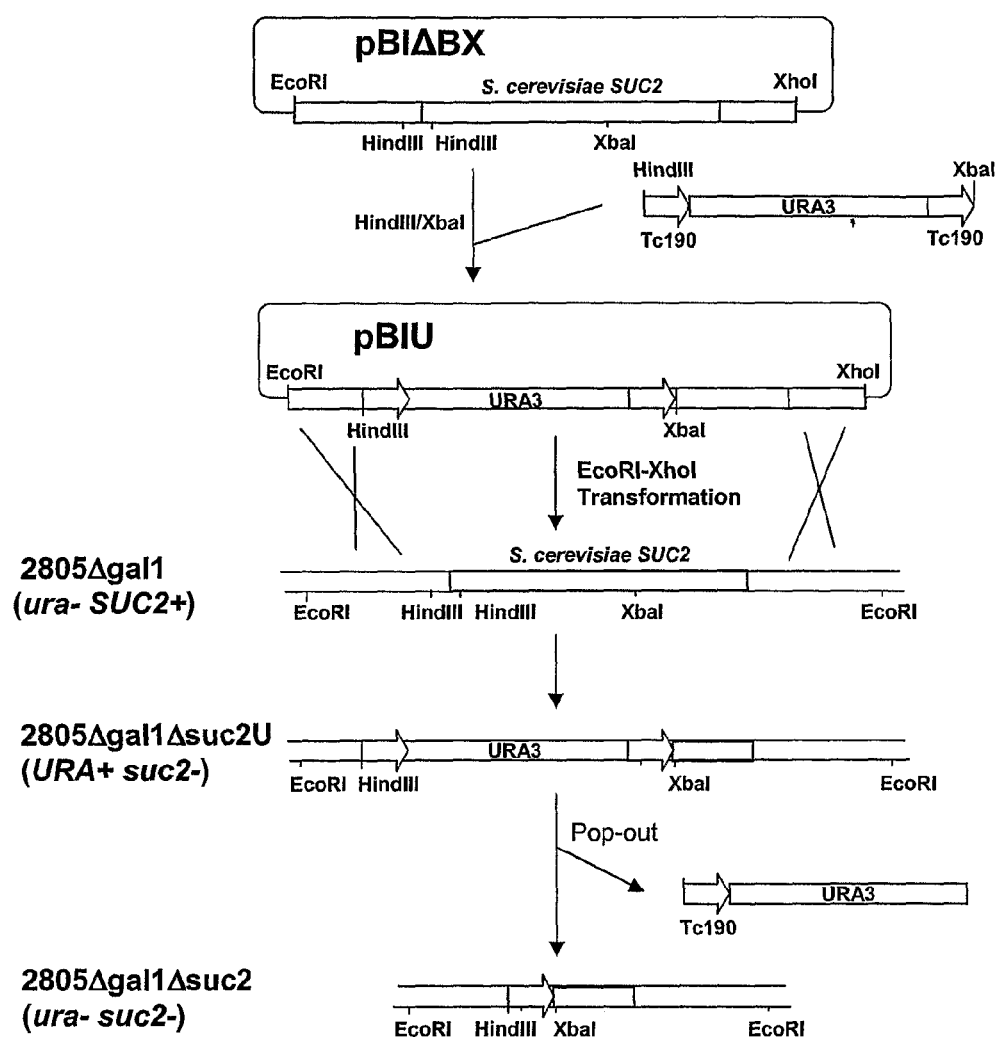

A yeast strain having no invertase activity was required to use an invertase gene as a reporter for the positive screening of useful TFP. Thus, the chromosomal SUC2 gene of wild type yeast was deleted. In order to prepare a SUC2 deletion cassette, a plasmid pRB58 (Carlson et al., Cell 20:145 (1982)) was digested with EcoRI and XhoI, and a SUC2 coding gene was recovered and introduced into EcoRI-XhoI sites of pBluescript KS+ (Stratagene, USA), thus generating pBIΔBX. As shown in FIG. 1, an URA3 gene having a repeat sequence of 190 bp (Tc190) (Bae et al., Yeast 21:437 (2004)) at both ends was inserted into HindIII-XbaI sites of the SUC2 gene contained in pBIΔBX, thus generating pBIU. The pBIU was digested with EcoRI and XhoI, and was transformed into S. cerevisiae Y2805 (Mat a ura3 SUC2 pep4::HIS3 GAL1 can1) and Y2805Δgal1 (Mat a ura3 SUC2 pep4::HIS3 gal1 can1) strain (SK Rhee, Korea Research Institute of Bioscience and Biotechnology) according to a lithium acetate method (Hill et al., Nucleic Acids Res. 19:5791 (1991)). The transformants, Y2805Δsuc2U (Mat a suc2::URA3 pep4:: HIS3 GAL1 can1), Y2805Δgal1Δsuc2U (Mat a suc2::URA3 pep4::HIS3 gal1 can1), were selected in a selection medium lacking uracil.

Figure 2:
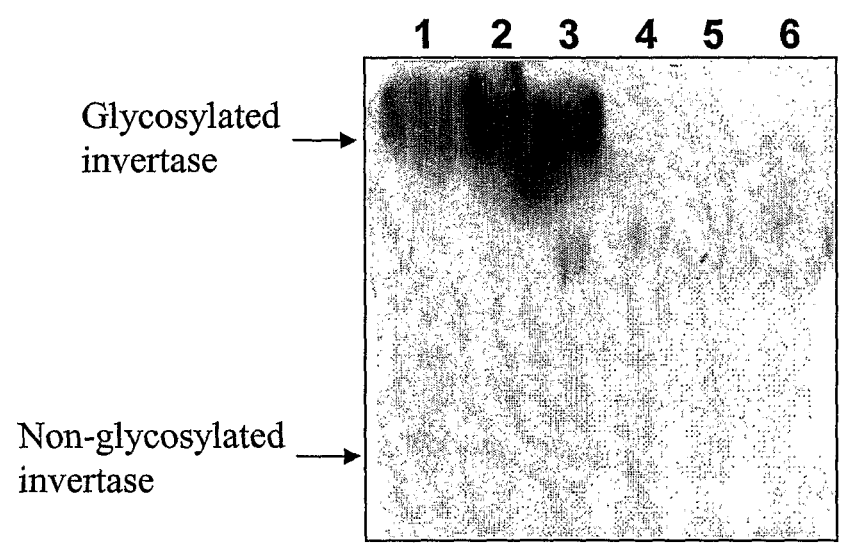
Figure 3:
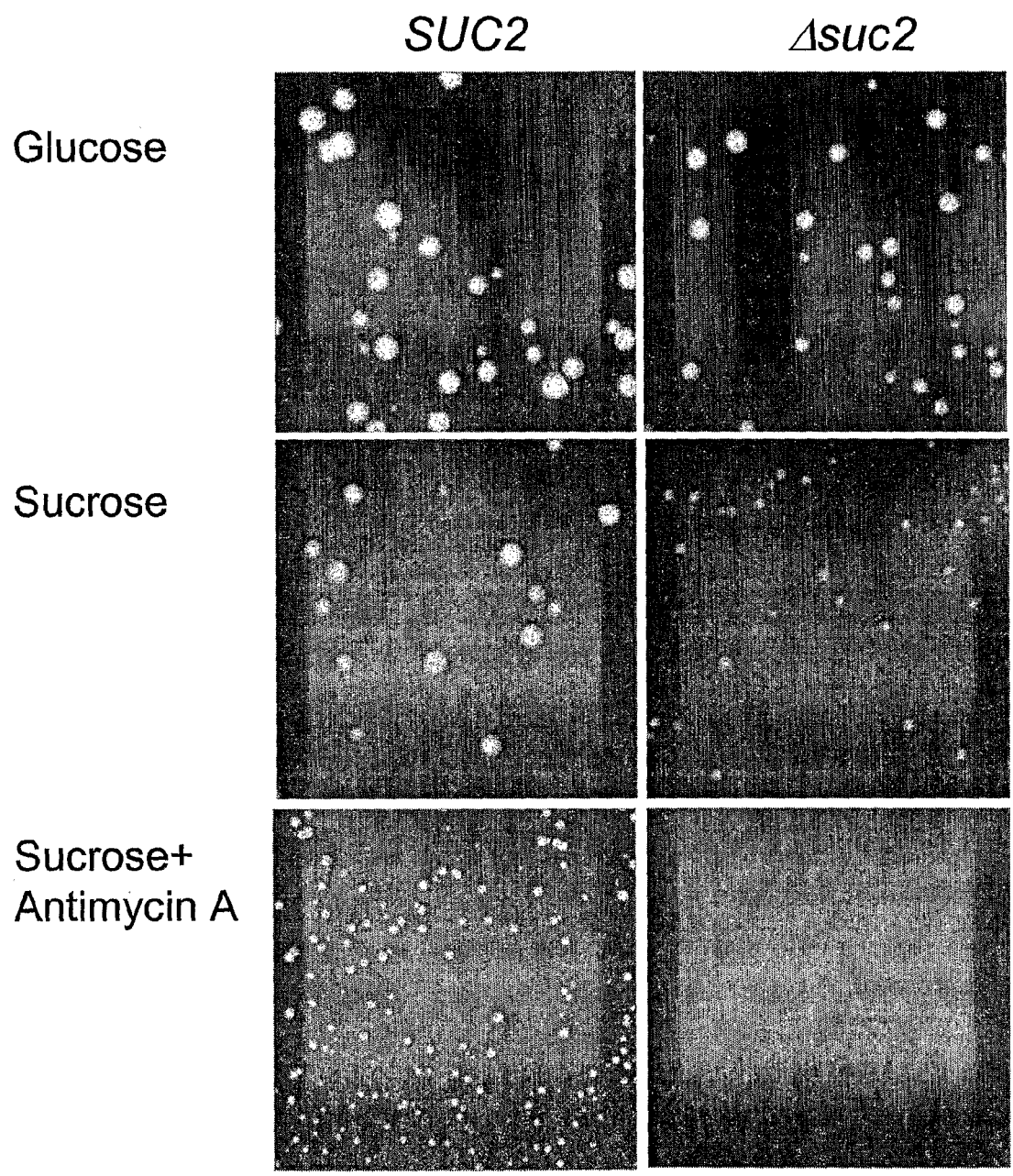

To evaluate the invertase activity of the transformed cells, a single colony was cultured in two media containing glucose and sucrose, respectively, as the sole carbon source. As a result, the colonies grew normally in the glucose medium, but grew very slowly in the sucrose medium compared to a control. In order to investigate the amount of invertase secreted into the culture medium, the SUC2+ strain and the Δsuc2 strain were cultured on YPD media (1% yeast extract, 2% Bacto-peptone and 2% glucose). Proteins contained in the culture supernatants were separated by SDS-PAGE, and the gel was incubated in a sucrose solution for 30 min and subjected to zymogram analysis using a dye, TTC (2,3,5-triphenyl-tetrazolium chloride). As shown in FIG. 2, the Δsuc2 strain was found to lose most of its invertase activity. However, the mutant strain had a problem of growing even at very slow rates in the sucrose medium. This is believed to be because cells partially grow by gluconeogenesis through the function of mitochondria. Thus, to solve this problem, antimycin A, an inhibitor of mitochondrial electron transport, was added to the medium to block cell growth. As a result, the growth of the mutant strain was completely inhibited in the YPSA (1% yeast extract, 2% Bacto-peptone, 2% sucrose, 1 μg/ml antimycin A, and 2% agar) or YPSGA (1% yeast extract, 2% Bacto-peptone, 2% sucrose, 1 μg/ml antimycin A, and 2% agar) medium containing antimycin A (FIG. 3).

Figure 4:
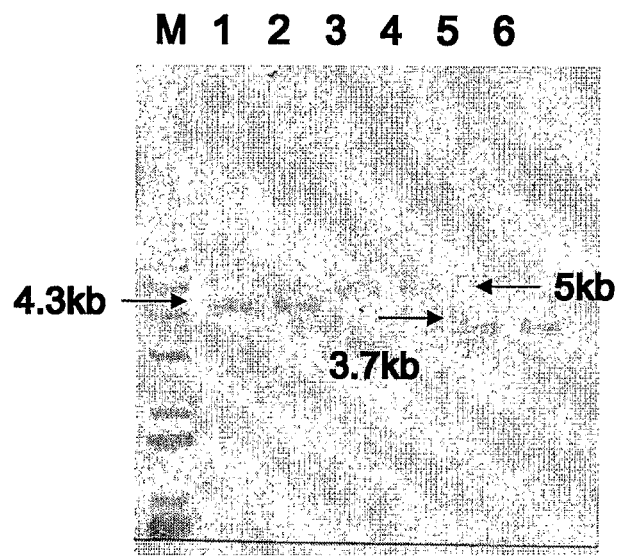

In order to recover uracil auxotrophy of the selected strain, Y2805Δsuc2U (Mat a suc2::URA3 pep4::HIS3 GAL1 can1) and Y2805Δgal1Δsuc2U (Mat a suc2:: URA3 pep4::HIS3 gal1 can1), with a URA3 vector containing a TFP library, it was necessary to remove the URA3 gene which was used for the deletion of the SUC2 gene. To do this, cells were cultured in a medium containing 5-fluoroorotic acid (5-FOA) and selected for loss of the URA3 gene, thus obtaining URA3 pop-out strains, Y2805Δsuc2 (Mat a ura3 suc2::Tc190 pep4:: HIS3 GAL1 can1) and Y2805Δgal1Δsuc2 (Mat a ura3 suc2:: Tc190 pep4::HIS3 gal1 can1) (FIG. 1). Southern blotting was carried out to confirm the deletion of the SUC2 gene on the chromosome, as expected, and the URA3 gene was deleted (popped-out) from the integration locus (FIG. 4). When chromosomal DNA from S. cerevisiae Y2805 was treated with EcoRI and analyzed by Southern blotting using a SUC2 gene as a probe, a fragment of about 4.3 kb was detected. This size increased to about 5.0 kb when a URA3 gene was inserted (Y2805Δgal1Δsuc2U), and decreased to about 3.7 kb when the URA3 gene was popped-out (Y2805Δgal1Δsuc2). As shown in FIG. 4, as expected, the SUC2 gene was obviously deleted, and the URA3 gene was lost (popped-out).

EXAMPLE 2

Development of Automatic Screening System Using an Invertase as a Secretion Reporter The invertase deficient strain was evaluated for the possibility of being automatically screened in a sucrose medium through the expression of a protein fused to invertase, using two human therapeutic proteins, a human serum albumin (HSA) which is well secreted in yeast, and a human interleukin-2 (IL-2) which is hardly secretable in yeast.

Three plasmids, pYGAP-SNS-SUC2, pYGAP-HSA-SUC2 and pYGAP-hIL2-SUC2, were constructed to test for automatic selection on sucrose media. For the construction of pYGAP-SUC2 containing an invertase, gene (SUC2, YIL162W) expression cassette under the control of the yeast GAPDH promoter, pST-SUC2 was constructed first by subcloning a PCR product containing SUC2 gene amplified from pBIΔBX (FIG. 1) using primers SUC-F (SEQ ID NO. 1) and SUC-R (SEQ ID NO. 2) into pST-Blue-1 (Novagen, USA). PCR was carried out with Pfu polymerase (Stratagene, USA) or Ex-Taq DNA polymerase (TaKaRa Korea Biomedical Inc., Seoul, Korea). PCR conditions included one cycle of 94° C. for 5 min, and 25 cycles of 94° C. for 30 sec, 55° C. for 30 sec and 72° C. for 2 min, followed by one final cycle of 72° C. for 7 min. The EcoRI-SalI fragment containing SUC2 from pST-SUC2 was subcloned into EcoRI-SalI digested YGAPα-HIR harboring a GAPDH promoter instead of the GAL10 promoter of YEGα-HIR525 (Sohn et al., Process Biochem. 30:653 (1995)), and the resulting plasmid was named pYGAP-SUC2. To facilitate the fusion of foreign genes with SUC2 and induce in vivo cleavage of the fused proteins by yeast dipeptidyl protease Kex2p (Mizuno K et al., Biochem. Biophys. Res. Commun. 156:246 (1988)) during secretion, an artificial sequence for two SfiI and a NotI recognition sites and a sequence coding for Kex2p cleavage site (Leu-Asp-Lys-Arg (SEQ ID NO:214)) were in-frame added between a secretion signal sequence (19 amino acids) and a SUC2 mature sequence (513 amino acids) of SUC2 by PCR. Two PCR fragments, PCR-A containing a GAPDH promoter and a SUC2 secretion signal sequence amplified using primers GAP-F (SEQ ID NO:3) and SUCSS-R (SEQ ID NO:4) and PCR-B containing a mature part of SUC2 amplified from pYGAP-SUC2 using primers SUCM-F (SEQ ID NO:5) and SUC-R (SEQ ID NO:2) were amplified from pYGAP-SUC2, respectively. Both fragments were subcloned into pST-Blue-1 and recovered by SacI-NotI digestion for PCR-A and NotI-SalI digestion for PCR-B. Enzyme digested PCR-A and PCR-B were co-ligated into SacI-SalI digested pYGAP-SUC2 and the resulting plasmid was named pYGAP-SNS-SUC2. For the construction of a plasmid, pYGAP-HSA-SUC2, containing an in-frame fused gene between human serum albumin (HSA) with SUC2, the HSA gene was amplified from pYHSA5 (Kang et al., J. Microbiol. Biotechnol. 8:42 (1998)) using primers HSA-F (SEQ ID NO:6) and HSA-R (SEQ ID NO:7) and subcloned in pST-Blue-1. A SfiI digested DNA containing the HSA gene was subcloned into the SfiI digested pYGAP-SNS-SUC2 vector. The resulting plasmid was named pYGAP-HSA-SUC2. For the construction of a plasmid, pYGAP-hIL2-SUC2, containing an in-frame fused gene between human interleukin-2 (hIL2) with SUC2, the hIL2 gene was amplified from pT7-hIL2 (JK Jung, Korea Research Institute of Bioscience and Biotechnology) using primers IL2-F (SEQ ID NO:8) and IL2-R (SEQ ID NO:9) and subcloned into pST-Blue-1. Then a plasmid pYGAP-hIL2-SUC2 was constructed by the subcloning of a SfiI digested hIL2 fragment into the SfiI digested pYGAP-SNS-SUC2 vector.

Figure 5:
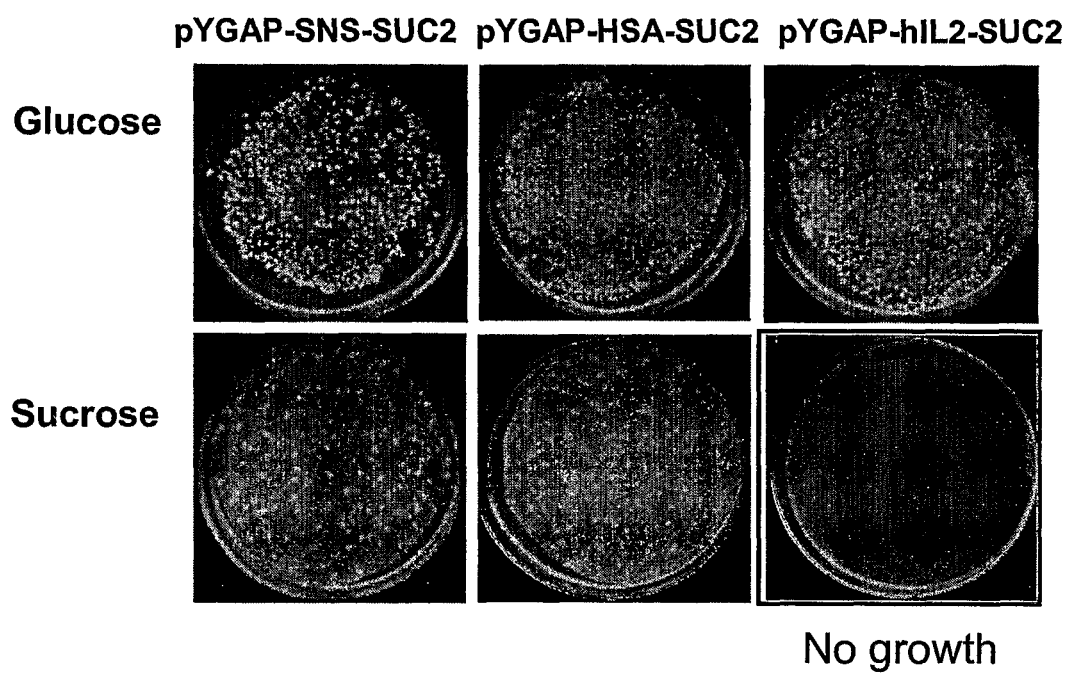

The pYGAP-HSA-SUC2 vector expressing a fusion protein of human serum albumin and invertase, the pYGAP-hIL2-SUC2 expressing a fusion protein of IL-2 and invertase, and the pYGAP-SNS-SUC2 expressing only invertase were individually transformed into a yeast strain (Y2805Δsuc2) which is deleted for its endogenous invertase gene and thus unable to grow in a sucrose medium. The transformed cells were spread onto a UD plate (0.67% yeast nitrogen base without amino acids, 0.77 g/l amino acid mixture, 2% glucose and 2% agar) containing glucose as a sole carbon source and YPSA media (1% yeast extract, 2% Bacto-peptone, 2% sucrose, 1 µg/ml antimycin A, and 2% agar) containing sucrose as a sole carbon source and cell growth of each transformation was observed (FIG. 5). When cells were transformed with pYGAP-SNS-SUC2 expressing invertase, they normally grew in both carbon sources. Similarly, when cells were transformed with pYGAP-HSA-SUC2 having a fusion of HSA at the N-terminus of invertase, they grew well using both carbon sources. In contrast, when cells were transformed with pYGAP-hIL2-SUC2 having a fusion of IL2 instead of HSA, they grew normally on the glucose medium but hardly grew on the sucrose medium. This inability of the pYGAP-hIL2-SUC2-transformed cells to grow in the sucrose medium was believed to be caused by the IL-2 being unable to be secreted from the cells and leading to a block of the secretion of invertase, fused thereto. These results suggested a positive selection system using an invertase as a reporter for a secretion signals and a fusion partner (a translational fusion partner, TFP) from any sources of DNA enhancing the secretion of non- or hardly-secretable proteins such as human IL2.

EXAMPLE 3

Figure 6:
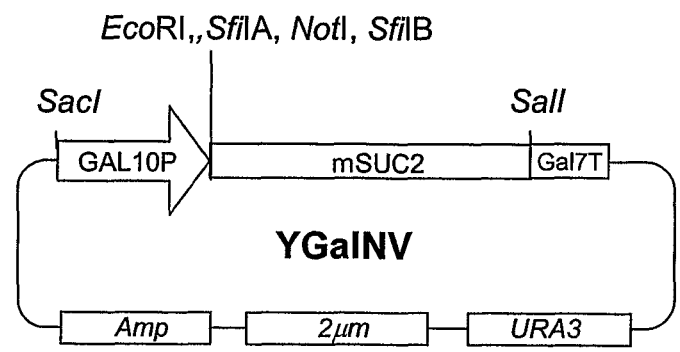
FIG. 6 shows a map of plasmid YGaINV containing multiple cloning sites for the insertion of a cDNA library between the GAL10 promoter and the mature invertase gene.
Figure 7:
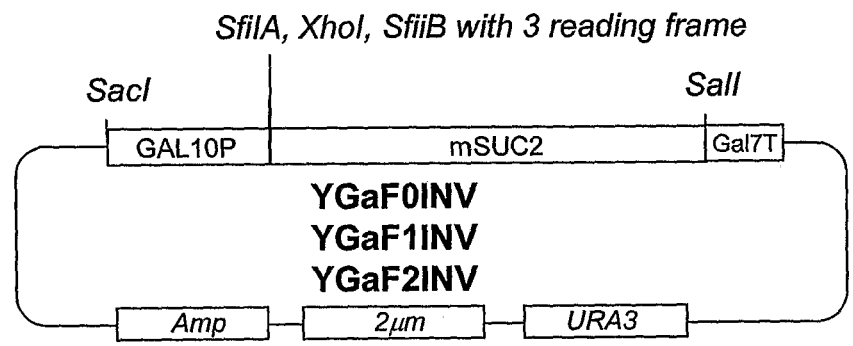
FIG. 7 shows a map of plasmids YGaF0INV, YGaF1INV and YGaF2INV containing multiple cloning sites for the insertion of a genomic DNA library between the GAL10 promoter and the mature invertase gene with three different reading frames.

Preparation of Vectors for the Construction of Translational Fusion Partner (TFP) Library Several vectors were designed for the construction of a TFP library from genomic DNA or a cDNA library from any source. For the construction of a TFP library from cDNA, a plasmid YGaINV was constructed (FIG. 6). A PCR was carried out to amplify a DNA fragment encoding invertase from pYGAP-hIL2-SUC2 using two PCR primers, SfiI-SUC-F (SEQ ID NO:10) and SUC-Xho-R (SEQ ID NO:11). PCR conditions included one cycle of 94° C. for 5 min, and 25 cycles of 94° C. for 30 sec, 55° C. for 30 sec and 72° C. for 2 min, followed by one final cycle of 72° C. for 7 min. Then an EcoRI-SalI digested PCR fragment was ligated to EcoRI-SalI digested YEGα-HIR525 and the resulting plasmid was named YGaINV (FIG. 6). For the construction of a TFP library from partially digested genomic DNA, three vectors, YGaF0INV, YGaF1INV and YGaF2INV, each containing one of three different reading frames of the SUC2 gene were constructed (FIG. 7). Three different PCR amplifications were performed from YGaINV as a template using a common forward primer Gal100-F (SEQ ID NO:12) and three reverse primers with different reading frames, Xho-F0-R (SEQ ID NO:13), Xho-F1-R (SEQ ID NO:14), and Xho-F2-R (SEQ ID NO:15). PCR was done using a Pfu polymerase (Stratagene, USA). PCR conditions included one cycle of 94° C. for 5 min, and 25 cycles of 94° C. for 30 sec, 55° C. for 30 sec and 72° C. for 2 min, followed by one final cycle of 72° C. for 7 min. Three PCR fragments, were eluted from agarose gel and digested with SfiI. Then they were subcloned into SfiI digested YGaINV, respectively. Three resulting plasmids were named YGaF0INV, YGaF1INV and YGaF2INV (FIG. 7).

EXAMPLE 4

Construction of cDNA Library Fused to Yeast Invertase

For the construction of a cDNA library, total RNA was isolated from yeast S. cerevisiae Y2805 (Mat a ura3 his3 pep4::HIS3 can1). Yeast cells were cultivated to mid-exponential phase in YPD media (2% yeast extract, 1% Bacto-peptone and 2% glucose). Total RNA was isolated by a method described in Elion et al. (Elion et al., Cell 39:663 (1984)). Purification of poly(A)$^+$ mRNA from the total RNA was carried out using an Oligotex mRNA kit (Qiagen, Germany). cDNA was synthesized from the isolated mRNA using a SMART cDNA synthesis kit (BD Bioscience, USA).

Figure 8:
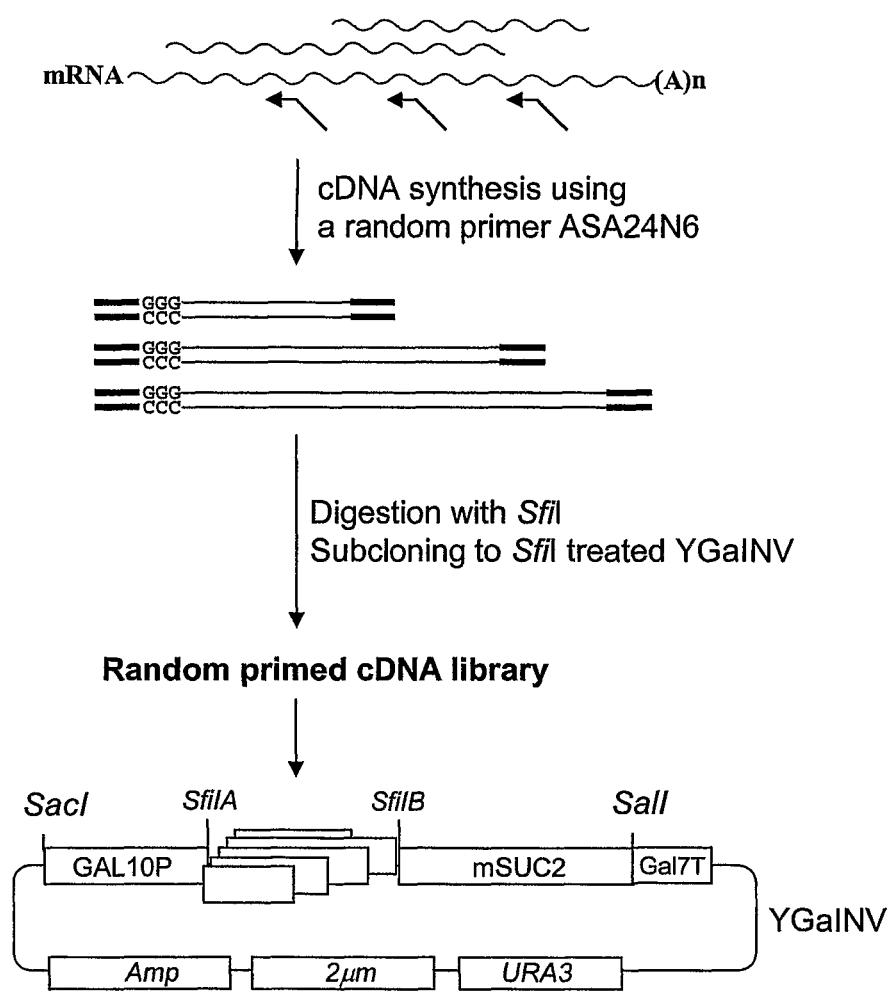
FIG. 8 shows the process of synthesis of a cDNA library with random primer and construction of a cDNA library in the TFP selection vector YGaINV.

A specially designed primer ASA24N6 (SEQ ID NO:16) was used for the synthesis of the first strand cDNA instead of a primer included in the SMART kit. Because the primer ASA24N6 was designed to contain a SfiI recognition site and a random hexameric sequence, it was used for the synthesis of the first strand cDNA from mRNA by reverse transcription as in the method described in the instruction manual of SMART kit (FIG. 8). Primer ASA24N6 could randomly bind to any position of mRNA due to its random hexameric sequence. Thus, most of the first stranded cDNA amplified by using this method contained the 5' partial sequence encoding the N-terminal part of yeast genes. The first stranded cDNA library with 5' partial sequences was used as a PCR template for double stranded cDNA synthesis with the 5' PCR primer of SMART kit (BD Bioscience, USA) and the primer ASA24 (SEQ ID NO:17). The resulting PCR products contained numerous 5' partial fragments of cDNA with SfiI sites at both ends. PCR conditions included one cycle of 95° C. for 20 sec, and 20 cycles of 95° C. for 30 sec, 68° C. for 6 min as recommended in the kit. Amplified cDNA was treated with phenol/chloroform/isoamyl alcohol (25:24:1) and precipitated with 2 volumes of ethanol and 0.1 volume of 3 M sodium acetate (pH 5.0). Recovered cDNA was digested with SfiI at 50° C. for 2 hours and then fractionated using agarose gel electrophoresis. 0.5 to 1 kb DNA was isolated from the gel using a gel extraction kit (Bioneer, Korea). Extracted DNA was ligated into SfiI digested YGaINV vector (FIG. 6) and transformed into *E. coli* DH5α. Transformed *E. coli* was plated on LB media containing ampicillin (1% Bacto-peptone, 0.5% yeast extract, 1% NaCl with 50 µg/ml ampicillin) and incubated at 37° C. overnight. About $5 \times 10^4$ *E. coli* colonies were pooled with sterile distilled water and the total plasmids containing random primed cDNA library fused to the SUC2 gene were isolated by using a plasmid isolation kit (Bioneer, Korea).

EXAMPLE 5

Construction of Genomic DNA Library Fused to Yeast Invertase

Figure 9:
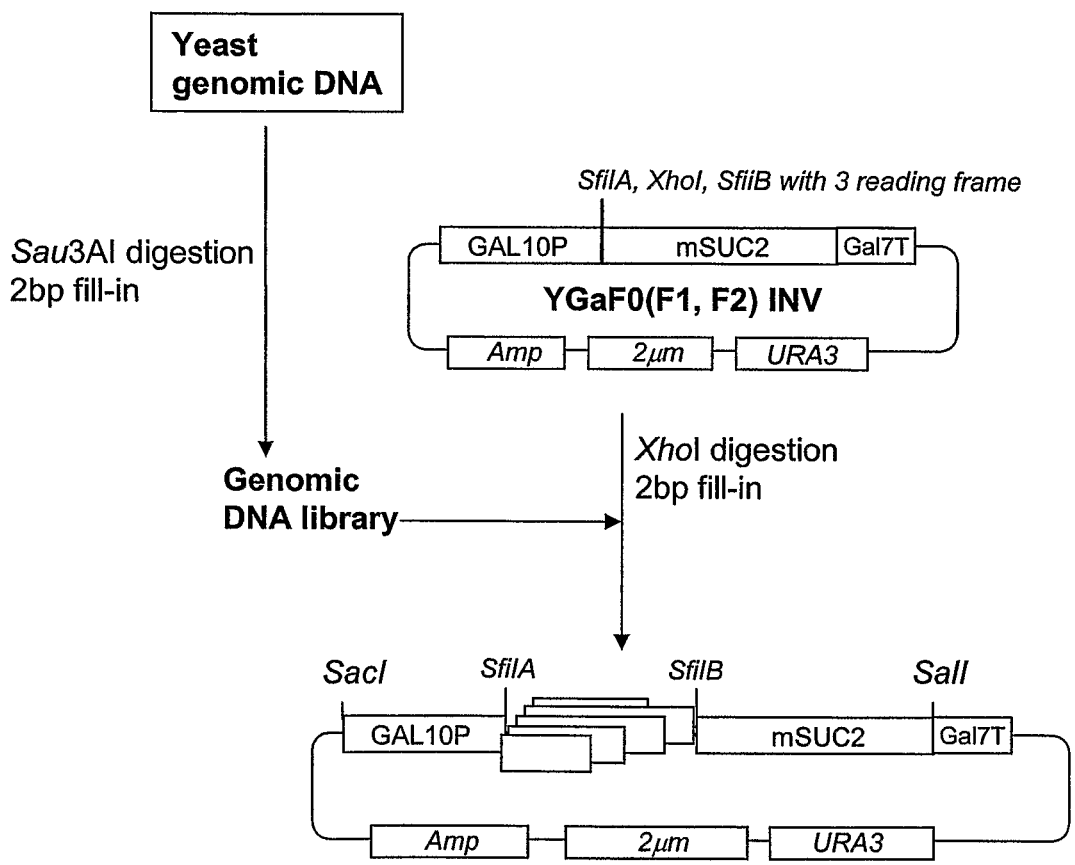
FIG. 9 shows the process of construction of a genomic DNA library in the TFP selection vectors YGaF0INV, YGaF1INV, and YGaF2INV.

The TFP library constructed in Example 4 was obtained from a cDNA library which were synthesized from a pool of mRNA. Because the mRNA of a highly expressed gene is usually abundant compared to that of a poorly expressed gene, a TFP library could be biased with those from highly expressed genes. Furthermore, some genes are completely repressed at a point of the growth phase and thus, they could not be amplified in a TFP library even though they were good candidates for a TFP. To solve such problems, genomic DNA was also used for the construction of a TFP library. As shown in FIG. 9, genomic DNA of *S. cerevisiae* Y2805 was partially digested with Sau3AI and incubated at 70° C. for 10 min to inactivate the enzyme. The DNA was 2 bases filled with Klenow fragment and 0.2 mM of dTTP and dCTP at 25° C. for 1 hour and then 0.5 to 1 kb DNA was isolated from an agarose gel. In addition, vectors YGaF0INV, YGaF1INV and YGaF2INV (FIG. 7) were digested with XhoI. After inactivation of the enzyme at 70° C. for 10 min, the vectors were also 2 bases filled with Klenow fragment and 0.2 mM of dTTP and dCTP and purified from an agarose gel. Each vector was ligated with the partially digested genomic DNA and transformed into *E. coli* DH5α, respectively. Transformed *E. coli* was plated on LB media containing ampicillin (1% Bacto-peptone, 0.5% yeast extract, 1% NaCl with 50 µg/ml ampicillin) and incubated at 37° C. overnight. About $2 \times 10^5$ *E. coli* colonies obtained from three different vectors were pooled with sterile distilled water and the total plasmids containing genomic DNA library fused to the SUC2 gene were isolated by using a plasmid isolation kit (Bioneer, Korea).

EXAMPLE 6

Construction of TFP Library Secreting Invertase

For the first selection of a TFP library secreting invertase from the genomic and cDNA libraries constructed in Example 4 and 5, library DNA was transformed into *S. cerevisiae* Y2805Δgal1Δsuc2(Mat a ura3 suc2::Tc190 pep4:: HIS3 gal1 can1) according to a lithium acetate method (Hill et al., *Nucleic Acids Res.* 19:5791 (1991)). Y2805Δgal1Δsuc2 cannot use sucrose and galactose as carbon sources due to the deletion of both genes. Transformed cells were spread on both UD media (0.67% yeast nitrogen base without amino acids, 0.77 g/l amino acid mixture, 2% glucose and 2% agar) and YPSGA media (1% yeast extract, 2% Bacto-peptone, 2% sucrose, 0.3% galactose, 1 µg/ml antimycin A, and 2% agar) and incubated at 30° C. for 4 to 6 days. Around 3,000 and 1,000 transformants were obtained from the cDNA and genomic DNA library, respectively. All transformants grown on YPSGA media were transferred to a UD plate with a toothpick and incubated at 30° C. for 2 days. Total DNA was isolated from the pooled cells using glass beads and then the DNA was precipitated with ethanol. To recover the plasmid containing TFP library, total DNA was retransformed into *E. Coli* DH5α. Transformed *E. coli* was plated on LB media containing ampicillin (1% Bacto-peptone, 0.5% yeast extract, 1% NaCl with 50 µg/ml ampicillin) and incubated at 37° C. overnight. Around $2 \times 10^4$ *E. coli* transformants were obtained and collected with sterile distilled water for the isolation of total plasmids using a plasmid isolation kit (Bioneer, Korea). Thus, a TFP pool containing up to 4,000 TFPs which individually induce the secretion of invertase was constructed. Nucleotide sequencing of the randomly selected plasmids from the library revealed that all of the TFPs were originated from yeast genes individually encoding different secretory proteins.

EXAMPLE 7

Figure 10:
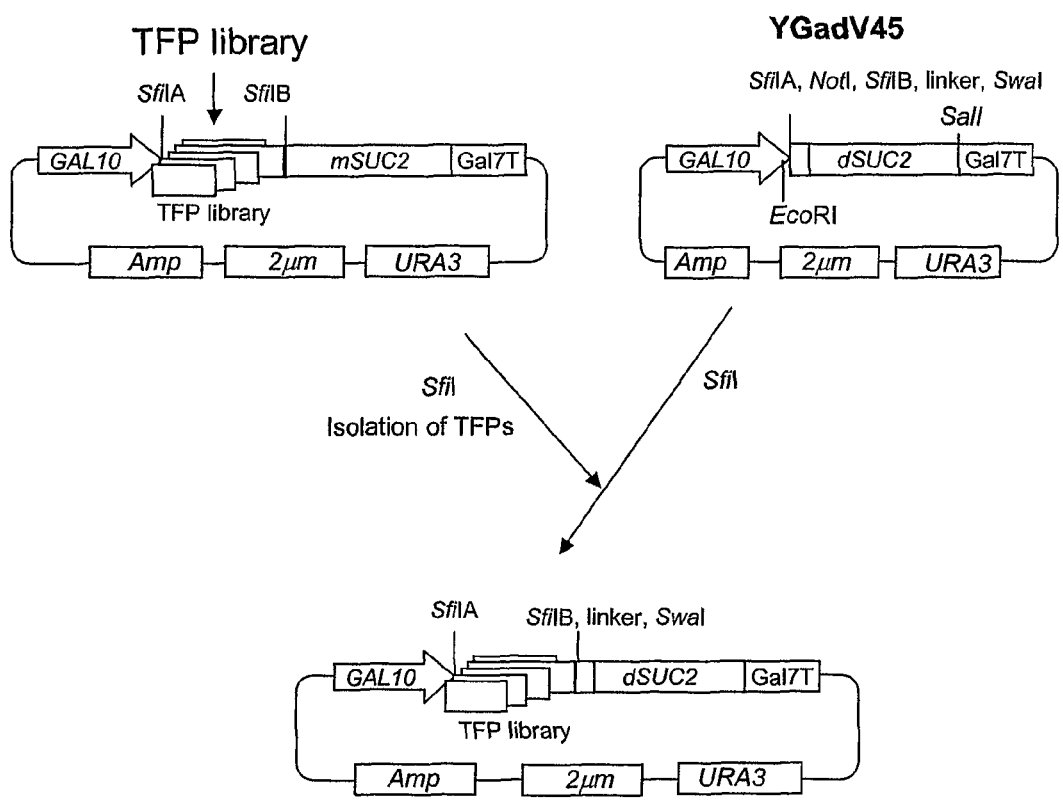
FIG. 10 shows the plasmid map of YGadV45 containing a defective SUC2 and subcloning of a TFP library into YGadV45.

Construction of TFP Library Vector Applicable to Many Target Proteins Through In Vivo Recombination Around 4,000 TFPs having a potential to secrete invertase were collected in Example 6. For the development of a TFP library vector which can be easily applicable to any target gene, a simple in vivo recombination system was designed. A vector, YGadV45 (FIG. 10), was first constructed for the in-frame insertion of any target protein gene between the TFP library and the SUC2 gene through in vivo recombination. YGadV45 contains a defective SUC2 (dSUC2) which is an N-terminal 45 amino acid deleted SUC2 and thus, having no invertase activity. The vector was also designed to contain a NotI and two SfiI recognition sequences, a linker sequence as a recombination target and a SwaI recognition sequence in front of the dSUC2 for the simple insertion of a TFP library and target gene through in vivo recombination. A PCR was carried out from a template YGaINV using a forward primer INV45-F (SEQ ID NO:18) and a reverse primer SUC-Xho-R (SEQ ID NO:11) and Pfu polymerase (Stratagene, USA). PCR conditions included one cycle of 94° C. for 3 min, and 25 cycles of 94° C. for 30 sec, 55° C. for 30 sec and 72° C. for 90 sec, followed by one final cycle of 72° C. for 7 min. From the PCR, an N-terminal modified defective SUC2 gene fragment was obtained. A NotI-SalI digested PCR fragment was subcloned into a NotI-SalI digested vector YGaINV (FIG. 6) and the resulting plasmid was named YGadV45 (FIG. 10). For the construction of a TFP library in YGadV45, the TFP library obtained in Example 6 was digested with SfiI and fractionated in an agarose gel. Around 0.5 to 1 kb DNA fragments were isolated from the gel using a gel extraction kit (Bioneer, Korea). Purified DNA was subcloned into SfiI digested YGadV45 (FIG. 10) and transformed into E. coli DH5α. Transformed E. coli was plated on LB media with ampicillin (1% Bacto-peptone, 0.5% yeast extract, 1% NaCl with 50 μg/ml ampicillin) and incubated at 37° C. overnight. Around $5 \times 10^4$ E. coli transformants were collected with sterile distilled water for the isolation of total plasmids. Total plasmids were isolated using a plasmid isolation kit (Bioneer, Korea). The isolated vectors contained TFPs selected in Example 6 fused to a defective SUC2. Thus, transformation of this TFP library vector into S. cerevisiae Y2805Δgal1Δsuc2 (Mat a ura3 suc2::Tc190pep4::HIS3 gal1 can1) gave thousands of transformants on a UD plate (0.67% yeast nitrogen base without amino acids, 0.77 g/l amino acid mixture, 2% glucose and 2% agar) but no transformants on YPSGA media (1% yeast extract, 2% Bacto-peptone, 2% sucrose, 0.3% galactose, 1 μg/ml antimycin A, and 2% agar). Thus, it could greatly reduce the background level of selection on YPSGA media. Only the cells with a vector harboring an in-frame inserted target gene between TFP and SUC2 could grow on YPSGA after correct in vivo recombination. The TFP library vectors contained a rare cutting restriction enzyme SwaI site and a linker sequence between the TFP library and the dSUC2 for linearization and for homologous recombination, respectively.

EXAMPLE 8

Autoselection of an Optimal TFP Secreting a Target Protein from TFP Library

Figure 11:
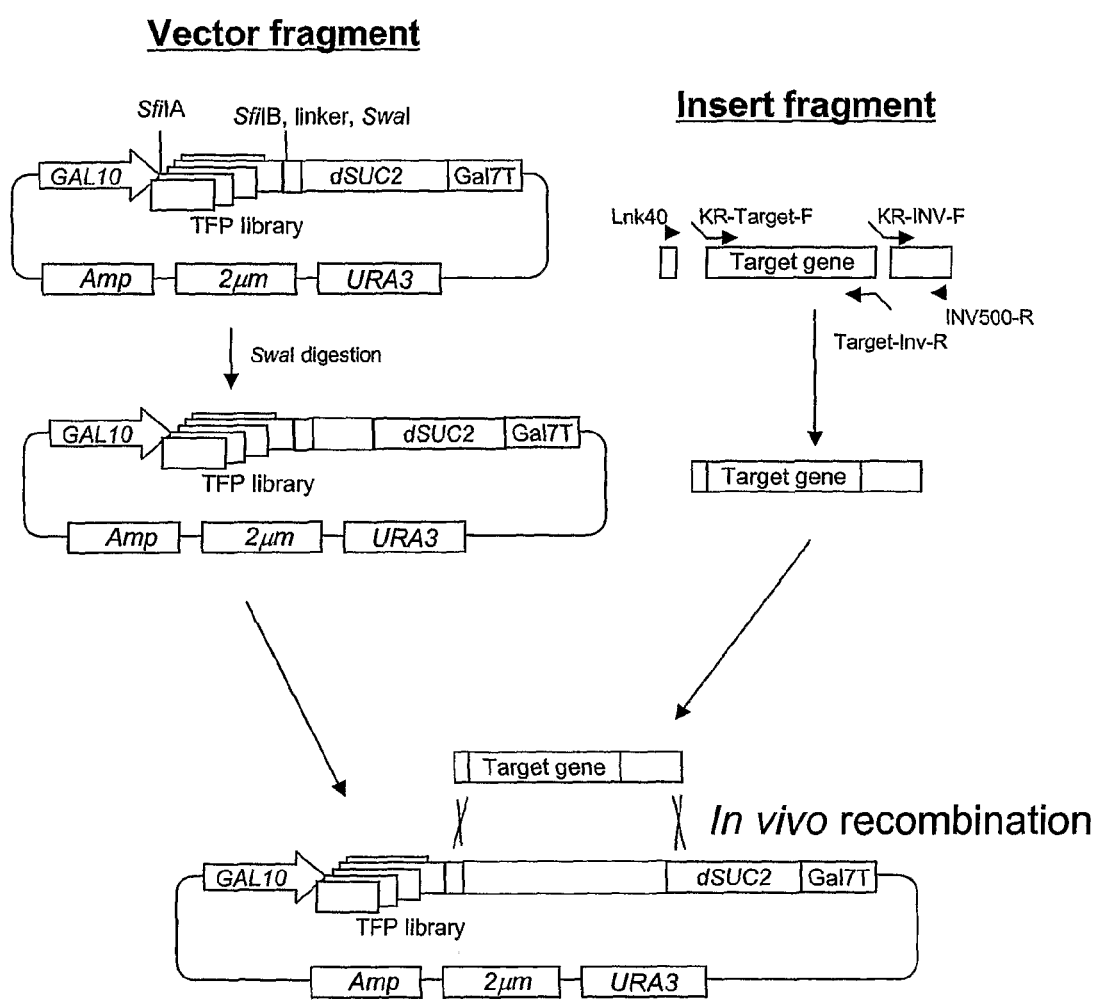
FIG. 11 shows the procedure of TFP selection for a target gene using an invertase as a reporter from a TFP library through in vivo recombination.

For the in-frame fusion of target proteins through in vivo recombination to the TFP library vectors developed in Example 7, a target gene must have a linker DNA in the 5'-end and a N-terminal part of SUC2 in the 3'-end. To add such a sequence to the end of a target gene, overlap extension PCR was used. A first step PCR was carried out for the amplification of a target gene encoding a mature protein using a target specific forward primer KR-target-F (SEQ ID NO:19) and a target specific reverse primer Target-INV-R (SEQ ID NO:20) from a plasmid containing target gene. Separately, another PCR for the amplification of a N-terminal part of SUC2 which will be fused to the 3'-end of a target gene was also carried out using a forward primer KR-Inv-F (SEQ ID NO:21) and a reverse primer Inv500-R (SEQ ID NO:22) from YGaINV (FIG. 6). PCR was performed with Pfu polymerase (Stratagene, USA) and PCR conditions included one cycle of 94° C. for 3 min, and 25 cycles of 94° C. for 30 sec, 55° C. for 30 sec and 72° C. for 90 sec, followed by one final cycle of 72° C. for 7 min. Then a second PCR was done from the two DNA fragments amplified in the first step using a forward primer LNK40 (SEQ ID NO:23) and a reverse primer Inv500-R (SEQ ID NO:22). The resulting fragment (insert fragment) harbored 40 nucleotides of linker DNA in the 5'-end and 500 bp of DNA encoding the Kex2p recognition site (Leu-Asp-Lys-Arg (SEQ ID NO:214)) and a N-terminal part of invertase in the 3'-end, respectively. For in vivo recombination, the insert fragment was mixed at a 2:1 ratio with SwaI digested TFP library vectors constructed in Example 7 and used for transformation into S. cerevisiae Y2805Δgal1Δsuc2 (Mat a ura3 suc2::Tc190 pep4::HIS3 gal1 can1) (FIG. 11). Transformed cells were spread on YPSGA media (1% yeast extract, 2% Bacto-peptone, 2% sucrose, 0.3% galactose, 1 μg/ml antimycin A, and 2% agar) and incubated for 5 days. Only an in-frame fusion of the insert fragment with a vector containing a proper TFP through in vivo recombination could support cell growth on YPSGA media. Thus, using this method, an optimal TFP for any target protein could be retrieved by simple selection of growing cells on YPSGA media.

EXAMPLE 9

Figure 12:
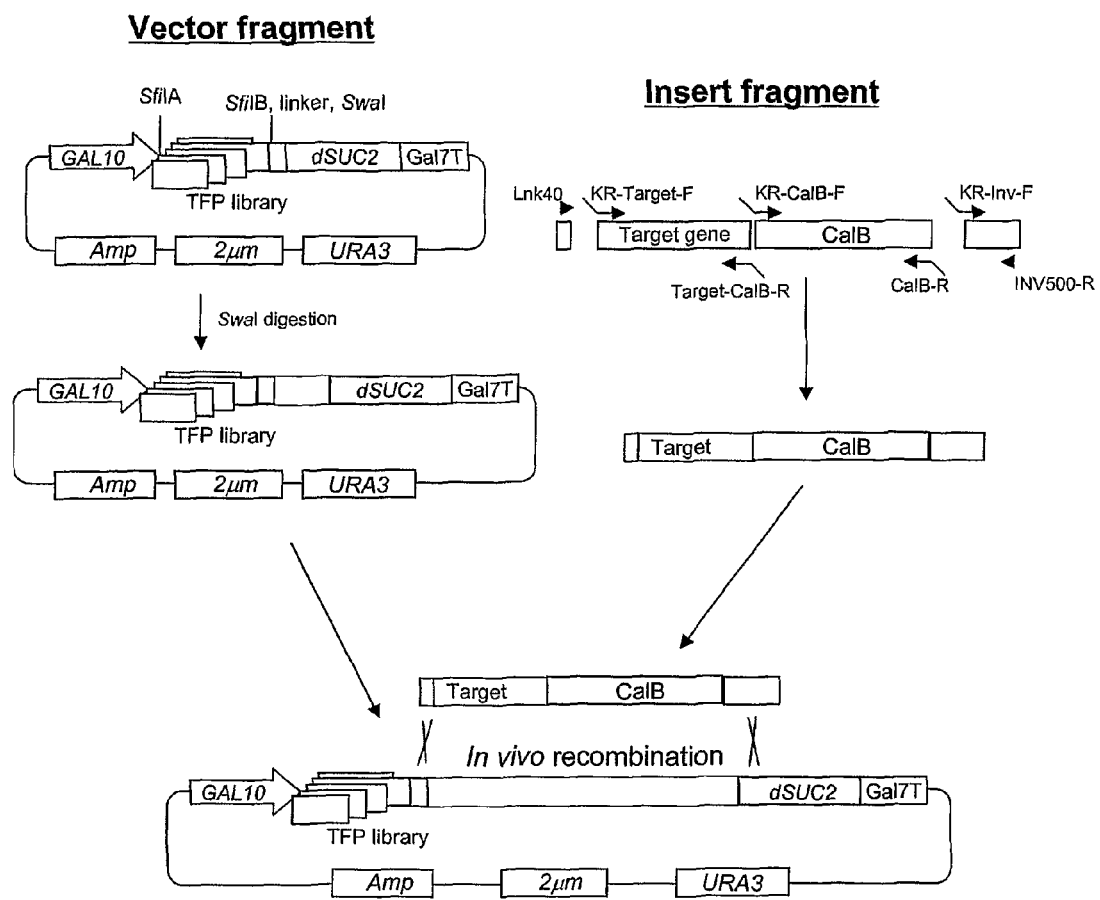
FIG. 12 shows the procedure of TFP selection for a target gene using a double reporter, lipase and invertase, as a reporter from a TFP library through in vivo recombination.
Figure 13:
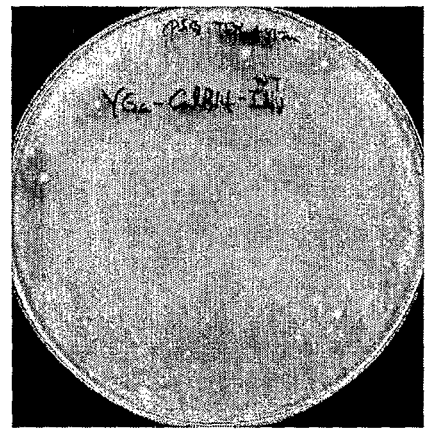
FIG. 13 shows tributyrin plates containing halo forming transformants (A) A halo forming plate (YPSGA with tributyrin) directly from transformation, (B) Selected transformants showing different halo sizes in tributyrin plate.
Figure 13:
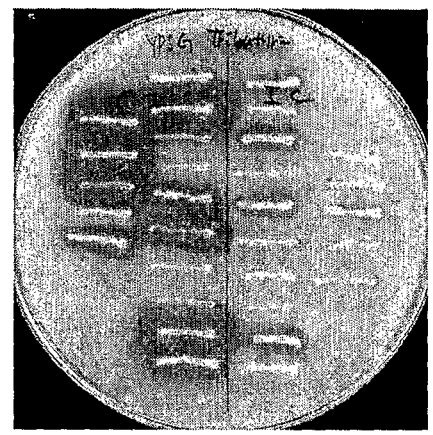

Autoselection of an Optimal TFP Using a Dual Reporter System with Lipase and Invertase An autoselection system using a reporter, invertase, as described in Example 8 was very useful for the screening of an optimal TFP for a target protein such as IL2 which blocks the secretion of invertase completely as found in Example 2. As dozens of colonies could grow on sucrose media, it was easy to select an optimal TFP from the TFP library. Fusion of some target proteins, however, could not completely block the secretion of invertase even though a weak TFP was connected. Such leaky colonies could also grow on sucrose media. Thus, considerable number of colonies should be tested for their secretion level to select an optimal TFP. To solve such a time-consuming problem, a simple selection method was developed to identify a colony having a high protein secretion level with a halo-forming reporter, lipase, on a tributyrin-containing plate. A gene encoding lipase (CalB, lipase B of Candida antarctica) was in-frame fused to the 5' end of invertase. Using this dual reporter system, transformants could be selected with both invertase and lipase activity on YPSGA media containing tributyrin, simultaneously. Colonies secreting protein at a high level could be simply determined with the size of halo formed around the colonies. As shown in FIG. 12, construction of a dual reporter was done by three steps of PCR. A 1 kb PCR fragment containing CalB was first amplified using a CalB forward primer KR-CalB-F (SEQ ID NO:24) and a reverse primer CalB-Inv-R (SEQ ID NO:25) from a plasmid pLGK-Lip14* containing a mutant CalB gene (S Y Kim, Ph.D. thesis, Yonsei University, Korea, 2001). Separately, a 0.5 kb PCR fragment containing a 5' partial SUC2 gene was amplified from YGaINV (FIG. 6) using a forward primer KR-Inv-F (SEQ ID NO:21) and a reverse primer Inv500-R (SEQ ID NO:22). PCR was performed with Pfu polymerase (Stratagene, USA) and PCR conditions included one cycle of 94° C. for 3 min, and 25 cycles of 94° C. for 30 sec, 55° C. for 30 sec and 72° C. for 90 sec, followed by one final cycle of 72° C. for 7 min. Then, a second PCR was done from the two DNA fragments amplified in the first step using a forward primer KR-CalB-F (SEQ ID NO:24) and a reverse primer Inv500-R (SEQ ID NO:22). Separately, a PCR for a target gene was amplified using primers KR-Target-F (SEQ ID NO:19) and Target-CalB-R (SEQ ID NO:26) from a plasmid containing a target gene as described in Example 8. The third PCR was done using a forward primer LNK40 (SEQ ID NO:23) and a reverse primer Inv500-R (SEQ ID NO:22) from a template mixture of a target gene and CalB fused with a partial SUC2 gene. The resulting DNA fragment (insert fragment) consisted of 40 nucleotides of linker, a target gene, Kex2p cleavage site (Leu-Asp-Lys-Arg (SEQ ID NO:214)), CalB, Kex2p cleavage site (Leu-Asp-Lys-Arg (SEQ ID NO:214)) and 500 bp of 5' partial SUC2 gene in order. For in vivo recombination, PCR amplified insert fragment was mixed at a 2:1 ratio with SwaI digested TFP library vectors constructed in Example 7 and used for transformation into *S. cerevisiae* Y2805Δgal1Δsuc2 (Mat a ura3 suc2::Tc190 pep4::HIS3 gal1 can1). Transformed cells were spread on YPSGA (1% yeast extract, 2% Bacto-peptone, 2% sucrose, 0.3% galactose, 1 µg/ml antimycin A, and 2% agar) for selection with invertase activity and YPSGAT (1% yeast extract, 2% Bacto-peptone, 2% sucrose, 0.3% galactose, 1 µg/ml antimycin A, 1% tributyrin, and 2% agar) for selection with invertase and lipase activities, respectively. The transforming plates were incubated at 30° C. for 5 days. Colonies secreting a target protein, lipase and invertase were formed on both YPSGA and YPSGAT plates. As expected, different sizes of halo were formed around colonies. The size of the halo was comparatively proportional to the secreted lipase activity. Thus, it was easy to select a colony with high secretion level directly from the transforming plate (FIG. 13).

EXAMPLE 10

Novel TFP Selected from TFP Library for the Secretion of Human Interleukin-2

As an example for identifying optimal TFPs using a method developed in this invention, a hardly secretable protein, human interleukin-2 (hIL2) was tried. An insert fragment containing the human IL2 gene and a 500 bp N-terminal part of SUC2 was amplified using PCR as described in Example 8 (FIG. 11). A PCR was carried out using a forward primer KR-IL2-F (SEQ ID NO:27) and a reverse primer IL2-INV-R (SEQ ID NO:28) from pT7-hIL-2 (J K Jung, Korea Research Institute of Bioscience and Biotechnology) as a template. Separately, another PCR for the amplification of an N-terminal part of SUC2 to be fused to the 3'-end of the IL2 gene was also carried out using a forward primer KR-Inv-F (SEQ ID NO:21) and a reverse primer Inv500-R (SEQ ID NO:22) from YGaINV (FIG. 6). Then the second PCR was done from the two DNA fragments amplified in the first step using a forward primer LNK40 (SEQ ID NO:23) and Inv500-R (SEQ ID NO:22). The resulting fragment (insert fragment) harbored a 40 nucleotide linker DNA containing a Kex2p recognition sequence (Leu-Asp-Lys-Arg (SEQ ID NO:214)), IL2, an additional Kex2p recognition sequence, and an N-terminal part of invertase in order. This fragment was co-transformed with the SwaI digested TFP library vector constructed in Example 7 into *S. cerevisiae* Y2805Δgal1Δsuc2 (Mat a ura3 suc2::Tc190 pep4::HIS3 gal1 can1). Transformed cells were spread on both UD media (0.67% yeast nitrogen base without amino acids, 0.77 g/l amino acid mixture, 2% glucose and 2% agar) and YPSGA media (1% yeast extract, 2% Bacto-peptone, 2% sucrose, 0.3% galactose, 1 µg/ml antimycin A, and 2% agar) and incubated at 30° C. for 5 days. Around 2×10⁴ transformants were obtained in UD plates but about 100 transformants were obtained in YPSGA. Thirty randomly selected transformants growing on YPSGA was cultivated on YPD broth. Total DNA was isolated and retransformed into *E. coli* DH5α. Transformed *E. coli* was plated on LB media with ampicillin (1% Bacto-peptone, 0.5% yeast extract, 1% NaCl with 50 µg/ml ampicillin) and incubated at 37° C. overnight. Plasmids were isolated from each *E. coli* transformant using a plasmid extraction kit (Bioneer, Korea). To analyze the sequence of each TFP, a sequencing primer GAL100-F (SEQ ID NO:12) binding to the GAL10 promoter was used for all plasmids containing TFPs. Nucleotide sequences were determined by Genotech Co. (Taejon, Korea) using an automated sequencing unit (ABI Prism 377; PE Biosystems, Foster City, Calif., USA). The sequences were analyzed by a BLAST search of the *Saccharomyces* Genome Database (yeastgenome.org). As a result, nine novel TFPs and a known TFP (TFP-3) (WO 2005/068658) were identified from plasmids isolated from 30 colonies which grew on YPSGA media. The isolated plasmids were named pYHTS-TFP9, pYHTS-TFP13, pYHTS-TFP17, pYHTS-TFP18, pYHTS-TFP19, pYHTS-TFP20, pYHTS-TFP21, pYHTS-TFP25, and pYHTS-TFP27, respectively. The nine novel TFPs are summarized in Table 1.

TABLE 1

Selected TFPs for the secretion of human interleukin-2

| Number of TFP | Yeast ORF | Number of fused amino acids(total) | Signal sequence | SEQ ID for protein | SEQ ID for DNA |
|---|---|---|---|---|---|
| TFP-9 | YGR106C | 217(265) | Pre(24aa) | 29 | 30 |
| TFP-13 | YIL123W | 127(350) | Pre(19aa) | 31 | 32 |
| TFP-17 | YNL190W | 68(204) | Pre(20aa) | 33 | 34 |
| TFP-18 | YBR078W | 199(467) | Pre(20aa) | 35 | 36 |
| TFP-19 | YJL178C | 144(271) | Pre(19aa) | 37 | 38 |
| TFP-20 | YMR307W | 187(559) | Pre(22aa) | 39 | 40 |
| TFP-21 | YOR247W | 55(210) | Pre(19aa) | 41 | 42 |
| TFP-25 | YOR085W | 190(350) | Pre(17aa) | 43 | 44 |
| TFP-27 | YKR042W | 89(450) | Pre(17aa) | 45 | 46 |

EXAMPLE 11

Secretion of Human IL2 Using Selected TFPS

Figure 14:
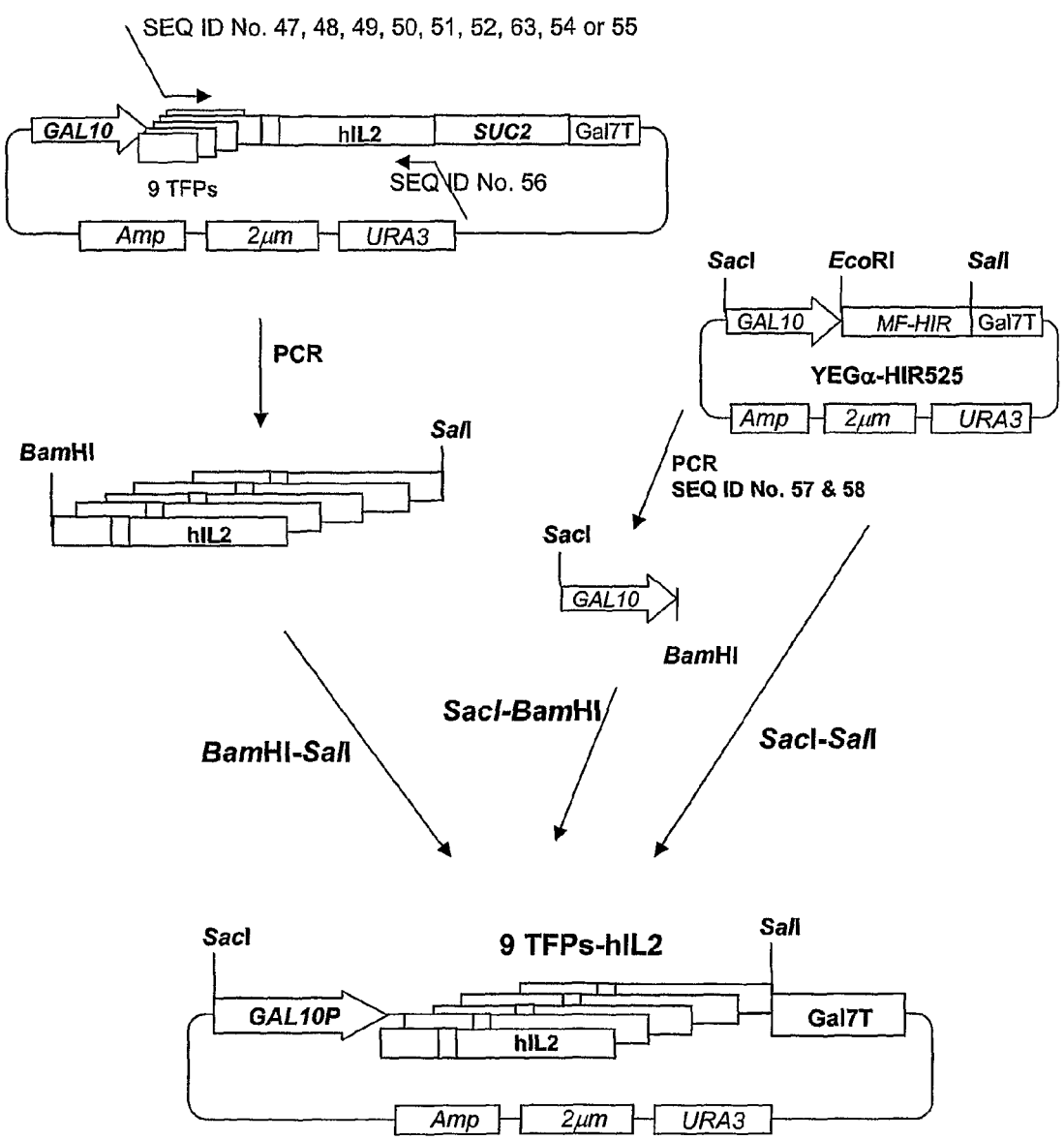
FIG. 14 shows the procedure for the construction of 9 human IL2 expression vectors with 9 selected TFPs.
Figure 15:
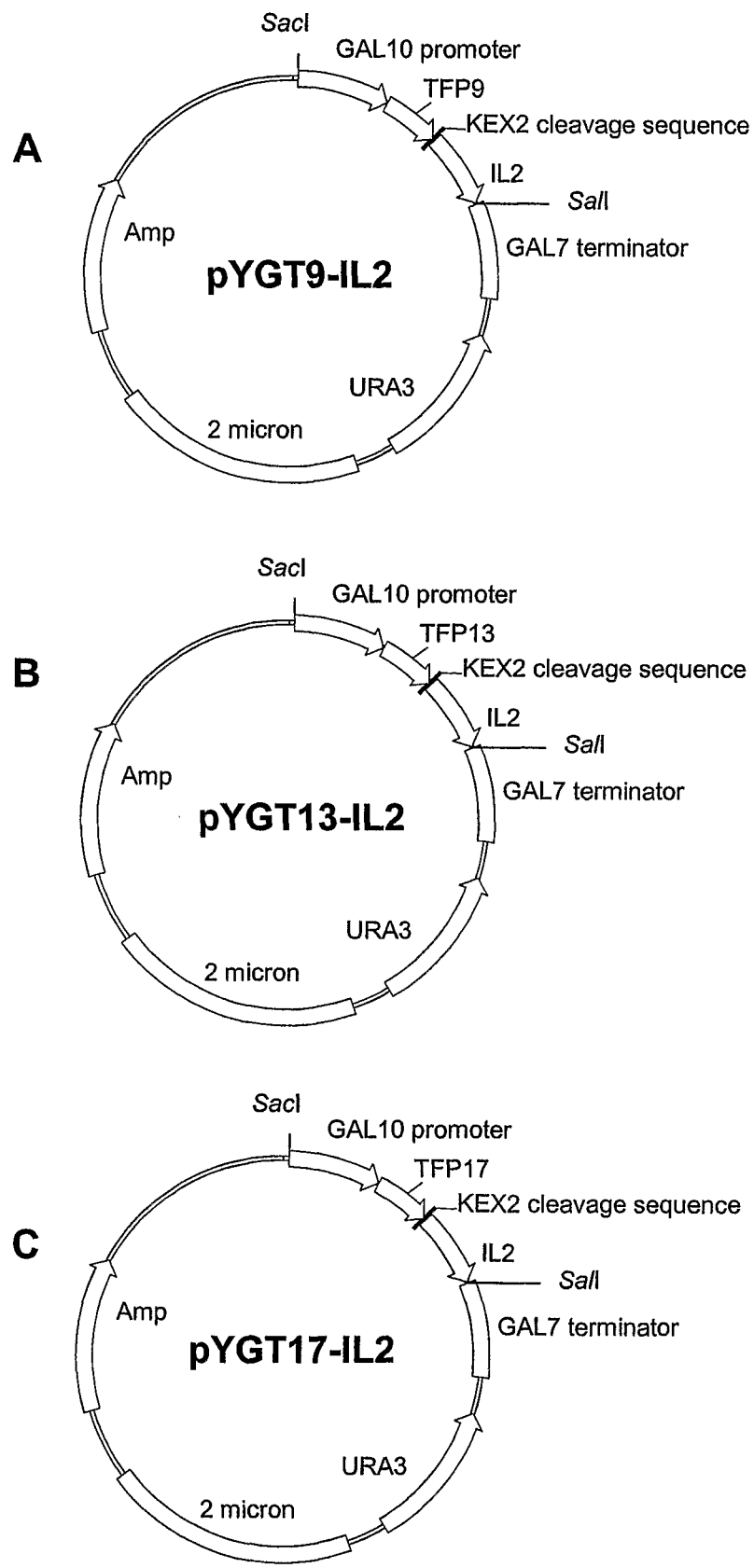
FIG. 15 shows the maps of human IL2 expression vectors (A) pYGT9-IL2, (B) pYGT13-IL2, and (C) pYGT17-IL2.
Figure 16:
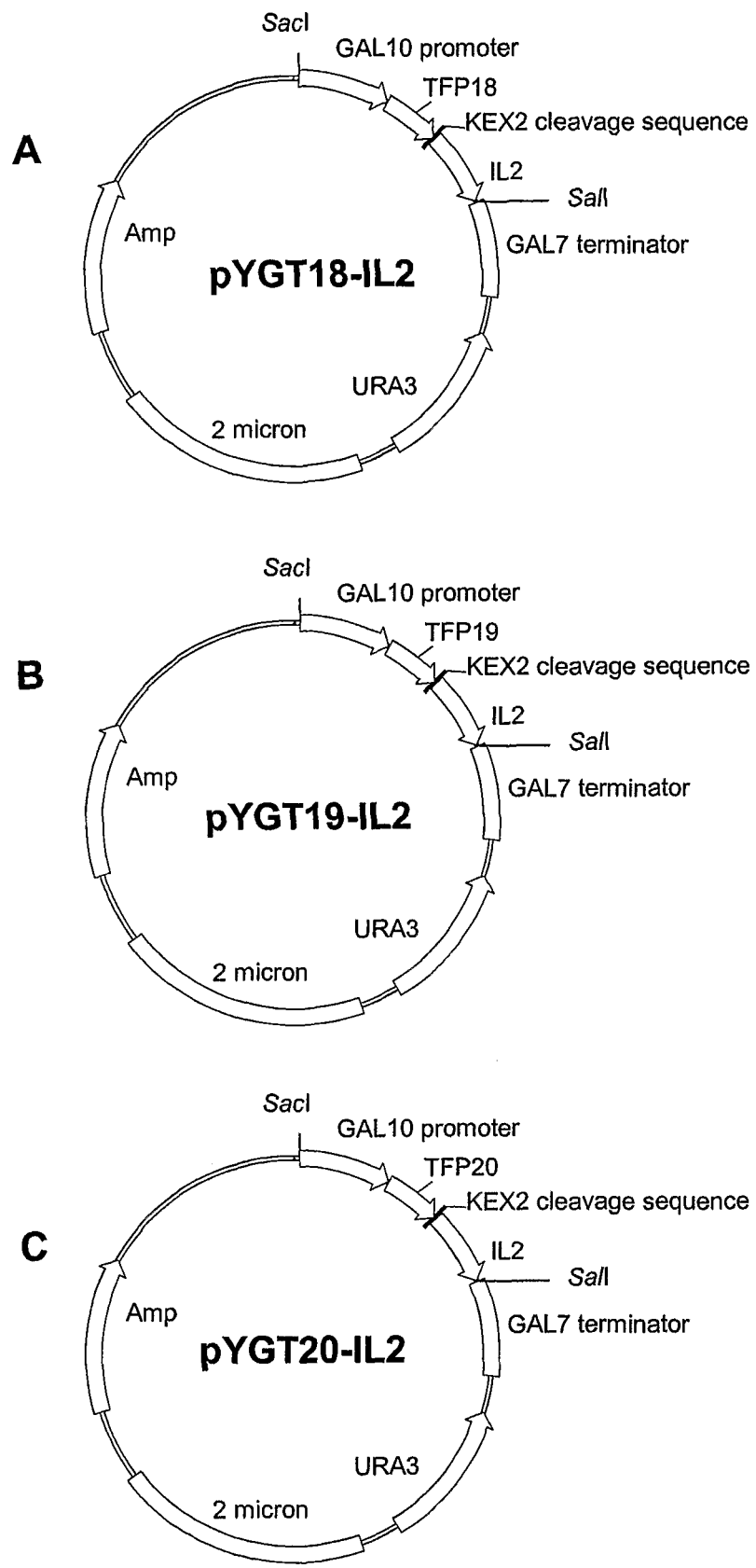
FIG. 16 shows the maps of human IL2 expression vectors (A) pYGT18-IL2, (B) pYGT19-IL2, and (C) pYGT20-IL2.
Figure 17:
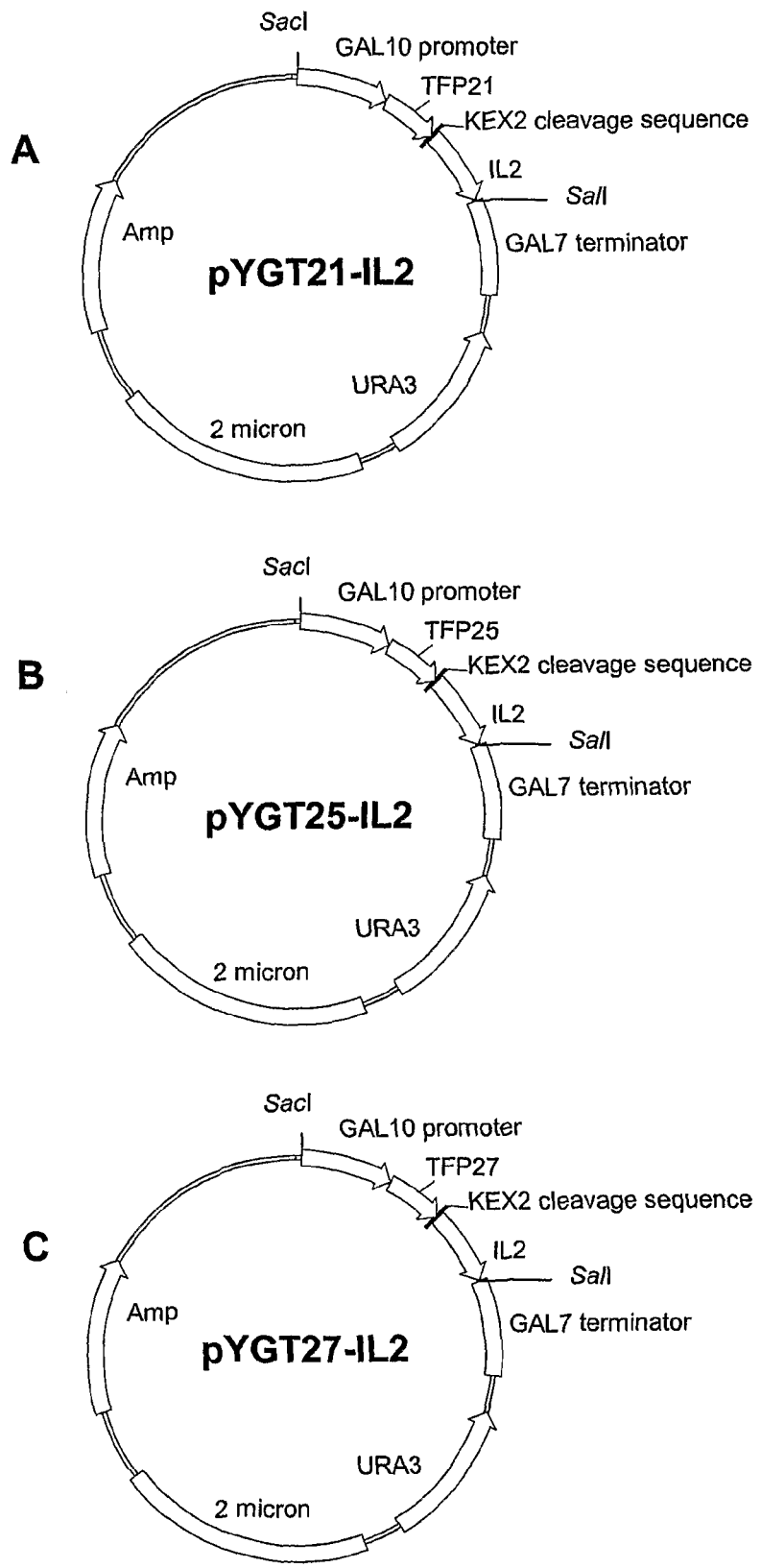
FIG. 17 shows the maps of human IL2 expression vectors (A) pYGT21-IL2, (B) pYGT25-IL2, and (C) pYGT27-IL2.

To confirm the secretion of human IL2 using selected TFPs, 9 plasmids were constructed using PCR to remove the 5'-UTR of each TFP and SUC2 of selected plasmids in Example 10 (FIG. 14). Nine forward primers, BamH-YGR-F (SEQ ID NO:47), BamH-SIM-F (SEQ ID NO:48), BamH-YNL-F (SEQ ID NO:49), BamH-ECM-F (SEQ ID NO:50), BamH-ATG-F (SEQ ID NO:51), BamH-GAS-F (SEQ ID NO:52), BamH-YOR-F (SEQ ID NO:53), BamH-OST-F (SEQ ID NO:54), BamH-UTH-F (SEQ ID NO:55) and a common reverse primer IL2-TGA-R (SEQ ID NO:56) were used for PCR from plasmids pYHTS-TFP9, pYHTS-TFP13, pYHTS-TFP17, pYHTS-TFP18, pYHTS-TFP19, pYHTS-TFP20, pYHTS-TFP21, pYHTS-TFP25, and pYHTS-TFP27, respectively. The nine PCR amplified fragments were digested with BamHI and SalI and each fractionated from an agarose gel. Separately, another PCR to amplify the GAL promoter was done using a forward primer Sac-GAL-F (SEQ ID NO:57) and a reverse primer GAL-BamH-R (SEQ ID NO:58) from YEGα-HIR525 (Sohn et al., *Process Biochem.* 30:653 (1995)). SacI-BamHI digested GAL promoter and the nine BamHI-SalI digested fragments were co-ligated into SacI-SalI digested YEGα-HIR525. The resulting plasmids were named pYGT9-IL2 (FIG. 15A), pYGT13-IL2 (FIG. 15B), pYGT17-IL2 (FIG. 15C), pYGT18-IL2 (FIG. 16A), pYGT19-IL2 (FIG. 16B), pYGT20-IL2 (FIG. 16C), pYGT21-IL2 (FIG. 17A), pYGT25-IL2 (FIG. 17B), and pYGT27-IL2 (FIG. 17C), respectively. Human IL2 expression vectors, pYGT9-IL2 (*E. coli* DH5α/pYGT9-IL2, FIG. 15A) and pYGT17-IL2 (*E. coli* DH5α/pYGT17-IL2, FIG. 15C) were deposited at an international depository authority, KCTC (Korea Collection for Type Cultures; 52, Oun-dong, Yusong-ku, Taejon, Korea) on Jul. 21, 2005, and assigned accession numbers KCTC 10828BP and KCTC 10829BP, respectively. Nucleotide sequences of all constructed vectors were confirmed to have a correct in-frame fusion between TFP and IL2 and each vector was transformed into *S. cerevisiae* Y2805 (Mat a ura3 SUC2 pep4::HIS3 GAL1 can1). Transforming cells were plated on UD media (0.67% yeast nitrogen base without amino acids, 0.77 g/l amino acid mixture, 2% glucose and 2% agar) and incubated at 30° C. for 3 days. A single colony of each transformation was inoculated into YPDG broth (1% yeast extract, 2% Bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed in 12% SDS-PAGE. The gel was stained with gel staining reagent (PhastGel® Blue R, Pharmacia Biotech, USA). As shown in FIG. 18, the levels of secreted IL2 were considerably different between the TFPs but all could secrete human IL2 into culture supernatant. A plasmid pYIL-KRT1-4 (WO 2005/068658) containing a TFP1-human IL2 gene was used as a control. TFP9, 13, 21 and 27 were found to be useful for the secretion of human IL2 (FIG. 18).

EXAMPLE 12

Novel TFP Selected from TFP Library for the Secretion of Human Interleukin-32

As an example for identifying optimal TFPs using a method developed in this invention, a rarely secreting protein, a novel human cytokine, interleukin-32α (hIL32) (Kim et al., *Immunity* 22:131 (2005)) was tested. An insert fragment containing the human IL32α gene and a 500 bp N-terminal part of SUC2 was amplified using PCR as described in Example 8 (FIG. 11). A PCR was carried out using a forward primer KR-IL32α-F (SEQ ID NO:59) and a reverse primer IL32α-INV-R (SEQ ID NO:60) from pProExHTa-IL32α (D Y Yoon, Konkuk University, Korea) as a template. Separately, another PCR for the amplification of an N-terminal part of SUC2 to be fused to the 3'-end of the IL32α gene was also carried out using a forward primer KR-Inv-F (SEQ ID NO:21) and a reverse primer Inv500-R (SEQ ID NO:22) from YGaINV (FIG. 6). Then, a second PCR was done from the two DNA fragments amplified in the first step using a forward primer LNK40 (SEQ ID NO:23) and a reverse primer Inv500-R (SEQ ID NO:22). The resulting fragment (insert fragment) harbored a 40 nucleotide linker DNA containing a Kex2p recognition sequence (Leu-Asp-Lys-Arg (SEQ ID NO:214)), IL32α, an additional Kex2p recognition sequence, and an N-terminal part of invertase in order. This fragment was co-transformed with the SwaI digested TFP library vector constructed in Example 7 into *S. cerevisiae* Y2805Δgal1Δsuc2 (Mat a ura3 suc2::Tc190 pep4::HIS3 gal1 can1). Transformed cells were spread on both UD media (0.67% yeast nitrogen base without amino acids, 0.77 g/l amino acid mixture, 2% glucose and 2% agar) and YPSGA media (1% yeast extract, 2% Bacto-peptone, 2% sucrose, 0.3% galactose, 1 μg/ml antimycin A, and 2% agar) and incubated at 30° C. for 5 days. Around 2×10$^4$ transformants were obtained on UD plates but about 250 transformants were obtained on YPSGA. Thirty eight transformants were randomly selected and cultivated on YPDG broth (1% yeast extract, 2% Bacto-peptone, 1% glucose and 1% galactose) at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed by 12% SDS-PAGE (FIG. 19). Most of the transformants could secrete human IL32α judging from the protein bands appeared around 20 kDa. Among them, 17 transformants showing dark IL32α bands were further analyzed. Each transformant was cultivated on YPD broth and total DNA was isolated and retransformed into *E. coli* DH5α. Transformed *E. coli* was plated on LB media containing ampicillin (1% Bacto-peptone, 0.5% yeast extract, 1% NaCl with 50 μg/ml ampicillin) and incubated at 37° C. overnight. Plasmids were isolated from each *E. coli* transformant using a plasmid extraction kit (Bioneer, Korea). To analyze the sequence of each plasmid, a sequencing primer GAL100-F (SEQ ID NO:12) binding to the GAL10 promoter was used for all plasmids containing TFPs. Nucleotide sequences were determined by Genotech Co. (Taejon, Korea) using an automated sequencing unit (ABI Prism 377; PE Biosystems, Foster City, Calif., USA). The sequences were analyzed by a BLAST search of the *Saccharomyces* Genome Database (yeastgenome.org). As a result, nine different TFPs were identified from plasmids isolated from 17 selected yeast strains. The isolated plasmids were named pYHTS-IL32-TFP3, pYHTS-IL32-TFP11, pYHTS-IL32-TFP13, pYHTS-IL32-TFP21, pYHTS-IL32-TFP22, pYHTS-IL32-TFP25, pYHTS-IL32-TFP29 pYHTS-IL32-TFP34, and pYHTS-IL32-TFP38. Among them, TFP3, TFP13, TFP21 and TFP25 were commonly obtained as optimal TFPs for human IL2 (WO 2005/068658) and in Example 10 (Table 1). Five novel TFPs isolated for IL32α are summarized in Table 2.

TABLE 2

Novel TFPs for the secretion of human interleukin-32α

| Number of TFP | Yeast ORF | Number of fused amino acids(total) | Signal sequence | SEQ ID for protein | SEQ ID for DNA |
|---|---|---|---|---|---|
| TFP-11 | YDR077W | 187(338) | Pre(18aa) | 61 | 62 |
| TFP-22 | YJL159W | 165(310) | PrePro(19 + 54aa) | 63 | 64 |
| TFP-29 | YEL060C | 48(635) | Pre(19aa) | 65 | 66 |

TABLE 2-continued

Novel TFPs for the secretion of human interleukin-32α

| Number of TFP | Yeast ORF | Number of fused amino acids(total) | Signal sequence | SEQ ID for protein | SEQ ID for DNA |
|---|---|---|---|---|---|
| TFP-34 | YLR390W-A | 208(238) | Pre(22aa) | 67 | 68 |
| TFP-38 | YMR251W-A | 38(59) | Pre(20aa) | 69 | 70 |

EXAMPLE 13

Secretion of Human IL32α Using Selected TFPs

To confirm the secretion of human IL32α using selected TFPs, several plasmids were constructed using PCR to remove the 5'-UTR of each TFP and SUC2 of selected plasmids in Example 12. Six forward primers, BamH-CIS-F (SEQ ID NO:71), BamH-SED-F (SEQ ID NO:72), BamH-SIM-F (SEQ ID NO:73), BamH-YO 47W-F (SEQ ID NO:74), BamH-HSP—F (SEQ ID NO:75), BamH-OST-F (SEQ ID NO:76), and a common reverse primer IL32-TGA-R (SEQ ID NO:77) were used for PCR from plasmids pYHTS-IL32-TFP3, pYHTS-IL32-TFP11, pYHTS-IL32-TFP13, pYHTS-IL32-TFP21, pYHTS-IL32-TFP22, and pYHTS-IL32-TFP25, respectively. The six PCR amplified fragments were digested with BamHI and SalI and each fractionated from an agarose gel. Separately, another PCR to amplify the GAL promoter was done using a forward primer Sac-GAL-F (SEQ ID NO:57) and a reverse primer GAL-BamH-R (SEQ ID NO:58) from YEGα-HIR525 (Sohn et al., *Process Biochem.* 30:653 (1995)). SacI-BamHI digested GAL promoter and the six BamHI-SalI digested fragments were co-ligated into SacI-SalI digested YEGα-HIR525. The resulting plasmids were named pYGT3-IL32α, pYGT11-IL32α, pYGT13-IL32α, pYGT21-IL32α, pYGT22-IL32α, and pYGT25-IL32α, respectively. Nucleotide sequences of all constructed vectors were confirmed to have a correct in-frame fusion between TFP and IL32α and each vector was transformed into *S. cerevisiae* Y2805 (Mat a ura3 SUC2 pep4::HIS3 GAL1 can1). Transformed cells were plated on UD media (0.67% yeast nitrogen base without amino acids, 0.77 g/l amino acid mixture, 2% glucose and 2% agar) and incubated at 30° C. for 3 days. A single colony of each transformation was inoculated into YPDG broth (1% yeast extract, 2% Bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed on 12% SDS-PAGE. The gel was stained with gel staining reagent (PhastGel® Blue R, Pharmacia Biotech, USA). Secreted IL32α was further analyzed by Western blotting using a monoclonal antibody of hIL32α. Proteins were transferred to PVDF membranes (Millipore, USA) in CAPS buffer (2.2 g per liter CAPS, MeOH 10%, pH 11 adjusted with NaOH) using a Mighty small tank transfer (Hoefer, USA) at 300 mA for 90 min. Proteins were then detected with human IL32 antibody (D Y Yoon, Konkuk University, Korea). Membranes were blocked overnight at 4° C. in PBS (137 mM NaCl, 2.7 mM KCl, 10 mM $Na_2HPO_4$, 2 mM $KH_2PO_4$, pH 7.4 adjusted with HCl) containing 5% skim milk. Membranes were washed 3 times with PBS containing 0.05% Tween-20 and then incubated with primary antibodies diluted in PBS containing 3% skim milk at room temperature for 1 hour. Membranes were then washed 3 times and incubated with the anti-mouse secondary antibody (Sigma Chemical Co., USA) diluted in PBS containing 3% skim milk at room temperature for 1 hour. Membranes were washed as above and developed with Sigma Fast NBT/BCIP (Sigma Chemical Co., USA). As shown in FIG. 20, all selected TFPs could secrete human IL32α into the culture supernatant. Among them, TFP3, 13, 21 and 22 were found to be optimal for the secretion of human IL32α.

EXAMPLE 14

Fed-Batch Fermentation for the Production of Human IL32α

A recombinant yeast strain transformed with pYGT3-IL32α was cultured in a 5-L jar fermentor by fed-batch culture for the evaluation of the secretory productivity of human IL32α. A 200 ml seed culture was cultured in a 1 liter flask using a minimal medium (0.67% yeast nitrogen base without amino acids, 0.5% casamino acids and 2% glucose). When the culture using a fermentation culture medium (4% yeast extract, 1% peptone, 2% glucose) as an initial fermentation medium reached an OD600 of about 15, a fed-batch medium (15% yeast extract, 30% glucose) was supplied with different feeding rates according to cell growth rates. After the culture reached an OD600 of about 130, galactose (30% galactose) was additionally supplied with different feeding rates according to cell growth rates. After a culture period of about 72 hrs, the culture reached an OD600 of about 220 (FIG. 21A). 15 µl of the medium was collected at the given time points and assessed for secreted proteins by SDS-PAGE (FIG. 21B). Over 300 mg/L of hIL32α was found to be secreted into the culture medium as determined by the direct measurement of proteins with BCA protein assay reagent (Pierce, USA) and with a densitometer (GS700, Bio-Rad, USA).

EXAMPLE 15

Sequence-Based Selection of TFPs Using Blast Search from Yeast Genomic Database

For the sequence-based selection of TFPs from the yeast genome, amino acid sequences of pre-secretion signals of 18 selected TFPs (4 from WO 2005/068658, 9 from example 10 and 5 from example 12) were used as a query sequence for a BLAST search of the *Saccharomyces* Genome Database (yeastgenome.org). Using a low expect threshold (100 or 1000) in the BLASTP search, several hundred ORFs having over 70% homology were identified. Of those, the ORFs with sequence homology near the N-terminus were selected, and further subjected to SignalP (cbs.dtu.dk/services/SignalP-2.0/) analysis for the selection of ORFs with secretion signal. As a result, 18 ORFs were randomly selected as TFP candidates. Eighteen selected ORFs identified by the search were YGR279C (SCW4, cell wall protein), YLR037C (DAN2, cell wall mannoprotein), YLR110C (CCW12, cell wall protein), YOR383C (FIT3, cell wall mannoprotein), YIL011W (TIR3, cell wall mannoprotein), YHR214W (putative membrane protein), YNL160W (YGP1, cell wall-related secretory glycoprotein), YGR296C-A (dubious open reading frame), YOL154W (ZPS1, putative GPI-anchored protein), YPL187W (MFα, mating pheromone alpha-factor), YHR214W (putative membrane protein), YKR013W (PRY2, protein of unknown function), YHR139C(SPS100, protein required for spore wall maturation), YIL169C (putative protein of unknown function), YOL155C (uncharacterized ORF), YMR325W (PAU19, hypothetical protein), YDR134W (hypothetical protein) and YLR300W (EXG1, major exo-1,3-beta-glucanase of the cell wall). Each ORF was amplified from the genomic DNA of S. cerevisiae Y2805 (Mat a ura3 SUC2 pep4::HIS3 GAL1 can1) using PCR primer pairs YGR279C-F (SEQ ID NO:92) and YGR279C-R (SEQ ID NO:93) for YGR279C, YLR037C-F (SEQ ID NO:94) and YLR037C-R (SEQ ID NO:95) for YLR037C, YLR110C-F (SEQ ID NO:96) and YLR110C-R (SEQ ID NO:97) for YLR110C, YOR383C-F (SEQ ID NO:98) and YOR383C-R (SEQ ID NO:99) for YOR383C, YIL011W-F (SEQ ID NO:100) and YIL011W-R (SEQ ID NO:101) for YIL011W, YHR214W-F (SEQ ID NO:102) and YHR214W-R (SEQ ID NO:103) for YIR214W, YNL160W-F (SEQ ID NO:104) and YNL160W-R (SEQ ID NO:105) for YNL160W, YGR296C-A-F (SEQ ID NO:106) and YGR296C-A-R (SEQ ID NO:107) for YGR296C-A, YOL154W-F (SEQ ID NO:108) and YOL154W-R (SEQ ID NO:109) for YOL154W, YPL187W-F (SEQ ID NO:110) and YPL187W-R (SEQ ID NO:111) for YPL187W, YHR214W-F (SEQ ID NO:112) and YHR214W-R (SEQ ID NO:113) for YHR214W, YKR013W-F (SEQ ID NO:114) and YKR013W-R (SEQ ID NO:115) for YKR013W, YHR139C-F (SEQ ID NO:116) and YHR139C-R (SEQ ID NO:117) for YHR139C, YIL169C-F (SEQ ID NO:118) and YIL169C-R (SEQ ID NO:119) for YIL169C, YOL155C-F (SEQ ID NO:120) and YOL155C-R (SEQ ID NO:121) for YOL155C, YMR325W-F (SEQ ID NO:122) and YMR325W-R (SEQ ID NO:123) for YMR325W, YDR134W-F (SEQ ID NO:124) and YDR134W-R (SEQ ID NO:125) for YDR134W and YLR300W-F (SEQ ID NO:126) and YLR300W-R (SEQ ID NO:127) for YLR300W, respectively. PCR was performed with Pfu polymerase (Stratagene, USA) and PCR conditions included one cycle of 94° C. for 3 min, and 25 cycles of 94° C. for 30 sec, 55° C. for 30 sec and 72° C. for 2 min, followed by one final cycle of 72° C. for 7 min. Each amplified PCR fragment was confirmed by nucleotide sequencing by Genotech Co. (Taejon, Korea) using an automated sequencing unit (ABI Prism 377; PE Biosystems, Foster City, Calif., USA).

For the screening of TFPs from the selected 18 ORFs, unidirectional deletion of the mixture of 18 PCR fragments was carried out and used for the construction of a TFP library in YGadV45 (FIG. 24). Single stranded template was obtained by unidirectional PCR using a primer SfiA-F (SEQ ID NO:128) from the template consisting of the 18 ORFs. PCR was performed with ExTaq (Takara Korea, Korea) and PCR conditions included one cycle of 94° C. for 3 min, and 30 cycles of 94° C. for 30 sec, 55° C. for 30 sec and 72° C. for 2 min, followed by one final cycle of 72° C. for 7 min. PCR product containing the single stranded DNA was purified using a PCR purification kit (Bioneer, Korea). Then, the regeneration of double stranded DNA was carried out using E. coli DNA polymerase I (NEB, England) and a random hexameric primer, ASA24N6 (SEQ ID NO:16). A reaction mixture containing 20 μl of template DNA, 1111 of ASA24N6 primer, 3 μl of 10×E. coli DNA poll buffer, 5 μl of 2.5 mM dNTP, and 1 μl of E. coli DNA poll was incubated at 37° C. for 1 hour. The DNA was column purified using a PCR purification kit (Bioneer, Korea) and PCR amplified using primers SfiA-F (SEQ ID NO:128) and ASA24 (SEQ ID NO:17). The amplified DNA was column purified again, digested with SfiI and fractionated by agarose gel electrophoresis. 0.5-1.0 kb of SfiI digested DNA was subcloned into the SfiI treated YGadV45 containing a defective SUC2 (dSUC2). The ligated DNA was transformed into E. coli DH5α. Transformed E. coli was plated on LB media with ampicillin (1% Bacto-peptone, 0.5% yeast extract, 1% NaCl with 50 μg/ml ampicillin) and incubated at 37° C. overnight. About $1 \times 10^4$ E. coli colonies were pooled with sterile distilled water and the total plasmids containing the unidirectional-deleted DNA fragment library of 18 ORFs in YGadV45, were isolated by using a plasmid isolation kit (Bioneer, Korea).

To screen proper TFPs from the unidirectional-deleted DNA fragment library of 18 ORFs, a gene encoding human interleukin-2 (hIL2) was inserted between the library and dSUC2. An insert fragment containing the hIL2 gene and a 500 bp N-terminal part of SUC2 was amplified using PCR as described in Example 8 (FIG. 11). This fragment was co-transformed with SwaI digested vector containing the unidirectional-deleted DNA fragment library of 18 ORFs into S. cerevisiae Y2805Δgal1Δsuc2 (Mat a ura3; suc2::Tc190 pep4::HIS3 gal1 can1). Transformed cells were spread on both UD media (0.67% yeast nitrogen base without amino acids, 0.77 g/l amino acid mixture, 2% glucose and 2% agar) and YPSGA media (1% yeast extract, 2% Bacto-peptone, 2% sucrose, 0.3% galactose, 1 μg/ml antimycin A, and 2% agar) and incubated at 30° C. for 5 days. Around $2 \times 10^4$ transformants were obtained on UD plates but about several hundred transformants were obtained in YPSGA. A random selection of 29 transformants growing on YPSGA was cultivated on YPDG broth (1% yeast extract, 2% Bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed by 12% SDS-PAGE (FIG. 25). Several transformants were found to secrete human IL-2 into the culture supernatant. Total DNA was isolated from each cell secreting human IL-2 and retransformed into E. coli DH5α. Plasmids were isolated from each E. coli transformant using a plasmid extraction kit (Bioneer, Korea). To analyze the sequence of each TFP, a sequencing primer GAL100-F (SEQ ID NO:12) binding to the GAL10 promoter was used for all plasmids containing TFPs. Nucleotide sequences were determined by Genotech Co. (Taejon, Korea) using an automated sequencing unit (ABI Prism 377; PE Biosystems, Foster City, Calif., USA). The sequences were analyzed by a BLAST search of the Saccharomyces Genome Database (yeastgenome.org). As a result, six novel TFPs were identified from plasmids isolated from the 12 transformants secreting human IL-2. The isolated plasmids were named pYIL-TFP39, pYIL-TFP41, pYIL-TFP43, pYIL-TFP44, pYIL-TFP52, and pYIL-TFP54, respectively. The six novel TFPs are summarized in Table 3.

TABLE 3

TFPs from sequence-based selected ORFs for the secretion of human IL-2

| Number of TFP | Yeast ORF | Number of fused amino acids(total) | Signal sequence | SEQ ID for protein | SEQ ID for DNA |
|---|---|---|---|---|---|
| TFP-39 | YGR279C | 57(386) | Pre(19aa) | 129 | 130 |
| TFP-43 | YLR110C | 129(133) | Pre(18aa) | 131 | 132 |
| TFP-44 | YOR383C | 71(204) | Pre(18aa) | 133 | 134 |
| TFP-48 | YGR279C | 119(386) | Pre(19aa) | 135 | 136 |
| TFP-52 | YNL160W | 129(354) | Pre(19aa) | 137 | 138 |
| TFP-54 | YLR037C | 124(124) | Pre(20aa) | 139 | 140 |

EXAMPLE 16

Diversification of CORE-TFPs by Unidirectional Deletion

To diversify the usefulness of 14 TFPs (core-TFPs) selected by using IL-2 and IL-32α in Examples 10 and 11, and 3 TFPs previously identified in WO 2005/068658, seventeen genomic ORFs, YAR066W for TFP-1, YFR026C for TFP-2, YJL158C for TFP3, YGR106C for TFP-9, YDR077W for TFP-11, YIL123W for TFP13, YNL190W for TFP-17, YBR078W for TFP18, YJL178C for TFP-19, YMR307W for TFP-20, YOR247W for TFP-21, YJL159W for TFP-22, YOR085W for TFP-25, YKR042W for TFP-27, YEL060C for TFP29, YLR390W-A for TFP-34, and YMR251W-A for TFP-38, were PCR amplified and unidirectionally deleted as described in Example 15. Each ORF was amplified from the genomic DNA of S. cerevisiae Y2805 (Mat a ura3 SUC2 pep4::HIS3 GAL1 can1) using PCR primer pairs YAR066W-F (SEQ ID NO:141) and YAR066W-R (SEQ ID NO:142) for YAR066W, YFR026C-F (SEQ ID NO:143) and YFR026C-R (SEQ ID NO:144) for YFR026C, YJL158C-F (SEQ ID NO:145) and YJL158C-R (SEQ ID NO:146) for YJL158C, YGR106C-F (SEQ ID NO:147) and YGR106C-R (SEQ ID NO:148) for YGR106c, YDR077W-F (SEQ ID NO:149) and YDR077W-R (SEQ ID NO:150) for YDR077W, YIL123W-F (SEQ ID NO:151) and YIL123W-R (SEQ ID NO:152) for YIL123W, YNL190W-F (SEQ ID NO:153) and YNL190W-R (SEQ ID NO:154) for YNL190W, YBR078W-F (SEQ ID NO:155) and YBR078W-R (SEQ ID NO:156) for YBR078W, YJL178C-F (SEQ ID NO:157) and YJL178C-R (SEQ ID NO:158) for YJL178C, YMR307W-F (SEQ ID NO:159) and YMR307W-R (SEQ ID NO:160) for YMR307W, YOR47W-F (SEQ ID NO:161) and YOR247W-R (SEQ ID NO:162) for YOR47W, YJL159W-F (SEQ ID NO:163) and YJL159W-R (SEQ ID NO:164) for YJL159W, YOR085W-F (SEQ ID NO:165) and YOR085W-R (SEQ ID NO:166) for YOR085W, YKR042W-F (SEQ ID NO:167) and YKR042W-R (SEQ ID NO:168) for YKR042W, YEL060C-F (SEQ ID NO:169) and YEL060C-R (SEQ ID NO:170) for YEL060C, YLR390W-A-F (SEQ ID NO:171) and YLR390W-A-R (SEQ ID NO:172) for YLR390W-A, YMR251W-A-F (SEQ ID NO:173) and YMR251W-A-R (SEQ ID NO:174) for YMR251W-A, respectively. PCR was performed with Pfu polymerase (Stratagene, USA) and PCR conditions included one cycle of 94° C. for 3 min, and 25 cycles of 94° C. for 30 sec, 55° C. for 30 sec and 72° C. for 2 min, followed by one final cycle of 72° C. for 7 min. Each amplified PCR fragment was confirmed by nucleotide sequencing by Genotech Co. (Taejon, Korea) using an automated sequencing unit (ABI Prism 377; PE Biosystems, Foster City, Calif., USA).

For the screening of diversified TFPs from the 17 ORFs from which 17 core-TFPs were obtained, unidirectional deletion of the mixture of 17 PCR fragments was carried out and used for the construction of a TFP library in YGadV45 (FIG. 24). Single stranded template was obtained by unidirectional PCR using a primer SfiA-F (SEQ ID NO:128) from the template consisting of 17 ORFs. PCR was performed with ExTaq (Takara Korea, Korea) and PCR conditions included one cycle of 94° C. for 3 min, and 30 cycles of 94° C. for 30 sec, 55° C. for 30 sec and 72° C. for 2 min, followed by one final cycle of 72° C. for 7 min. PCR product containing the single stranded DNA was purified using a PCR purification kit (Bioneer, Korea). Then, the regeneration of double stranded DNA was carried out using E. coli DNA polymerase I (NEB, England) and a random hexameric primer, ASA24N6 (SEQ ID NO:16). A reaction mixture containing 20 μl of template DNA, 1 μl of ASA24N6 primer, 3 μl of 10× E. coli DNA poll buffer, 5 μl of 2.5 mM dNTP, and 1 μl of E. coli DNA poll was incubated at 37° C. for 1 hour. The DNA was column purified using a PCR purification kit (Bioneer, Korea) and PCR amplified using primers SfiA-F (SEQ ID NO:128) and ASA24 (SEQ ID NO:17). The amplified DNA was column purified again, digested with SfiI and fractionated by agarose gel electrophoresis. 0.5-1.0 kb of SfiI digested DNA was subcloned into SfiI treated YGadV45 containing a defective SUC2 (dSUC2). The ligated DNA was transformed into E. coli DH5α. Transformed E. coli was plated on LB media with ampicillin (1% Bacto-peptone, 0.5% yeast extract, 1% NaCl with 50 μg/ml ampicillin) and incubated at 37° C. overnight. About 1×10⁴ E. coli colonies were pooled with sterile distilled water and the total plasmids containing the unidirectional-deleted DNA fragment library of 17 ORFs in YGadV45 were isolated by using a plasmid isolation kit (Bioneer, Korea). Two unidirectional-deleted library DNAs from 17 ORFs for core-TFPs and 18 ORFs prepared in Example 15 were combined for further application.

To screen proper TFPs from the unidirectional-deleted DNA fragment library from 35 ORFs, a gene encoding human interleukin-2 (hIL2) was inserted between the library and dSUC2. An insert fragment containing the human IL2 gene and a 500 bp N-terminal part of SUC2 was amplified using, PCR as described in Example 8 (FIG. 11). This fragment was co-transformed with SwaI digested vector containing the unidirectional-deleted DNA fragment library of 35 ORFs, into S. cerevisiae Y2805Δgal1Δsuc2 (Mat a ura3 suc2::Tc190 pep4::HIS3 gal1 can1). Transformed cells were spread on both UD media (0.67% yeast nitrogen base without amino acids, 0.77 g/l amino acid mixture, 2% glucose and 2% agar) and YPSGA media (1% yeast extract, 2% Bacto-peptone, 2% sucrose, 0.3% galactose, 1 μg/ml antimycin A, and 2% agar) and incubated at 30° C. for 5 days. Around 2×10⁴ transformants were obtained on UD plates but about several hundred transformants were obtained in YPSGA. A random selection of 24 transformants growing on YPSGA was cultivated on YPDG broth (1% yeast extract, 2% Bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed by, 12% SDS-PAGE (FIG. 26). Most of the transformants could secrete human IL-2 into the culture supernatant but with different levels between them. Total DNA was isolated from each transformant secreting human IL-2 and retransformed into E. coli DH5u. Plasmids were isolated from E. coli using a plasmid extraction kit (Bioneer, Korea). To analyze the sequence of each TFP, a sequencing primer GAL100-F (SEQ ID NO:12) binding to the GAL10 promoter were used for all plasmids containing TFPs. Nucleotide sequences were determined by Genotech Co. (Taejon, Korea) using an automated sequencing unit (ABI Prism 377; PE Biosystems, Foster City, Calif., USA). The sequences were analyzed by a BLAST search of the *Saccharomyces* Genome Database (yeastgenome.org). As a result, six novel TFPs were identified from plasmids isolated from the 18 transformants secreting human IL-2. The isolated plasmids were named pYIL-TFP40, pYIL-TFP50, pYIL-TFP51, pYIL-TFP57, pYIL-TFP58, and pYIL-TFP59, respectively. The six novel TFPs are summarized in Table 4.

TABLE 4

TFPs from sequence-based selected ORFs for the secretion of human IL-2

| Number of TFP | Yeast ORF | Number of fused amino acids(total) | Signal sequence | SEQ ID for protein | SEQ ID for DNA |
|---|---|---|---|---|---|
| TFP-40 | YGR279C | 99(386) | Pre(19aa) | 175 | 176 |
| TFP-50 | YOR247W | 85(210) | Pre(19aa) | 177 | 178 |
| TFP-51 | YOR247W | 116(210) | Pre(19aa) | 179 | 180 |
| TFP-57 | YOL155C | 114(967) | Pre(23aa) | 181 | 182 |
| TFP-58 | YAR066W | 199(203) | Pre(23aa) | 183 | 184 |
| TFP-59 | YOR085W | 55(350) | Pre(17aa) | 185 | 186 |

EXAMPLE 17

Artificial TFPs Using Swapping of Pre and Pro Signal Sequence Between Core-TFPs

To date, a yeast secretion signal from mating factor alpha (MFα) has been the most widely used for the secretion of various recombinant proteins in yeast (Romanos et al., *Yeast* 8:423 (1992)). The secretion signal comprises 19 amino acids of pre-signal and 66 amino acids of pro-signal. The exact function of pro-signal is uncertain but it has been known to be essential for the correct folding and secretion of some proteins. The fact was also investigated in the secretion of some recombinant proteins in yeast (Chaudhuri et al., *Eur. J. Biochem.* 206:793 (1992)). In this invention, two secretion signals, TFP-3 and TFP-22, were identified as pre-pro type. For the expansion of the usefulness of TFPs selected in this invention, artificial TFPs were designed to have a different origin of the pre and pro signals. Four artificial TFPs were constructed using the pre-signal of TFP-1, 2, 3 and 4 and a common pro-signal of mating factor alpha and the resulting TFPs were named as TFP-5, 6, 7, and 8. For the fusion between 4 different pre-signals and a common pro signal, overlap extension PCR was used.

A first step PCR was carried out for the amplification of four different pre-signals of 4 TFPs using primer pairs T1-F (SEQ ID NO:187) and T1-R (SEQ ID NO:188), T2-F (SEQ ID NO:189) and T2-R (SEQ ID NO:190), T3-F (SEQ ID NO:191) and T3-R (SEQ ID NO:192), T4-F (SEQ ID NO:193) and T4-R (SEQ ID NO:194) from plasmids pYIL-KRTFP1, 2, 3, and 4 (WO 2005/068658), respectively. Separately, another PCR for the amplification of about 190 bp of mating factor alpha pro-signal was also carried out using primers MF-Pro-F (SEQ ID NO:195) and MF-R (SEQ ID NO:196) from plasmid YEGα-HIR525. Then second PCRs for the 4 different pre-pro signals were done from 4 sets of two DNA fragments, 4 pre-signals and a MFα pro-signal amplified in the first step using 4 different forward primers, T1-F (SEQ ID NO:187), T2-F (SEQ ID NO:189), T3-F (SEQ ID NO:191) and T4-F (SEQ ID NO:193) and a common reverse primer, MF-R (SEQ ID NO:196), respectively. To compare the efficiency of each artificial pre-pro signal sequence with that of mating factor alpha, pre-pro signal of mating factor alpha was also PCR amplified using primers MF-Pre-F (SEQ ID NO:197) and MF-R (SEQ ID NO:196) from YEGα-HIR525.

A target protein, human insulin-like growth factor (hIGF) was selected to test the five pre-pro signal sequences. It has been reported that the pro signal of mating factor alpha was necessary for the secretion of human insulin-like growth factor in yeast (Chaudhuri et al, *Eur. J. Biochem.* 206:793 (1992)). Human IGF gene was first PCR amplified using primers KR-IGF-F (SEQ ID NO:198) and IGF-R (SEQ ID NO:199) from a human cDNA library (ES Choi, Korea Research Institute of Bioscience and Biotechnology, Korea) and then a second PCR was done using LNK40 (SEQ ID NO:23) and IGF-R (SEQ ID NO:199). The DNA fragment containing IGF was fused to the previously amplified 5 PCR fragments containing pre-pro signals using 5 forward primers, T1-F (SEQ ID NO:187), T2-F (SEQ ID NO:189), T3-F (SEQ ID NO:191), T4-F (SEQ ID NO:193), MF-Pre-F (SEQ ID NO:197) and a common reverse primer IGF-R (SEQ ID NO:199). All fused PCR products were digested with SfiI and SalI and then subcloned into the SfiI-SalI digested vector YGaIINV (FIG. 6). The resulting plasmids were named pYGa-T1α-IGF, pYGa-T2α-IGF pYGa-T3α-IGF pYGa-T4α-IGF and pYGa-MFα-IGF, respectively. Five plasmids were transformed into S. cerevisiae Y2805 (Mat a ura3 pep4::HIS3 gal1 can1). Transformed cells were spread on UD media (0.67% yeast nitrogen base without amino acids, 0.77 g/l amino acid mixture, 2% glucose and 2% agar). A single colony of each transformation was isolated and cultivated in YPDG (1% yeast extract, 2% Bacto-peptone, 1% glucose and 1% galactose) at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed by 12% SDS-PAGE. Secreted IGF was further analyzed by Western blotting using an antibody for hIGF (FIG. 27). All tested pre-pro secretion signals could secrete human IGF into the culture supernatant but with different efficiencies. Among 5 pre-pro signals, T3α (pre-signal from TFP-3 and pro-signal from MFα) and T4α (pre-signal from TFP-4 and pro-signal from MFα) were found to be effective for the secretion of human IGF. The four artificial TFPs and a novel TFP are summarized in Table 5.

TABLE 5

Novel TFPs for the secretion of human IGF

| Number of TFP | Yeast ORF | Number of fused amino acids | Signal sequence | SEQ ID for protein | SEQ ID for DNA |
|---|---|---|---|---|---|
| TFP-5 | YAR066W/YPL187W | 88 | PrePro(23 + 65aa) | 200 | 201 |
| TFP-6 | YFR026C/YPL187W | 84 | PrePro(19 + 65aa) | 202 | 203 |
| TFP-7 | YJL158C/YPL187W | 86 | PrePro(21 + 65aa) | 204 | 205 |
| TFP-8 | HpPRB1/YPL187W | 83 | PrePro(18 + 65aa) | 206 | 207 |
| TFP-32 | YPL187W | 84 | PrePro(19 + 65aa) | 208 | 209 |

EXAMPLE 18

Construction of the Selected TFP Vectors Applicable to Many Target Genes through In Vivo Recombination Thirty five TFPs (core-TFPs) selected in this invention (4 TFPs from WO 2005/068658, 14 TFPs selected using two reporter proteins, human IL2 and IL32α in Example 10 and 11, 6 TFPs from ORFs selected by BLAST search in Example 15, 6 TFPs from unidirectional deletion of ORFs encoding the pre-selected TFPs in Example 16, 5 TFPs from artificial design of TFPs in Example 17) might be also useful for the secretion of other proteins. To apply such vectors to large numbers of target genes, the core-TFP vectors were reconstructed for in vivo recombination with target genes. For the construction of plasmid YGaSW, a PCR for the amplification of 170 bp fragment containing an EcoRI, 2 SfiI, NotI, a linker DNA containing a Kex2p recognition site, SwaI and SalI site was carried out using primers GAL100-F (SEQ ID NO:12) and H77-1-R (SEQ ID NO:78) from YGadV45 (FIG. 10). An EcoRI-SalI digested PCR fragment was subcloned into EcoRI-SalI digested YGadV45 and the resulting plasmid was named YGaSW. The plasmid harbors restriction sites for EcoRI, SfiI, NotI, SfiI, a 40 bp linker and restriction sites SwaI and SalI between the GAL10 promoter and the GAL7 terminator. Thirty five core-TFPs were obtained by the SfiI digestion of plasmids containing each TFP. Each core-TFP was gel purified and subcloned into SfiI digested YGaSW and the resulting 35 plasmids were named YGaSW-TFP1, YGaSW-TFP2, YGaSW-TFP3, YGaSW-TFP4, YGaSW-TFP5, YGaSW-TFP6, YGaSW-TFP7, YGaSW-TFP8, YGaSW-TFP9, YGaSW-TFP11, YGaSW-TFP13, YGaSW-TFP17, YGaSW-TFP18, YGaSW-TFP19, YGaSW-TFP20, YGaSW-TFP21, YGaSW-TFP22, YGaSW-TFP25, YGaSW-TFP27, YGaSW-TFP29, YGaSW-TFP32 YGaSW-TFP34, YGaSW-TFP38, YGaSW-TFP39, YGaSW-TFP40, YGaSW-TFP43, YGaSW-TFP44, YGaSW-TFP48, YGaSW-TFP50, YGaSW-TFP51, YGaSW-TFP52, YGaSW-TFP54, YGaSW-TFP57, YGaSW-TFP58, and YGaSW-TFP59, respectively.

EXAMPLE 19

Evaluation of Selected Core-TFPs for the Secretion of Human Growth Hormone

Core-TFPs selected in this invention were tested for the secretion of human growth hormone (hGH). The human GH gene was PCR amplified from a human cDNA library (ES Choi, Korea Research Institute of Bioscience and Biotechnology, Korea) using primers hGH-F (SEQ ID NO:79) and hGH-R (SEQ ID NO:80) and subcloned into pST-Blue1 (Novagen, USA). The resulting plasmid was named pST-hGH. A second PCR was carried out using primers KR-hGH-F (SEQ ID NO:81) and hGH-Sal-R (SEQ ID NO:82) from pST-hGH. The PCR product containing the hGH gene was used for a third PCR using primers LNK40 (SEQ ID NO:23) and GT70-R (SEQ ID NO:83) to add homologous sequences with YGaSW-TFP vectors constructed in Example 18. The amplified PCR fragment was mixed 2:1 with SwaI digested YGaSW-TFP vectors and transformed into S. cerevisiae Y2805 (Mat a ura3 SUC2 pep4::HIS3 GAL1 can1) through in vivo recombination. Transformed cells were plated on LTD media (0.67% yeast nitrogen base without amino acids, 0.77 g/l amino acid mixture, 2% glucose and 2% agar) and incubated at 30° C. for 3 days. A single colony of each transformation was inoculated into YPDG broth (1% yeast extract, 2% Bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed by 12% SDS-PAGE. As shown in FIG. 22, most TFPs could secrete human growth hormone into the culture supernatant. Among them, a strain with pYGT21-hGH was tested for the secretion level during fed-batch fermentation. Ten microliters of culture supernatant sampled at the indicated time points were analyzed by SDS-PAGE (FIG. 23). Around 500 mg/liter of human growth hormone was secreted into the culture supernatant.

EXAMPLE 20

Evaluation of Selected Core-TFPs for the Secretion of Human Caspase-1 Subunit P10

Core-TFPs selected in this invention were tested for the secretion of human caspase-1 subunit p10(hP10). The human p10 gene was PCR amplified from a human cDNA library (ES Choi, Korea Research Institute of Bioscience and Biotechnology, Korea) using primers KR-hP10-F (SEQ ID NO:210) and hP10-Sal-R (SEQ ID NO:211). The PCR product containing the hP10 gene was used for a second PCR using primers LNK40 (SEQ ID NO:23) and GT70-R (SEQ ID NO:83) to add homologous sequences with YGaSW-TFP vectors constructed in Example 18. The amplified PCR fragment was mixed 2:1 with SwaI digested YGaSW-TFP vectors and transformed into S. cerevisiae Y2805 (Mat a ura3 SUC2 pep4::HIS3 GAL1 can1) through in vivo recombination. Transformed cells were plated on UD media (0.67% yeast nitrogen base without amino acids, 0.77 g/l amino acid mixture, 2% glucose and 2% agar) and incubated at 30° C. for 3 days. A single colony of each transformation was inoculated into YPDG broth (1% yeast extract, 2% Bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed by 12% SDS-PAGE. As shown in FIG. 28, only 4 artificial TFPs containing pre-pro signals could secrete HP10 protein into the culture supernatant. As found in the case of hIGF, pro-signal was necessary for the proper secretion of human caspase-1 subunit P10 in yeast.

EXAMPLE 21

Evaluation of Selected Core-TFPs for the Secretion of Human Interleukin-32γ

Core-TFPs selected in this invention were tested for the secretion of human interleukin-32γ (hIL32γ). A gene coding for human interleukin 32 splicing variant gamma was PCR amplified from pGMT-IL32γ (D Y Yoon, Konkuk University, Korea) using primers KR-hIL32g-F (SEQ ID NO:212) and hIL32g-Sal-R (SEQ ID NO:213). The PCR product containing the hIL32γ gene was used for a second PCR using primers LNK40 (SEQ ID NO:23) and GT70-R (SEQ ID NO:83) to add homologous sequences with YGaSW-TFP vectors constructed in Example 18. The amplified PCR fragment was mixed 2:1 with SwaI digested YGaSW-TFP vectors and transformed into S. cerevisiae Y2805 (Mat a ura3 SUC2 pep4:: HIS3 GAL1 can1) through in vivo recombination. Transformed cells were plated on UD media (0.67% yeast nitrogen base without amino acids, 0.77 g/l amino acid mixture, 2% glucose and 2% agar) and incubated at 30° C. for 3 days. A single colony of each transformation was inoculated into YPDG broth (1% yeast extract, 2% Bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended in 1×SDS-PAGE sample buffer (Bio-Rad, USA) and analyzed by 12% SDS-PAGE. Among the tested TFPs, TFP3 and TFP27 were identified to be effective for the secretion of human IL-32γ (FIG. 29).

EXAMPLE 22

TFP Library from *Pichia pastoris* Selected in *Saccharomyces cerevisiae*

The TFP selection method of this invention could also be applied to other sources of the genomic or cDNA library. As an example of mRNA sources, the yeast *P. pastoris* was tested. Total RNA was isolated from yeast *P. pastoris* GS115 (Invitrogen, USA) for the construction of a cDNA library. Yeast was cultivated to mid-exponential phase in YPD media (2% yeast extract, 1% Bacto-peptone and 2% glucose). Total RNA was isolated from *P. pastoris* by a method described in Elion et al. (Elion et al., Cell 39:663 (1984)). Purification of Poly(A)$^+$ mRNA from total RNA was carried out using an Oligotex mRNA kit (Qiagen, Germany). cDNA was synthesized from the isolated mRNA using a SMART cDNA synthesis kit (BD Bioscience, USA). A specially designed primer ASA24N6 (SEQ ID NO:16) was used for the synthesis of the first strand cDNA instead of a primer included in the SMART kit as described in Example 4 (FIG. 8). Primer ASA24N6 could randomly bind to any position of mRNA due to its random hexameric sequence. Thus, most of first stranded cDNA amplified using this method contained the 5' partial sequence encoding the N-terminal part of yeast genes. The first stranded cDNA library with 5' partial sequence was used as a PCR template for double stranded cDNA synthesis with the 5' PCR primer of the SMART Kit (BD Bioscience, USA) and primer ASA24 (SEQ ID NO:17). PCR products produced using this method contain numerous 5' partial fragments of cDNA with SfiI sites at both ends. PCR conditions included one cycle of 95° C. for 20 sec, and 20 cycles of 95° C. for 30 sec, 68° C. for 6 min as recommended in the kit. Amplified cDNA was treated with phenol/chloroform/isoamyl alcohol (25:24:1) and precipitated with 2 volumes of ethanol and 0.1 volume of 3 M sodium acetate (pH 5.0). Recovered cDNA was digested with SfiI at 50° C. for 2 hours and then fractionated using agarose gel electrophoresis. 0.5 to 1 kb DNA was isolated from the gel using a gel extraction kit (Bioneer, Korea). Extracted DNA was ligated into a SfiI digested YGa-INV vector and transformed into *E. coli* DH5α. Transformed *E. coli* was plated on LB media with ampicillin (1% Bacto-peptone, 0.5% yeast extract, 1% NaCl with 50 µg/ml ampicillin) and incubated at 37° C. overnight. About 4×10$^4$ *E. coli* colonies were pooled with sterile distilled water and the total plasmids containing the cDNA library synthesized by random primer fused to the SUC2 gene were isolated by using a plasmid isolation kit (Bioneer, Korea). For the selection of a TFP library secreting invertase from yeast *P. pastoris*, library DNA was transformed into *S. cerevisiae* Y2805 Δgal1Δsuc2 (Mat a ura3 suc2::Tc190 pep4::HIS3 gal1 can1) according to a lithium acetate method (Hill et al., Nucleic Acids Res. 19:5791 (1991)). Transformed cells were spread on both UD media (0.67% yeast nitrogen base without amino acids, 0.77 g/l amino acid mixture, 2% glucose and 2% agar) and YPSGA media (1% yeast extract, 2% Bacto-peptone, 2% sucrose, 0.3% galactose, 1 µg/ml antimycin A, and 2% agar) and incubated at 30° C. for 4 to 6 days. Around 1,000 transformants were obtained from the cDNA library of *P. pastoris*. Five different transformants grown on YPSGA media were randomly selected and total DNA was isolated from cultured cells of each colony using glass beads. Then the DNA was precipitated with ethanol. Isolated DNA was retransformed into *E. coli* DH5α. *E. coli* was plated on LB media with ampicillin (1% Bacto-peptone, 0.5% yeast extract, 1% NaCl with 50 µg/ml ampicillin) and incubated at 37° C. overnight. Plasmids were isolated from transformed *E. coli* using a plasmid isolation kit (Bioneer, Korea). To analyze the sequence of each TFP obtained from the cDNA of *P. pastoris*, a sequencing primer GAL100-F (SEQ ID NO:12) binding to the GAL10 promoter was used. Nucleotide sequences were determined by Genotech Co. (Taejon, Korea) using an automated sequencing unit (ABI Prism 377; PE Biosystems, Foster City, Calif., USA). The sequences were tested on a BLAST search of the National Center for Biotechnology Information (NCBI) sequence database (ncbi.nlm.nih.gov). As a result, four different TFPs of *P. pastoris* were identified from plasmids isolated from 5 selected strains. The isolated plasmids were named pYHTS-PpTFP1, pYHTS-PpTFP2, pYHTS-PpTFP3, and pYHTS-PpTFP4. The four TFPs isolated from *P. pastoris* are, summarized in Table 6.

TABLE 6

Isolated TFPs from *Pichia pastoris*

| Number of TFP | Homologue | Number of fused amino acids(signal) | Signal sequence | SEQ ID for protein | SEQ ID for DNA |
|---|---|---|---|---|---|
| PpTFP-1 | SUN family | 101 | Pre(21aa) | 84 | 85 |
| PpTFP-2 | SED1 | 94 | Pre(17aa) | 86 | 87 |
| PpTFP-3 | Unknown | 82 | Pre(20aa) | 88 | 89 |
| PpTFP-4 | Mucin-like | 127 | Pre(18aa) | 90 | 91 |

EXAMPLE 23

Evaluation of TFPs from *Pichia pastoris* Using Human IL2

Four *Pichia pastoris* TFPs summarized in Table 6 were tested for their secretion efficiency in *S. cerevisiae* using human IL-2. Each PpTFP was PCR amplified using primer pairs, PpTFP1-F (SEQ ID NO:227) and PpTFP1-R (SEQ ID NO:228), PpTFP2-F (SEQ ID NO:229) and PpTFP2-R (SEQ ID NO:230), PpTFP3-F (SEQ ID NO:231) and PpTFP3-R (SEQ ID NO:232), PpTFP4-F (SEQ ID NO:233) and PpTFP4-R (SEQ ID NO:234) from plasmids, pYHTS-PpTFP1, pYHTS-PpTFP2, pYHTS-PpTFP3, and pYHTS-PpTFP4, respectively. Gel-purified PCR fragments were digested with SfiI and subcloned into SfiI digested YGaSW vector (FIG. 10) and the resulting plasmids were named as YGaSW-PpTFP1, YGaSW-PpTFP2, YGaSW-PpTFP3, and YGaSW-PpTFP4, respectively.

The amplified PCR fragment containing human IL-2 gene harboring homologous sequences with YGaSW-PpTFP vectors, was 2:1 mixed with SwaI digested YGaSW-PpTFP vectors and transformed into *S. cerevisiae* Y2805 (Mat a ura3 SUC2 pep4::HIS3 GAL1 can1) through in vivo recombination. Transforming cells were plated on UD media (0.67% yeast nitrogen base without amino acid, 0.77 g/l amino acid mixture, 2% glucose and 2% agar) and incubated at 30° C. for 3 days. A single colony of each transformation was inoculated into YPDG broth (1% yeast extract, 2% bacto-peptone, 1% glucose and 1% galactose) and cultivated at 30° C. for 40 hours. Culture supernatant (0.6 ml) was mixed with cold acetone for a final acetone concentration of 40%. After incubation at −20° C. for 2 hours, proteins were precipitated by centrifugation for 15 min at 10,000×g. The pellet was freeze-dried and resuspended on 1×SDS-PAGE sample buffer (Bio-Rad, USA) and analyzed in 12% of SDS-PAGE. As shown in FIG. 30, all PpTFPs secreted human interleukin-2 into culture supernatant, suggesting the compatibility of TFP between two yeasts.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method of identifying a target protein specific TFP library, said method comprising:
   (i) co-transforming a yeast cell that does not show activity of a reporter protein with a linear vector and a polynucleotide comprising a nucleic acid sequence encoding a target protein to produce a plurality of co-transformed yeast cells,
   wherein said linear vector comprises a polynucleotide fragment from a library of polynucleotide fragments and a first nucleotide sequence which encodes a portion of the reporter protein comprising a N-terminal amino acid deletion sufficient to substantially eliminate activity of the reporter protein,
   wherein said polynucleotide comprising said nucleic acid sequence encoding the target protein further comprises, at the 3' end, a second nucleotide sequence which encodes a portion of the reporter protein comprising the N-terminal amino acids deleted from said reporter protein in said linear vector, and at the 5' end, a linker DNA; and wherein said target protein is a protein that is difficult to be recombinantly produced by the yeast cell or be secreted therefrom;

(ii) incubating said co-transformed yeast cells under conditions effective to allow in vivo recombination between said linear vector and said polynucleotide comprising said nucleic acid encoding the target protein, thereby producing a fusion protein comprising the reporter protein, polynucleotide fragment from a library of polynucleotide fragments and target protein;

(iii) identifying the co-transformed yeast cell of (ii) showing an activity of the reporter protein, wherein the reporter protein is secreted as a part of the fusion protein;

(iv) identifying the polynucleotide fragment which induces the secretion of said fusion protein as a TFP from the co-transformed yeast cell identified in (iii), wherein the TFP identified in (iv) is a signal sequence.

2. The method of claim 1, wherein said polynucleotide fragments are from genomic DNA or cDNA of a plant, bacteria, yeast, fungus, or animal.

3. The method of claim 1, wherein said library of polynucleotide fragments is from recombinant DNA.

4. The method of claim 1, wherein said library of polynucleotide fragments is a library of pre-selected candidate TFPs.

5. The method of claim 4, wherein said library of pre-selected candidate TFPs is obtained by transforming a plurality of reporter protein-deficient yeast cells with a variety of vectors comprising a library of polynucleotide fragments and a polynucleotide comprising a nucleic acid sequence encoding a reporter protein, collecting cells that grow, isolating vectors from the cells, and isolating polynucleotide fragments from the vectors, thereby obtaining a TFP library comprising polynucleotide fragments which individually induce secretion of the reporter protein.

6. The method of claim 4, wherein said library of pre-selected candidate TFPs is derived from sequences identified in a genome database by searching for (i) genes containing a pre-secretion signal homologous with those of one or more previously identified TFPs; (ii) genes comprising a secretion signal sequence, or (iii) genes encoding proteins passing through the endoplasmic reticulum.

7. The method of claim 4, wherein said library of pre-selected candidate TFPs is obtained by diversifying previously identified TFPs.

8. The method of claim 4, wherein said library of pre-selected candidate TFPs is obtained by artificially designing nucleic acid fragments to have the pre and pro signal sequence swapped between previously identified TFPs.

9. The method of claim 4, wherein said library of pre-selected candidate TFPs is a library of core TFPs wherein the core TFPs are a collection of previously identified TFPs that are effective for one or more target proteins.

10. The method of claim 1, wherein said library of polynucleotide fragments is constructed by enzymatic cleavage of the DNA.

11. The method of claim 1, wherein said library of polynucleotide fragments is constructed by cDNA synthesis.

12. The method of claim 1, wherein said library of polynucleotide fragments is constructed by recombinant DNA technology.

13. The method of claim 12, wherein said recombinant DNA technology comprises unidirectional deletion.

14. The method of claim 1, wherein the polynucleotide fragments are isolated from the genome or cDNA of a yeast.

15. The method of claim 1, wherein said reporter protein is a protein that is secreted into the extracellular space.

16. The method of claim 15, wherein said reporter protein is selected from invertase, sucrase, cellulase, xylanase, maltase, amylase, glucoamylase, galactosidase, phosphatase, beta-lactamase, lipase or protease.

17. The method of claim 16, said reporter protein is invertase and the transformed yeast cells are selected for their ability to grow on sucrose or raffinose.

18. The method of claim 16, said reporter protein is amylase, the yeast cells are non-amylolytic, and the transformed cells are screened for their ability to degrade starch.

19. The method of claim 1, wherein the reporter protein provides resistance to a growth inhibitor.

20. The method of claim 1, wherein the fusion protein comprises two or more reporter proteins.

21. The method of claim 1, wherein said target protein is from a plant, animal, or microorganism.

22. The method of claim 21, wherein said target protein is a human protein.

23. The method of claim 21, wherein said target protein is a cytokine, serum protein, colony stimulating factor, growth factor, hormone, or enzyme.

24. The method of claim 21, wherein said target protein is a protein that is secreted at higher levels when fused to said TFP than when not fused to TFP.

25. The method of claim 1, wherein said linker DNA is more than 20 base pairs in length.

26. The method of claim 1, wherein said linker DNA comprises a protease recognition sequence thereby allowing cleavage at the junction of the TFP and the target protein.

27. The method of claim 26, wherein said protease recognition sequence is for yeast kex2p, mammalian furin, factor Xa, enterokinase, subtilisin, tobacco etch virus protease, thrombin, or ubiquitin hydrolase.

28. The method of claim 1, wherein said linker DNA comprises a sequence encoding an affinity tag.

29. The method of claim 1, wherein said linker DNA comprises a restriction enzyme recognition sequence.

30. The method of claim 29, wherein said linker DNA further comprises a kex2p-like protease- or a kex2p-recognition sequence.

* * * * *

SEQUENCE LISTING

```
<160> NUMBER OF SEQ ID NOS: 233

<210> SEQ ID NO 1
<211> LENGTH: 29
<212> TYPE: DNA
<213> ORGANISM: Artificial sequence
<220> FEATURE:
<223> OTHER INFORMATION: Synthetic SUC-F

<400> SEQUENCE: 1
gaattcaaaa atgcttttgc aagctttcc                                      29

<210> SEQ ID NO 2
<211> LENGTH: 30
<212> TYPE: DNA
<213> ORGANISM: Artificial sequence
<220> FEATURE:
<223> OTHER INFORMATION: Synthetic SUC-R

<400> SEQUENCE: 2
gtcgacttac tattttactt cccttacttg                                     30

<210> SEQ ID NO 3
<211> LENGTH: 24
<212> TYPE: DNA
<213> ORGANISM: Artificial sequence
<220> FEATURE:
<223> OTHER INFORMATION: Synthetic GAP-F
```

```
<400> SEQUENCE: 3
gagctcaagc ttaccagttc tcac                                          24

<210> SEQ ID NO 4
<211> LENGTH: 41
<212> TYPE: DNA
<213> ORGANISM: Artificial sequence
<220> FEATURE:
<223> OTHER INFORMATION: Synthetic SUCSS-R

<400> SEQUENCE: 4
gcggccgcac ggccgtaatg gcctgcagat attttggctg c                       41

<210> SEQ ID NO 5
<211> LENGTH: 47
<212> TYPE: DNA
<213> ORGANISM: Artificial sequence
<220> FEATURE:
<223> OTHER INFORMATION: Synthetic SUM-F

<400> SEQUENCE: 5
gcggccgcct cggccctaga taaaaggtca atgacaaacg aaactag                 47

<210> SEQ ID NO 6
<211> LENGTH: 33
<212> TYPE: DNA
<213> ORGANISM: Artificial sequence
<220> FEATURE:
<223> OTHER INFORMATION: Synthetic HSA-F

<400> SEQUENCE: 6
ggccattacg gccgtgatgc acacaagagt gag                                33

<210> SEQ ID NO 7
<211> LENGTH: 33
<212> TYPE: DNA
<213> ORGANISM: Artificial sequence
<220> FEATURE:
<223> OTHER INFORMATION: Synthetic HSA-R

<400> SEQUENCE: 7
ggccgaggcg gcctaagcct aaggcagctt gac                                33

<210> SEQ ID NO 8
<211> LENGTH: 35
<212> TYPE: DNA
<213> ORGANISM: Artificial sequence
<220> FEATURE:
<223> OTHER INFORMATION: Synthetic IL2-F

<400> SEQUENCE: 8
ggccattacg gccgtgcacc tacttcaagt tctac                              35

<210> SEQ ID NO 9
<211> LENGTH: 33
<212> TYPE: DNA
<213> ORGANISM: Artificial sequence
<220> FEATURE:
<223> OTHER INFORMATION: Synthetic IL2-R

<400> SEQUENCE: 9
ggccgaggcg gccagttagt gttgagatga tgc                                33

<210> SEQ ID NO 10
<211> LENGTH: 58
```

<212> TYPE: DNA
<213> ORGANISM: Artificial sequence
<220> FEATURE:
<223> OTHER INFORMATION: Synthetic SfiI-SUC-F

<400> SEQUENCE: 10
gaattcaaaa ggccattacg gccgcggccg cctcggccct agataaaagg tcaatgac     58

<210> SEQ ID NO 11
<211> LENGTH: 29
<212> TYPE: DNA
<213> ORGANISM: Artificial sequence
<220> FEATURE:
<223> OTHER INFORMATION: Synthetic SUC-Xho-R

<400> SEQUENCE: 11
ggctcgagct attttacttc ccttacttg                                     29

<210> SEQ ID NO 12
<211> LENGTH: 26
<212> TYPE: DNA
<213> ORGANISM: Artificial sequence
<220> FEATURE:
<223> OTHER INFORMATION: Synthetic GAL100-F

<400> SEQUENCE: 12
gatatgtata tggtggtaat gccatg                                        26

<210> SEQ ID NO 13
<211> LENGTH: 41
<212> TYPE: DNA
<213> ORGANISM: Artificial sequence
<220> FEATURE:
<223> OTHER INFORMATION: Synthetic Xho-F0-R

<400> SEQUENCE: 13
ctagggccga ggcggccctc gagggccgta atggcctttt g                       41

<210> SEQ ID NO 14
<211> LENGTH: 42
<212> TYPE: DNA
<213> ORGANISM: Artificial sequence
<220> FEATURE:
<223> OTHER INFORMATION: Synthetic Xho-F1-R

<400> SEQUENCE: 14
ctagggccga ggcggccgct cgagggccgt aatggccttt tg                      42

<210> SEQ ID NO 15
<211> LENGTH: 43
<212> TYPE: DNA
<213> ORGANISM: Artificial sequence
<220> FEATURE:
<223> OTHER INFORMATION: Synthetic Xho-F2-R

<400> SEQUENCE: 15
ctagggccga ggcggccgtc tcgagggccg taatggcctt ttg                     43

<210> SEQ ID NO 16
<211> LENGTH: 30
<212> TYPE: DNA
<213> ORGANISM: Artificial sequence
<220> FEATURE:
<223> OTHER INFORMATION: Synthetic ASA24N6
<220> FEATURE:
<221> NAME/KEY: misc_feature
<222> LOCATION: (25)..(30)

```
<223> OTHER INFORMATION: n is a, c, g, or t

<400> SEQUENCE: 16
gccagcagag gccgaggcgg ccagnnnnnn                                              30

<210> SEQ ID NO 17
<211> LENGTH: 24
<212> TYPE: DNA
<213> ORGANISM: Artificial sequence
<220> FEATURE:
<223> OTHER INFORMATION: Synthetic ASA24

<400> SEQUENCE: 17
gccagcagag gccgaggcgg ccag                                                    24

<210> SEQ ID NO 18
<211> LENGTH: 65
<212> TYPE: DNA
<213> ORGANISM: Artificial sequence
<220> FEATURE:
<223> OTHER INFORMATION: Synthetic INV45-F

<400> SEQUENCE: 18
gcggccgcct cggcctctgc tggcctcgcc ttagataaaa gatttaaatg acaccgtatg            60
gggta                                                                         65

<210> SEQ ID NO 19
<211> LENGTH: 35
<212> TYPE: DNA
<213> ORGANISM: Artificial sequence
<220> FEATURE:
<223> OTHER INFORMATION: Synthetic KR-target-F
<220> FEATURE:
<221> NAME/KEY: misc_feature
<222> LOCATION: (19)..(35)
<223> OTHER INFORMATION: n is a, c, g, or t

<400> SEQUENCE: 19
ctcgccttag ataaaagann nnnnnnnnn nnnnn                                         35

<210> SEQ ID NO 20
<211> LENGTH: 35
<212> TYPE: DNA
<213> ORGANISM: Artificial sequence
<220> FEATURE:
<223> OTHER INFORMATION: Synthetic Target-INV-R
<220> FEATURE:
<221> NAME/KEY: misc_feature
<222> LOCATION: (19)..(35)
<223> OTHER INFORMATION: n is a, c, g, or t

<400> SEQUENCE: 20
cattgaacgc ttgtccaann nnnnnnnnn nnnnn                                         35

<210> SEQ ID NO 21
<211> LENGTH: 38
<212> TYPE: DNA
<213> ORGANISM: Artificial sequence
<220> FEATURE:
<223> OTHER INFORMATION: Synthetic KR-Inv-F

<400> SEQUENCE: 21
ttggacaagc gttcaatgac aaacgaaact agcgatag                                     38

<210> SEQ ID NO 22
<211> LENGTH: 25
```

```
<212> TYPE: DNA
<213> ORGANISM: Artificial sequence
<220> FEATURE:
<223> OTHER INFORMATION: Synthetic Inv500-R

<400> SEQUENCE: 22
tcataatcca tttttgagaa ggttc                                           25

<210> SEQ ID NO 23
<211> LENGTH: 40
<212> TYPE: DNA
<213> ORGANISM: Artificial sequence
<220> FEATURE:
<223> OTHER INFORMATION: Synthetic LNK40

<400> SEQUENCE: 23
ggccgcctcg gcctctgctg gcctcgcctt agataaaaga                           40

<210> SEQ ID NO 24
<211> LENGTH: 30
<212> TYPE: DNA
<213> ORGANISM: Artificial sequence
<220> FEATURE:
<223> OTHER INFORMATION: Synthetic KR-CalB-F

<400> SEQUENCE: 24
ttggacaagc gtctaccttc cggttcggac                                      30

<210> SEQ ID NO 25
<211> LENGTH: 38
<212> TYPE: DNA
<213> ORGANISM: Artificial sequence
<220> FEATURE:
<223> OTHER INFORMATION: Synthetic CalB-Inv-R

<400> SEQUENCE: 25
cattgaacgc ttgtccaagg gggtgacgat gccggagc                             38

<210> SEQ ID NO 26
<211> LENGTH: 35
<212> TYPE: DNA
<213> ORGANISM: Artificial sequence
<220> FEATURE:
<223> OTHER INFORMATION: Synthetic Target-CalB-R
<220> FEATURE:
<221> NAME/KEY: misc_feature
<222> LOCATION: (19)..(35)
<223> OTHER INFORMATION: n is a, c, g, or t

<400> SEQUENCE: 26
aggtagacgc ttgtccaann nnnnnnnnn nnnnn                                 35

<210> SEQ ID NO 27
<211> LENGTH: 38
<212> TYPE: DNA
<213> ORGANISM: Artificial sequence
<220> FEATURE:
<223> OTHER INFORMATION: Synthetic KR-IL2-F

<400> SEQUENCE: 27
ctcgccttag ataaaagagc acctacttca agttctac                             38

<210> SEQ ID NO 28
<211> LENGTH: 38
<212> TYPE: DNA
<213> ORGANISM: Artificial sequence
<220> FEATURE:
```

<223> OTHER INFORMATION: Synthetic IL2-INV-R

<400> SEQUENCE: 28
cattgaacgc ttgtccaaag ttagtgttga gatgatgc                                38

<210> SEQ ID NO 29
<211> LENGTH: 217
<212> TYPE: PRT
<213> ORGANISM: Artificial sequence
<220> FEATURE:
<223> OTHER INFORMATION: Saccharomyces cerevisiae TFP9-AA

<400> SEQUENCE: 29

```
Met Val Phe Gly Gln Leu Tyr Ala Leu Phe Ile Phe Thr Leu Ser Cys
1               5                   10                  15

Cys Ile Ser Lys Thr Val Gln Ala Asp Ser Ser Lys Glu Ser Ser Ser
            20                  25                  30

Phe Ile Ser Phe Asp Lys Glu Ser Asn Trp Asp Thr Ile Ser Thr Ile
        35                  40                  45

Ser Ser Thr Ala Asp Val Ile Ser Ser Val Asp Ser Ala Ile Ala Val
    50                  55                  60

Phe Glu Phe Asp Asn Phe Ser Leu Leu Asp Asn Leu Met Ile Asp Glu
65                  70                  75                  80

Glu Tyr Pro Phe Phe Asn Arg Phe Phe Ala Asn Asp Val Ser Leu Thr
                85                  90                  95

Val His Asp Asp Ser Pro Leu Asn Ile Ser Gln Ser Leu Ser Pro Ile
            100                 105                 110

Met Glu Gln Phe Thr Val Asp Glu Leu Pro Glu Ser Ala Ser Asp Leu
        115                 120                 125

Leu Tyr Glu Tyr Ser Leu Asp Asp Lys Ser Ile Val Leu Phe Lys Phe
    130                 135                 140

Thr Ser Asp Ala Tyr Asp Leu Lys Lys Leu Asp Glu Phe Ile Asp Ser
145                 150                 155                 160

Cys Leu Ser Phe Leu Glu Asp Lys Ser Gly Asp Asn Leu Thr Val Val
                165                 170                 175

Ile Asn Ser Leu Gly Trp Ala Phe Glu Asp Asp Gly Asp Asp Glu
            180                 185                 190

Tyr Ala Thr Glu Glu Thr Leu Ser His His Asp Asn Asn Lys Gly Lys
        195                 200                 205

Glu Gly Asp Asp Leu Ala Ala Ser Ala
    210                 215
```

<210> SEQ ID NO 30
<211> LENGTH: 728
<212> TYPE: DNA
<213> ORGANISM: Artificial sequence
<220> FEATURE:
<223> OTHER INFORMATION: Saccharomyces cerevisiae TFP9-nt

<400> SEQUENCE: 30
ggccattacg gccggggatt gataataacc actgctgtga ctatatataa taagaatcga     60
actgtaaagt taaagcaatg gtgttcggtc agctgtatgc ccttttcatc ttcacgttat    120
catgttgtat ttccaaaact gtgcaagcag attcatccaa ggaaagctct tcctttattt    180
cgttcgacaa agagagtaac tgggatacca tcagcactat atcttcaacg gcagatgtta    240
tatcatccgt tgacagtgct atcgctgttt ttgaatttga caatttctca ttattggaca    300
acttgatgat tgacgaagaa taccattct tcaatagatt ctttgccaat gatgtcagtt    360

```
taactgttca tgacgattcg cctttgaaca tctctcaatc attatctccc attatggaac    420
aatttactgt ggatgaatta cctgaaagtg cctctgactt actatatgaa tactccttag    480
atgataaaag catcgttttg ttcaagttta cctcggatgc ctacgatttg aaaaaattag    540
atgaatttat tgattcttgc ttatcgtttt tggaggataa atctggcgac aatttgactg    600
tggttattaa ctctcttggt tgggcttttg aagatgaaga tggtgacgat gaatatgcaa    660
cagaagagac tttgagccat catgataaca acaagggtaa agaaggcgac gatctggccg    720
cctcggcc                                                              728

<210> SEQ ID NO 31
<211> LENGTH: 127
<212> TYPE: PRT
<213> ORGANISM: Artificial sequence
<220> FEATURE:
<223> OTHER INFORMATION: Saccharomyces cerevisiae TFP13-aa

<400> SEQUENCE: 31

Met Lys Phe Ser Thr Ala Val Thr Thr Leu Ile Ser Ser Gly Ala Ile
1               5                   10                  15

Val Ser Ala Leu Pro His Val Asp Val His Gln Glu Asp Ala His Gln
            20                  25                  30

His Lys Arg Ala Val Ala Tyr Lys Tyr Val Tyr Glu Thr Val Val Val
        35                  40                  45

Asp Ser Asp Gly His Thr Val Thr Pro Ala Ala Ser Glu Val Ala Thr
    50                  55                  60

Ala Ala Thr Ser Ala Ile Ile Thr Thr Ser Val Leu Ala Pro Thr Ser
65                  70                  75                  80

Ser Ala Ala Ala Gly Ile Ala Ala Ser Ile Ala Val Ser Ser Ala Ala
                85                  90                  95

Leu Ala Lys Asn Glu Lys Ile Ser Asp Ala Ala Ala Ser Ala Thr Ala
            100                 105                 110

Ser Thr Ser Gln Gly Ala Ser Ser Ser Ser Leu Ala Ala Ser Ala
        115                 120                 125

<210> SEQ ID NO 32
<211> LENGTH: 618
<212> TYPE: DNA
<213> ORGANISM: Artificial sequence
<220> FEATURE:
<223> OTHER INFORMATION: Saccharomyces cerevisiae TFP13-aa
<220> FEATURE:
<221> NAME/KEY: misc_feature
<222> LOCATION: (42)..(42)
<223> OTHER INFORMATION: n is a, c, g, or t

<400> SEQUENCE: 32
ggccattacg gccgggggatt caaatatata tatctactca gnttgaataa gacactatag    60
caagaccatt tgaactgaaa gaaacagttt ctttgctccc ctctcgaatt ccaactattt   120
acagtccttc ctttataaaa attaactagc gagcaagaaa acatttgttt agtgctaccc   180
aactacttac attcctttaa aaaccacaat atttaagtta acctgagctt tatttttaaa   240
atgaaattct caactgccgt tactacgttg attagttctg gtgccatcgt gtctgcttta   300
ccacacgtgg atgttcacca agaagatgcc caccaacata gagggccgt tgcgtacaaa    360 tacgtttacg aaactgttgt tgtcgattct gatggccaca ctgtaactcc tgctgcttca    420
gaagtcgcta ctgctgctac ctctgctatc attacaacat ctgtgttggc tccaacctcc    480
```

```
tccgcagccg ctgggatagc cgcttccatt gctgtttcat ctgctgcctt agccaagaat      540
gagaaaatct ctgatgccgc tgcatctgcc actgcctcaa catctcaagg ggcatcctcc      600
tcctccctgg ccgcctcg                                                    618
```

```
<210> SEQ ID NO 33
<211> LENGTH: 68
<212> TYPE: PRT
<213> ORGANISM: Artificial sequence
<220> FEATURE:
<223> OTHER INFORMATION: Saccharomyces cerevisiae TFP17-AA

<400> SEQUENCE: 33
```

Met Lys Phe Ser Ser Val Thr Ala Ile Thr Leu Ala Thr Val Ala Thr
1               5                   10                  15

Val Ala Thr Ala Lys Lys Gly Glu His Asp Phe Thr Thr Thr Leu Thr
            20                  25                  30

Leu Ser Ser Asp Gly Ser Leu Thr Thr Thr Ser Thr His Thr
        35                  40                  45

His Lys Tyr Gly Lys Phe Asn Lys Thr Ser Lys Ser Lys Thr Pro Trp
    50                  55                  60

Ala Ala Ser Ala
65

```
<210> SEQ ID NO 34
<211> LENGTH: 391
<212> TYPE: DNA
<213> ORGANISM: Artificial sequence
<220> FEATURE:
<223> OTHER INFORMATION: Saccharomyces cerevisiae TFP17-nt

<400> SEQUENCE: 34
```

```
ggccattacg gccggggttt cttctctttt tttcttttt gaataaagaa ttttccttta      60
aggagtaact taagcattta gctgcacatt aaacactttt tttttactt ctaactcaca      120 cacttttgga agaacattta ttttttcgac cttcttccc aaatacccag cgctttataa      180
ttgaaatatg aagttctctt ctgttactgc tattactcta gccaccgttg ccaccgttgc      240
cactgctaag aagggtgaac atgatttcac taccacttta actttgtcat cggacggtag      300
tttaactact accacctcta ctcataccac tcacaagtat ggtaagttca acaagacttc      360
caagtccaag acccctgggccgcctcggc c                                      391
```

```
<210> SEQ ID NO 35
<211> LENGTH: 199
<212> TYPE: PRT
<213> ORGANISM: Artificial sequence
<220> FEATURE:
<223> OTHER INFORMATION: Saccharomyces cerevisiae TFP18-aa

<400> SEQUENCE: 35
```

Met Gln Phe Lys Asn Ala Leu Thr Ala Thr Ala Ile Leu Ser Ala Ser
1               5                   10                  15

Ala Leu Ala Asn Ser Thr Thr Ser Ile Pro Ser Ser Cys Ser Ile Gly
            20                  25                  30

Thr Ser Ala Thr Ala Thr Ala Gln Ala Asp Leu Asp Lys Ile Ser Gly
        35                  40                  45

Cys Ser Thr Ile Val Gly Asn Leu Thr Ile Thr Gly Asp Leu Gly Ser
    50                  55                  60

Ala Ala Leu Ala Ser Ile Gln Glu Ile Asp Gly Ser Leu Thr Ile Phe
65                  70                  75                  80

```
Asn Ser Ser Ser Leu Ser Ser Phe Ser Ala Asp Ser Ile Lys Lys Ile
                85                  90                  95

Thr Gly Asp Leu Asn Met Gln Glu Leu Ile Ile Leu Thr Ser Ala Ser
            100                 105                 110

Phe Gly Ser Leu Gln Glu Val Asp Ser Ile Asn Met Val Thr Leu Pro
        115                 120                 125

Ala Ile Ser Thr Phe Ser Thr Asp Leu Gln Asn Ala Asn Asn Ile Ile
    130                 135                 140

Val Ser Asp Thr Thr Leu Glu Ser Val Glu Gly Phe Ser Thr Leu Lys
145                 150                 155                 160

Lys Val Asn Val Phe Asn Ile Asn Asn Asn Arg Tyr Leu Asn Ser Phe
                165                 170                 175

Gln Ser Ser Leu Glu Ser Val Ser Asp Ser Leu Gln Phe Ser Ser Asn
            180                 185                 190

Gly Asp Leu Ala Ala Ser Ala
        195
```

<210> SEQ ID NO 36
<211> LENGTH: 760
<212> TYPE: DNA
<213> ORGANISM: Artificial sequence
<220> FEATURE:
<223> OTHER INFORMATION: Saccharomyces cerevisiae TFP18-nt

<400> SEQUENCE: 36

```
ggccattacg gccgaaaaga aattaaataa aagagttaat cgttcattcg cttctacaca    60
gtttaatctt ttccattttt ctttcaacaa gtcccttgga gctatcaaga atacgtttat   120
ttgactttta aagatctagt tttaatttta ctattattcc gcaatgcaat tcaagaacgc   180
tttgactgct actgctattc taagtgcctc cgctctagct aactcaacta cttctattcc   240
atcttcatgt agtattggta cttctgccac tgctactgct caagctgatt tggacaaaat   300
ctccggttgt agtaccattg ttggtaactt gaccatcacc ggtgacttgg gttccgctgc   360
tttggctagt atccaagaga ttgatggttc cttgactatc ttcaactcca gttctttatc   420
ttctttctcc gctgactcta tcaagaaaat caccggtgat ttgaacatgc aagaattgat   480
cattttgacc agtgcttctt tcggttcttt gcaagaagta gactccatta acatggtgac   540
tttgcctgcc atttctacct ctccaccgat ttacaaaat gctaacaaca ttattgtttc   600
tgacaccact ttggaaagtg tcgaaggttt ctccactttg aagaaggtta atgtttttaa   660
catcaacaac aacagatatc taaactcttt ccaatcttcc ttggaaagtg tctctgactc   720
tttacaattc tcttccaacg gtgacctggc cgcctcggcc                         760
```

<210> SEQ ID NO 37
<211> LENGTH: 148
<212> TYPE: PRT
<213> ORGANISM: Artificial sequence
<220> FEATURE:
<223> OTHER INFORMATION: Saccharomyces cerevisiae TFP19-aa

<400> SEQUENCE: 37

```
Met Val Ser Lys Thr Trp Ile Cys Gly Phe Ile Ser Ile Ile Thr Val
1               5                   10                  15

Val Gln Ala Leu Ser Cys Glu Lys His Asp Val Leu Lys Lys Tyr Gln
            20                  25                  30

Val Gly Lys Phe Ser Ser Leu Thr Ser Thr Glu Arg Asp Thr Pro Pro
        35                  40                  45
```

Ser Thr Thr Ile Glu Lys Trp Trp Ile Asn Val Cys Glu Glu His Asn
    50                  55                  60

Val Glu Pro Pro Glu Glu Cys Lys Lys Asn Asp Met Leu Cys Gly Leu
65                  70                  75                  80

Thr Asp Val Ile Leu Pro Gly Lys Asp Ala Ile Thr Thr Gln Ile Ile
                85                  90                  95

Asp Phe Asp Lys Asn Ile Gly Phe Asn Val Glu Glu Thr Glu Ser Ala
                100                 105                 110

Leu Thr Leu Thr Leu Lys Gly Ala Thr Trp Gly Ala Asn Ser Phe Asp
            115                 120                 125

Ala Lys Leu Glu Phe Gln Cys Asn Asp Asn Met Lys Gln Asp Glu Leu
        130                 135                 140

Ala Ala Ser Ala
145

<210> SEQ ID NO 38
<211> LENGTH: 464
<212> TYPE: DNA
<213> ORGANISM: Artificial sequence
<220> FEATURE:
<223> OTHER INFORMATION: Saccharomyces cerevisiae TFP19-nt

<400> SEQUENCE: 38
ggccattacg gccggggacg atggtatcga agacttggat atgtggcttc atcagtataa      60
ttacagtggt acaggccttg tcctgcgaga agcatgatgt attgaaaaag tatcaggtgg     120
gaaaatttag ctcactaact tctacggaaa gggatactcc gccaagcaca actattgaaa    180
agtggtggat aaacgtttgc gaagagcata cgtagaacc tcctgaagaa tgtaaaaaaa    240
atgacatgct atgtggttta acagatgtca tcttgcccgg taaggatgct atcaccactc    300
aaattataga ttttgacaaa acattggct tcaatgtcga ggaaactgag agtgcgctta    360
cattgacact aaaaggcgct acgtggggcg ccaattcttt tgacgcaaaa ctagaatttc    420
agtgtaatga caatatgaaa caagacgaac tggccgcctc ggcc                    464

<210> SEQ ID NO 39
<211> LENGTH: 187
<212> TYPE: PRT
<213> ORGANISM: Artificial sequence
<220> FEATURE:
<223> OTHER INFORMATION: Saccharomyces cerevisiae TFP20-aa

<400> SEQUENCE: 39

Met Leu Phe Lys Ser Leu Ser Lys Leu Ala Thr Ala Ala Phe Phe
1               5                   10                  15

Ala Gly Val Ala Thr Ala Asp Asp Val Pro Ala Ile Glu Val Val Gly
            20                  25                  30

Asn Lys Phe Phe Tyr Ser Asn Asn Gly Ser Gln Phe Tyr Ile Arg Gly
        35                  40                  45

Val Ala Tyr Gln Ala Asp Thr Ala Asn Glu Thr Ser Gly Ser Thr Val
    50                  55                  60

Asn Asp Pro Leu Ala Asn Tyr Glu Ser Cys Ser Arg Asp Ile Pro Tyr
65                  70                  75                  80

Leu Lys Lys Leu Asn Thr Asn Val Ile Arg Val Tyr Ala Ile Asn Thr
                85                  90                  95

Thr Leu Asp His Ser Glu Cys Met Lys Ala Leu Asn Asp Ala Asp Ile
                100                 105                 110

Tyr Val Ile Ala Asp Leu Ala Ala Pro Ala Thr Ser Ile Asn Arg Asp
            115                 120                 125

Asp Pro Thr Trp Thr Val Asp Leu Phe Asn Ser Tyr Lys Thr Val Val
        130                 135                 140

Asp Thr Phe Ala Asn Tyr Thr Asn Val Leu Gly Phe Phe Ala Gly Asn
145                 150                 155                 160

Glu Val Thr Asn Asn Tyr Thr Asn Thr Asp Ala Ser Ala Phe Val Lys
                165                 170                 175

Ala Ala Ile Arg Asp Val Leu Ala Ala Ser Ala
            180                 185

<210> SEQ ID NO 40
<211> LENGTH: 664
<212> TYPE: DNA
<213> ORGANISM: Artificial sequence
<220> FEATURE:
<223> OTHER INFORMATION: Saccharomyces cerevisiae TFP20-nt

<400> SEQUENCE: 40
ggccattacg gccggggtgt cgttttatta agctatttca aaatcagttt ttatttttaa      60
agtctgataa acaaaaaaca acaaacacag ctaaatctca acaatgttgt ttaaatccct     120
ttcaaagtta gcaaccgctg ctgctttttt tgctggcgtc gcaactgcgg acgatgttcc     180
agcgattgaa gttgttggta ataagttttt ctactccaac aacggtagtc agttctacat     240
aagaggtgtt gcttatcagg ctgataccgc taatgaaact agcggatcta ctgtcaacga     300
tcctttggcc aattatgaga gttgttccag agatattcca tacctcaaaa aattgaacac     360
aaatgttatc cgtgtctacg ctatcaatac cactctagat cactccgaat gtatgaaggc     420
tttgaatgat gctgacatct atgtcatcgc tgatttagca gctccagcca cctctatcaa     480
tagagacgat ccaacttgga ctgttgactt gttcaacagc tacaaaaccg ttgttgacac     540
ttttgctaat tacaccaacg ttttgggttt cttcgccggt aatgaagtta ctaacaatta     600
caccaacaca gatgcatctg ctttcgtgaa ggcagctatt agagacgtcc tggccgcctc     660
ggcc                                                                  664

<210> SEQ ID NO 41
<211> LENGTH: 55
<212> TYPE: PRT
<213> ORGANISM: Artificial sequence
<220> FEATURE:
<223> OTHER INFORMATION: Saccharomyces cerevisiae TFP21-aa

<400> SEQUENCE: 41

Met Leu Gln Ser Val Val Phe Phe Ala Leu Leu Thr Phe Ala Ser Ser
1               5                   10                  15

Val Ser Ala Ile Tyr Ser Asn Asn Thr Val Ser Thr Thr Thr Thr Leu
            20                  25                  30

Ala Pro Ser Tyr Ser Leu Val Pro Gln Glu Thr Thr Ile Ser Tyr Ala
        35                  40                  45

Asp Asp Leu Ala Ala Ser Ala
    50                  55

<210> SEQ ID NO 42
<211> LENGTH: 407
<212> TYPE: DNA
<213> ORGANISM: Artificial sequence
<220> FEATURE:
<223> OTHER INFORMATION: Saccharomyces cerevisiae TFP21-nt

<400> SEQUENCE: 42

```
ggccattacg gccggggaag caactagttt agcacaacat ccaaccaaga ggtttctcgc    60
gtatttctct catttttta cccatttac aaatttttt tgctatttga gccatagtac    120
ccattaatag gtctcgtcca ttcccttgtt ttttttat tgtttcaatt acactacata    180
attaaaaatc acatcacttt cactctcacc ttagtcgttc tttatcaacc aaaaataaaa    240
aaatgcttca atccgttgtc ttttcgctc tttaacctt cgcaagttct gtgtcagcga    300
tttattcaaa caatactgtt tctacaacta ccactttagc gcccagctac tccttggtgc    360
cccaagagac taccatatcg tacgccgacg acctggccgc ctcggcc               407
```

<210> SEQ ID NO 43
<211> LENGTH: 190
<212> TYPE: PRT
<213> ORGANISM: Artificial sequence
<220> FEATURE:
<223> OTHER INFORMATION: Saccharomyces cerevisiae TFP25-aa

<400> SEQUENCE: 43

```
Met Asn Trp Leu Phe Leu Val Ser Leu Val Phe Phe Cys Gly Val Ser
1               5                   10                  15

Thr His Pro Ala Leu Ala Met Ser Ser Asn Arg Leu Leu Lys Leu Ala
            20                  25                  30

Asn Lys Ser Pro Lys Lys Ile Ile Pro Leu Lys Asp Ser Ser Phe Glu
        35                  40                  45

Asn Ile Leu Ala Pro Pro His Glu Asn Ala Tyr Ile Val Ala Leu Phe
    50                  55                  60

Thr Ala Thr Ala Pro Glu Ile Gly Cys Ser Leu Cys Leu Glu Leu Glu
65                  70                  75                  80

Ser Glu Tyr Asp Thr Ile Val Ala Ser Trp Phe Asp Asp His Pro Asp
                85                  90                  95

Ala Lys Ser Ser Asn Ser Asp Thr Ser Ile Phe Phe Thr Lys Val Asn
            100                 105                 110

Leu Glu Asp Pro Ser Lys Thr Ile Pro Lys Ala Phe Gln Phe Phe Gln
        115                 120                 125

Leu Asn Asn Val Pro Arg Leu Phe Ile Phe Lys Pro Asn Ser Pro Ser
    130                 135                 140

Ile Leu Asp His Ser Val Ile Ser Ile Ser Thr Asp Thr Gly Ser Glu
145                 150                 155                 160

Arg Met Lys Gln Ile Ile Gln Ala Ile Lys Gln Phe Ser Gln Val Asn
                165                 170                 175

Asp Phe Ser Leu His Leu Pro Val Gly Leu Ala Ala Ser Ala
            180                 185                 190
```

<210> SEQ ID NO 44
<211> LENGTH: 654
<212> TYPE: DNA
<213> ORGANISM: Artificial sequence
<220> FEATURE:
<223> OTHER INFORMATION: Saccharomyces cerevisiae TFP25-nt

<400> SEQUENCE: 44

```
ggccattacg gccgggggaa taccaggcac acgctcttcg aacactgaac cacacgcgtc    60
cgcatcaaac tcttcctccc aaacatgaat tggctgtttt tggtctcgct ggttttcttc    120
tgcggcgtgt caacccatcc tgccctggca atgtccagca acagactact aaagctggct    180
aataaatctc ccaagaaaat tataccctctg aaggactcaa gttttgaaaa catcttggca    240
```

```
ccacctcacg aaaatgccta tatagttgct ctgtttactg ccacagcgcc cgaaattggc      300
tgttctctgt gtctcgagct agaatccgaa tacgacacca tagtggcctc ctggtttgat      360
gatcatccgg atgcaaaatc gtccaattcc gatacatcta ttttcttcac aaaggtcaat      420
ttggaggacc cttctaagac cattcctaaa gcgttccagt ttttccaact aaacaatgtt      480
cctagattgt tcatcttcaa accaaactct ccctctattc tggaccacag cgtgatcagt      540
atttccactg atactggctc agaaagaatg aagcaaatca tacaagccat taagcagttc      600
tcgcaagtaa acgacttctc tttacactta cctgtgggtc tggccgcctc ggcc           654
```

```
<210> SEQ ID NO 45
<211> LENGTH: 89
<212> TYPE: PRT
<213> ORGANISM: Artificial sequence
<220> FEATURE:
<223> OTHER INFORMATION: Saccharomyces cerevisiae TFP27-aa

<400> SEQUENCE: 45

Met Lys Leu Ser Ala Leu Leu Ala Leu Ser Ala Ser Thr Ala Val Leu
1               5                   10                  15

Ala Ala Pro Ala Val His His Ser Asp Asn His His Asn Asp Lys
            20                  25                  30

Arg Ala Val Val Thr Val Thr Gln Tyr Val Asn Ala Asp Gly Ala Val
        35                  40                  45

Val Ile Pro Ala Ala Thr Thr Ala Thr Ser Ala Ala Ala Asp Gly Lys
    50                  55                  60

Val Glu Ser Val Ala Ala Ala Thr Thr Thr Leu Ser Ser Thr Ala Ala
65                  70                  75                  80

Ala Ala Thr Thr Leu Ala Ala Ser Ala
                85
```

```
<210> SEQ ID NO 46
<211> LENGTH: 470
<212> TYPE: DNA
<213> ORGANISM: Artificial sequence
<220> FEATURE:
<223> OTHER INFORMATION: Saccharomyces cerevisiae TFP27-nt

<400> SEQUENCE: 46
ggccattacg gccggggacg ctcctttcat cggtaactaa gaagaaaaaa aaaaagtac       60 gaccacacaa tttccagtgt attcattcct taaacttcgt ttattttta ttcattcatt      120 catttttatt tgaatataac caactactag tccttccttt aaacaaaaat ttaccctccc      180 ttaattttc aagaaattcc agtatgaaat tatccgctct attagcttta tcagcctcca      240
ccgccgtctt ggccgctcca gctgtccacc atagtgacaa ccaccaccac aacgacaagc      300
gtgccgttgt caccgttact cagtacgtca acgcagacgg cgctgttgtt attccagctg      360
ccaccaccgc tacctcggcg gctgctgatg gaaaggtcga gtctgttgct gctgccacca      420
ctactttgtc ctcgactgcc gccgccgcta caaccctggc cgcctcggcc                 470
```

```
<210> SEQ ID NO 47
<211> LENGTH: 33
<212> TYPE: DNA
<213> ORGANISM: Artificial sequence
<220> FEATURE:
<223> OTHER INFORMATION: Synthetic BamH-YGR-F

<400> SEQUENCE: 47
```
ccggatccat ggtgttcggt cagctgtatg ccc                                33

<210> SEQ ID NO 48
<211> LENGTH: 34
<212> TYPE: DNA
<213> ORGANISM: Artificial sequence
<220> FEATURE:
<223> OTHER INFORMATION: Synthetic BamH-SIM-F

<400> SEQUENCE: 48
cggatccatg aaattctcaa ctgccgttac tacg                               34

<210> SEQ ID NO 49
<211> LENGTH: 31
<212> TYPE: DNA
<213> ORGANISM: Artificial sequence
<220> FEATURE:
<223> OTHER INFORMATION: Synthetic BamH-YNL-F

<400> SEQUENCE: 49
ccggatccat gaagttctct tctgttactg c                                  31

<210> SEQ ID NO 50
<211> LENGTH: 31
<212> TYPE: DNA
<213> ORGANISM: Artificial sequence
<220> FEATURE:
<223> OTHER INFORMATION: Synthetic BamH-ECM-F

<400> SEQUENCE: 50
ccggatccat gcaattcaag aacgctttga c                                  31

<210> SEQ ID NO 51
<211> LENGTH: 34
<212> TYPE: DNA
<213> ORGANISM: Artificial sequence
<220> FEATURE:
<223> OTHER INFORMATION: Synthetic BamH-ATG-F

<400> SEQUENCE: 51
ccggatccat ggtatcgaag acttggatat gtgg                               34

<210> SEQ ID NO 52
<211> LENGTH: 37
<212> TYPE: DNA
<213> ORGANISM: Artificial sequence
<220> FEATURE:
<223> OTHER INFORMATION: Synthetic BamH-GAS-F

<400> SEQUENCE: 52
ccggatccat gttgtttaaa tccctttcaa agttagc                            37

<210> SEQ ID NO 53
<211> LENGTH: 34
<212> TYPE: DNA
<213> ORGANISM: Artificial sequence
<220> FEATURE:
<223> OTHER INFORMATION: Synthetic BamH-YOR-F

<400> SEQUENCE: 53
ccggatccat gcttcaatcc gttgtcttttt tcgc                              34

<210> SEQ ID NO 54
<211> LENGTH: 36
<212> TYPE: DNA
<213> ORGANISM: Artificial sequence

```
<220> FEATURE:
<223> OTHER INFORMATION: Synthetic BamH-OST-F

<400> SEQUENCE: 54
ccggatccat gaattggctg tttttggtct cgctgg                                36

<210> SEQ ID NO 55
<211> LENGTH: 32
<212> TYPE: DNA
<213> ORGANISM: Artificial sequence
<220> FEATURE:
<223> OTHER INFORMATION: Synthetic BamH-UTH-F

<400> SEQUENCE: 55
ccggatccat gtgtttcctt ctcgagacct cg                                   32

<210> SEQ ID NO 56
<211> LENGTH: 43
<212> TYPE: DNA
<213> ORGANISM: Artificial sequence
<220> FEATURE:
<223> OTHER INFORMATION: Synthetic IL2-TGA-R

<400> SEQUENCE: 56
gtcactccgt tcaagtcgac tcaagttagt gttgagatga tgc                       43

<210> SEQ ID NO 57
<211> LENGTH: 24
<212> TYPE: DNA
<213> ORGANISM: Artificial sequence
<220> FEATURE:
<223> OTHER INFORMATION: Synthetic Sac-GAL-F

<400> SEQUENCE: 57
gagctcatcg cttcgctgat taat                                            24

<210> SEQ ID NO 58
<211> LENGTH: 27
<212> TYPE: DNA
<213> ORGANISM: Artificial sequence
<220> FEATURE:
<223> OTHER INFORMATION: Synthetic GAL-BamH-R

<400> SEQUENCE: 58
ggatcctgaa ttttcaaaaa ttcttac                                         27

<210> SEQ ID NO 59
<211> LENGTH: 38
<212> TYPE: DNA
<213> ORGANISM: Artificial sequence
<220> FEATURE:
<223> OTHER INFORMATION: Synthetic KR-IL32Alpha-F

<400> SEQUENCE: 59
ctcgccttag ataaaagaat gtgcttcccg aaggtcct                             38

<210> SEQ ID NO 60
<211> LENGTH: 38
<212> TYPE: DNA
<213> ORGANISM: Artificial sequence
<220> FEATURE:
<223> OTHER INFORMATION: Synthetic IL32-INV-R

<400> SEQUENCE: 60
ctcgccttag ataaaagaat gtgcttcccg aaggtcct                             38
```

<210> SEQ ID NO 61
<211> LENGTH: 187
<212> TYPE: PRT
<213> ORGANISM: Artificial sequence
<220> FEATURE:
<223> OTHER INFORMATION: Saccharomyces cerevisiae TFP-11-AA

<400> SEQUENCE: 61

```
Met Lys Leu Ser Thr Val Leu Leu Ser Ala Gly Leu Ala Ser Thr Thr
1               5                   10                  15

Leu Ala Gln Phe Ser Asn Ser Thr Ser Ala Ser Ser Thr Asp Val Thr
            20                  25                  30

Ser Ser Ser Ile Ser Thr Ser Gly Ser Val Thr Ile Thr Ser
        35                  40                  45

Ser Glu Ala Pro Glu Ser Asp Asn Gly Thr Ser Thr Ala Ala Pro Thr
    50                  55                  60

Glu Thr Ser Thr Glu Ala Pro Thr Thr Ala Ile Pro Thr Asn Gly Thr
65                  70                  75                  80

Ser Thr Glu Ala Pro Thr Thr Ala Ile Pro Thr Asn Gly Thr Ser Thr
                85                  90                  95

Glu Ala Pro Thr Asp Thr Thr Glu Ala Pro Thr Thr Ala Leu Pro
            100                 105                 110

Thr Asn Gly Thr Ser Thr Glu Ala Pro Thr Asp Thr Thr Thr Glu Ala
            115                 120                 125

Pro Thr Thr Gly Leu Pro Thr Asn Gly Thr Thr Ser Ala Phe Pro Pro
130                 135                 140

Thr Thr Ser Leu Pro Pro Ser Asn Thr Thr Thr Thr Pro Pro Tyr Asn
145                 150                 155                 160

Pro Ser Thr Asp Tyr Thr Thr Asp Tyr Thr Val Val Thr Glu Tyr Thr
                165                 170                 175

Thr Tyr Cys Pro Glu Pro Leu Ala Ala Ser Ala
            180                 185
```

<210> SEQ ID NO 62
<211> LENGTH: 621
<212> TYPE: DNA
<213> ORGANISM: Artificial sequence
<220> FEATURE:
<223> OTHER INFORMATION: Saccharomyces cerevisiae TFP-11-NT

<400> SEQUENCE: 62

```
ggccattacg gccggggagc tacaaagaca agcaaaataa aatacgttcg ctctattaag    60
atgaaattat caactgtcct attatctgcc ggtttagcct cgactacttt ggcccaattt   120
tccaacagta catctgcttc ttccaccgat gtcacttcct cctcttccat ctccacttcc   180
tctggctcag taactatcac atcttctgaa gctccagaat ccgacaacgg taccagcaca   240
gctgcaccaa ctgaaacctc aacagaggct ccaaccactg ctatcccaac taacggtacc   300
tctactgaag ctccaaccac tgctatccca actaacggta cctctactga agctccaact   360
gatactacta ctgaagctcc aaccaccgct cttccaacta acggtacttc tactgaagct   420
ccaactgata ctactactga agctccaacc accggtcttc caaccaacgg taccacttca   480
gctttcccac caactacatc tttgccacca agcaacacta ccaccactcc tccttacaac   540
ccatctactg actacaccac tgactacact gtagtcactg aatatactac ttactgtccg   600
gaaccactgg ccgcctcggc c                                             621
```

```
<210> SEQ ID NO 63
<211> LENGTH: 165
<212> TYPE: PRT
<213> ORGANISM: Artificial sequence
<220> FEATURE:
<223> OTHER INFORMATION: Saccharomyces cerevisiae TFP-22-AA

<400> SEQUENCE: 63

Met Gln Tyr Lys Lys Thr Leu Val Ala Ser Ala Leu Ala Ala Thr Thr
1               5                   10                  15

Leu Ala Ala Tyr Ala Pro Ser Glu Pro Trp Ser Thr Leu Thr Pro Thr
            20                  25                  30

Ala Thr Tyr Ser Gly Gly Val Thr Asp Tyr Ala Ser Thr Phe Gly Ile
        35                  40                  45

Ala Val Gln Pro Ile Ser Thr Thr Ser Ser Ala Ser Ser Ala Ala Thr
    50                  55                  60

Thr Ala Ser Ser Lys Ala Lys Arg Ala Ala Ser Gln Ile Gly Asp Gly
65                  70                  75                  80

Gln Val Gln Ala Ala Thr Thr Thr Ala Ser Val Ser Thr Lys Ser Thr
                85                  90                  95

Ala Ala Ala Val Ser Gln Ile Gly Asp Gly Gln Ile Gln Ala Thr Thr
            100                 105                 110

Lys Thr Thr Ala Ala Ala Val Ser Gln Ile Gly Asp Gly Gln Ile Gln
        115                 120                 125

Ala Thr Thr Lys Thr Thr Ser Ala Lys Thr Thr Ala Ala Ala Val Ser
    130                 135                 140

Gln Ile Ser Asp Gly Gln Ile Gln Ala Thr Thr Thr Thr Leu Ala Pro
145                 150                 155                 160

Leu Ala Ala Ser Ala
                165

<210> SEQ ID NO 64
<211> LENGTH: 564
<212> TYPE: DNA
<213> ORGANISM: Artificial sequence
<220> FEATURE:
<223> OTHER INFORMATION: Saccharomyces cerevisiae TFP-22-NT

<400> SEQUENCE: 64
ggccattacg gccgggggaa taagaaactc atattccttt tctaacccta gtacaataat      60
aataatataa tgcaatacaa aaagactttg gttgcctctg ctttggccgc tactacattg     120
gccgcctatg ctccatctga gccttggtcc actttgactc aacagccac ttacagcggt      180 ggtgttaccg actacgcttc caccttcggt attgccgttc aaccaatctc cactacatcc     240
agcgcatcat ctgcagccac cacagcctca tctaaggcca agagagctgc ttcccaaatt     300
ggtgatggtc aagtccaagc tgctaccact actgcttctg tctctaccaa gagtaccgct     360
gccgccgttt ctcagatcgg tgatggtcaa atccaagcta ctaccaagac taccgctgct     420
gctgtctctc aaattggtga tggtcaaatt caagctacca ccaagactac ctctgctaag     480
actaccgccg ctgccgtttc tcaaatcagt gatggtcaaa tccaagctac caccactact     540 ttagccccctc tggccgcctc ggcc                                           564

<210> SEQ ID NO 65
<211> LENGTH: 48
<212> TYPE: PRT
<213> ORGANISM: Artificial sequence
<220> FEATURE:
<223> OTHER INFORMATION: Saccharomyces cerevisiae TFP-29-AA
```

<400> SEQUENCE: 65

Met Lys Leu Glu Asn Thr Leu Phe Thr Leu Gly Ala Leu Gly Ser Ile
1               5                   10                  15

Ser Ala Ala Leu Val Ile Pro Asn Leu Glu Asn Ala Ala Asp His His
            20                  25                  30

Glu Leu Ile Asn Lys Glu Asp His His Glu Arg Leu Ala Ala Ser Ala
        35                  40                  45

<210> SEQ ID NO 66
<211> LENGTH: 216
<212> TYPE: DNA
<213> ORGANISM: Artificial sequence
<220> FEATURE:
<223> OTHER INFORMATION: Saccharomyces cerevisiae TFP-29-NT

<400> SEQUENCE: 66
ggccattacg gccggggaat tagcttcatc gccaataaaa aaacaaacta aacctaattc    60
taacaagcaa agatgaagtt agaaaatact ctatttacac tcggtgccct agggagcatc   120
tctgctgctt tggtcatccc aaatcttgaa aatgccgccg accaccacga actgattaac   180
aaggaagatc accacgagag actggccgcc tcggcc                             216

<210> SEQ ID NO 67
<211> LENGTH: 208
<212> TYPE: PRT
<213> ORGANISM: Artificial sequence
<220> FEATURE:
<223> OTHER INFORMATION: Saccharomyces cerevisiae TFP-34-AA

<400> SEQUENCE: 67

Met Arg Ala Thr Thr Leu Leu Ser Ser Val Val Ser Leu Ala Leu Leu
1               5                   10                  15

Ser Lys Glu Val Leu Ala Thr Pro Pro Ala Cys Leu Leu Ala Cys Val
            20                  25                  30

Ala Gln Val Gly Lys Ser Ser Ser Thr Cys Asp Ser Leu Asn Gln Val
        35                  40                  45

Thr Cys Tyr Cys Glu His Glu Asn Ser Ala Val Lys Lys Cys Leu Asp
    50                  55                  60

Ser Ile Cys Pro Asn Asn Asp Ala Asp Ala Ala Tyr Ser Ala Phe Lys
65                  70                  75                  80

Ser Ser Cys Ser Glu Gln Asn Ala Ser Leu Gly Asp Ser Ser Ser Ser
                85                  90                  95

Ala Ser Ser Ser Ala Ser Ser Ser Lys Ala Ser Ser Ser Thr Lys
            100                 105                 110

Ala Ser Ser Ser Ala Ser Ser Ser Thr Lys Ala Ser Ser Ser Ser
        115                 120                 125

Ala Ser Ser Pro Thr Lys Ala Ser Ser Ser Ala Ala Pro Ser Ser
    130                 135                 140

Ser Lys Ala Ser Ser Thr Glu Ser Ser Ser Ser Ser Ser Ser Thr
145                 150                 155                 160

Lys Ala Pro Ser Ser Glu Glu Ser Ser Thr Tyr Val Ser Ser Ser
                165                 170                 175

Lys Gln Ala Ser Ser Thr Ser Glu Ala His Ser Ser Ser Ala Ala Ser
            180                 185                 190

Ser Thr Val Ser Gln Glu Thr Val Ser Ser Ala Leu Ala Ala Ser Ala
        195                 200                 205

<210> SEQ ID NO 68
<211> LENGTH: 694
<212> TYPE: DNA
<213> ORGANISM: Artificial sequence
<220> FEATURE:
<223> OTHER INFORMATION: Saccharomyces cerevisiae TFP-34-NT

<400> SEQUENCE: 68

```
ggccattacg gccgggaggg tcaaagctca cagcactact acactcgttc aacactcgtt      60
atatattatc atgcgcgcca ccactttatt atcttcagtc gtttctttgg cattgttgtc     120
gaaggaagtc ttagcaacac ctccagcttg tttattggcc tgtgttgcgc aagtcggcaa     180
atcctcttcc acatgtgact ctttgaatca agtcacctgt tactgtgaac acgaaaactc     240
cgccgtcaag aaatgtctag actccatctg cccaaacaat gacgctgatg ctgcttattc     300
tgctttcaag agttcttgtt ccgaacaaaa tgcttcattg ggcgattcca gcagcagtgc     360
ctcctcatcc gcttcttcat ccagcaaggc ctcttcttct accaaggctt cttccagtag     420
cgcttcctcc tctaccaagg cttcttccag tagcgcttcc tccctacta aagcttcttc      480 cagcagcgct gccccatctt ctagcaaggc ttcttccacc gaatcctctt cttcctcttc     540
ttcttccacc aaggctcctt ccagtgaaga atcctcttcc acttatgtct cttcgagcaa     600
gcaagcttcc tccactagcg aggctcactc ttccagtgct gcctcttcga ccgtgtccca     660
agaaacagtc tcctctgctc tggccgcctc ggcc                                 694
```

<210> SEQ ID NO 69
<211> LENGTH: 38
<212> TYPE: PRT
<213> ORGANISM: Artificial sequence
<220> FEATURE:
<223> OTHER INFORMATION: Saccharomyces cerevisiae TFP-38-AA

<400> SEQUENCE: 69

Met Lys Leu Ser Gln Val Val Ser Ala Val Ala Phe Thr Gly Leu
1               5                   10                  15

Val Ser Ala Ala Asn Ser Ser Asn Ser Ser Ser Ser Lys Asn Ala Ala
            20                  25                  30

Gln Leu Ala Ala Ser Ala
        35

<210> SEQ ID NO 70
<211> LENGTH: 184
<212> TYPE: DNA
<213> ORGANISM: Artificial sequence
<220> FEATURE:
<223> OTHER INFORMATION: Saccharomyces cerevisiae TFP-38-NT

<400> SEQUENCE: 70

```
ggccattacg gccgggggac tatcaaatca tacagatatt gtcaaaaaaa aaaaagacta      60
ataataaaaa atgaagttat ctcaagttgt tgtttccgcc gtcgccttca ctggtttagt     120
aagtgctgct aacagttcta acagctcaag ctcaaagaat gctgcccaac tggccgcctc     180
ggcc                                                                   184
```

<210> SEQ ID NO 71
<211> LENGTH: 26
<212> TYPE: DNA
<213> ORGANISM: Artificial sequence
<220> FEATURE:
<223> OTHER INFORMATION: Synthetic BamH-CIS-F

<400> SEQUENCE: 71
ccggatccat gcaattcaaa aacgtc                                              26

<210> SEQ ID NO 72
<211> LENGTH: 37
<212> TYPE: DNA
<213> ORGANISM: Artificial sequence
<220> FEATURE:
<223> OTHER INFORMATION: Synthetic BamH-SED-F

<400> SEQUENCE: 72
ccggatccat gaaattatca actgtcctat tatctgc                                  37

<210> SEQ ID NO 73
<211> LENGTH: 35
<212> TYPE: DNA
<213> ORGANISM: Artificial sequence
<220> FEATURE:
<223> OTHER INFORMATION: Synthetic BamH-SIM-F

<400> SEQUENCE: 73
ccggatccat gaaattctca actgccgtta ctacg                                    35

<210> SEQ ID NO 74
<211> LENGTH: 34
<212> TYPE: DNA
<213> ORGANISM: Artificial sequence
<220> FEATURE:
<223> OTHER INFORMATION: Synthetic BamH-YOR247W-F

<400> SEQUENCE: 74
ccggatccat gcttcaatcc gttgtctttt tcgc                                     34

<210> SEQ ID NO 75
<211> LENGTH: 30
<212> TYPE: DNA
<213> ORGANISM: Artificial sequence
<220> FEATURE:
<223> OTHER INFORMATION: Synthetic BamH-HSP-F

<400> SEQUENCE: 75
ccggatccat gcaatacaaa aagactttgg                                          30

<210> SEQ ID NO 76
<211> LENGTH: 36
<212> TYPE: DNA
<213> ORGANISM: Artificial sequence
<220> FEATURE:
<223> OTHER INFORMATION: Synthetic BamH-OST-F

<400> SEQUENCE: 76
ccggatccat gaattggctg tttttggtct cgctgg                                   36

<210> SEQ ID NO 77
<211> LENGTH: 41
<212> TYPE: DNA
<213> ORGANISM: Artificial sequence
<220> FEATURE:
<223> OTHER INFORMATION: Synthetic IL32-TGA-R

<400> SEQUENCE: 77
cactccgttc aagtcgactc attttgagga ttggggttca g                             41

<210> SEQ ID NO 78
<211> LENGTH: 30

```
<212> TYPE: DNA
<213> ORGANISM: Artificial sequence
<220> FEATURE:
<223> OTHER INFORMATION: Synthetic H77-1-R

<400> SEQUENCE: 78
aagtcgacat ttaaatcttt tatctaaggc                               30

<210> SEQ ID NO 79
<211> LENGTH: 20
<212> TYPE: DNA
<213> ORGANISM: Artificial sequence
<220> FEATURE:
<223> OTHER INFORMATION: Synthetic hGH-F

<400> SEQUENCE: 79
ttcccaacca ttcccttatc                                          20

<210> SEQ ID NO 80
<211> LENGTH: 19
<212> TYPE: DNA
<213> ORGANISM: Artificial sequence
<220> FEATURE:
<223> OTHER INFORMATION: Synthetic hGH-R

<400> SEQUENCE: 80
ctagaagcca cagctgccc                                           19

<210> SEQ ID NO 81
<211> LENGTH: 38
<212> TYPE: DNA
<213> ORGANISM: Artificial sequence
<220> FEATURE:
<223> OTHER INFORMATION: Synthetic KR-hGH-F

<400> SEQUENCE: 81
ctcgccttag ataaaagatt cccaaccatt cccttatc                      38

<210> SEQ ID NO 82
<211> LENGTH: 37
<212> TYPE: DNA
<213> ORGANISM: Artificial sequence
<220> FEATURE:
<223> OTHER INFORMATION: Synthetic hGH-Sal-R

<400> SEQUENCE: 82
cactccgttc aagtcgacct agaagccaca gctgccc                       37

<210> SEQ ID NO 83
<211> LENGTH: 70
<212> TYPE: DNA
<213> ORGANISM: Artificial sequence
<220> FEATURE:
<223> OTHER INFORMATION: Synthetic GT70-R

<400> SEQUENCE: 83
tcagatttac agataatgat gtcattatta aatatatata tatatatatt gtcactccgt   60
tcaagtcgac                                                         70

<210> SEQ ID NO 84
<211> LENGTH: 101
<212> TYPE: PRT
<213> ORGANISM: Artificial sequence
<220> FEATURE:
<223> OTHER INFORMATION: Pichia pastoris PpTFP1-aa
```

<400> SEQUENCE: 84

Met Gln Phe Asn Ser Val Val Ile Ser Gln Leu Leu Thr Leu Ala
1               5                   10                  15

Ser Val Ser Met Gly Ala Ser Thr Ala Phe Lys Glu His His Gln His
            20                  25                  30

Gln Arg Ala Thr Leu Glu Lys Arg Ala Thr Thr Cys Lys Phe Pro Thr
        35                  40                  45

Asp Lys Asn Leu Val Ala Val Thr Pro Asn Ser Lys Asn Gly Gly Trp
50                  55                  60

Ala Leu Ser Pro Asp Gln Glu Cys Thr Ala Gly Ser Tyr Cys Pro Tyr
65                  70                  75                  80

Ala Cys Pro Pro Gly Gln Leu Met Ala Gln Trp Asp Pro Ser Ala Thr
                85                  90                  95

Leu Ala Ala Ser Ala
            100

<210> SEQ ID NO 85
<211> LENGTH: 419
<212> TYPE: DNA
<213> ORGANISM: Artificial sequence
<220> FEATURE:
<223> OTHER INFORMATION: Pichia pastoris PpTFP1-nt

<400> SEQUENCE: 85
ggccattacg ccggggcaca gtaactttga cataatatct ggtagctgca tcacttcacc     60
gactattcat tccttccttt ttagtattac caactatatc acattccttt aagaaaatgc    120
aattcaacag tgtcgtcatc agccaacttt tgctgactct agccagtgtc tcaatgggag    180
cttcaaccgc tttcaaggag caccaccagc accaaagagc tactctagag aagagagcta    240
ctacctgcaa attccccact gacaaaaact tggtcgctgt tacaccaaac tccaaaaatg    300
gaggctgggc tctgagtcca gaccaggagt gcacagcagg ttcttattgt ccttatgctt    360
gtccaccagg ccagttgatg gctcaatggg acccatcggc cacactggcc gcctcggcc    419

<210> SEQ ID NO 86
<211> LENGTH: 94
<212> TYPE: PRT
<213> ORGANISM: Artificial sequence
<220> FEATURE:
<223> OTHER INFORMATION: Pichia pastoris PpTFP2-aa

<400> SEQUENCE: 86

Met Gln Phe Ser Ile Val Ala Thr Leu Ala Leu Ala Gly Ser Ala Leu
1               5                   10                  15

Ala Ala Tyr Ser Asn Val Thr Tyr Thr Tyr Glu Thr Thr Ile Thr Asp
            20                  25                  30

Val Val Thr Glu Leu Thr Thr Tyr Cys Pro Glu Pro Thr Thr Phe Val
        35                  40                  45

His Lys Asn Lys Thr Ile Thr Val Thr Ala Pro Thr Thr Leu Thr Ile
    50                  55                  60

Thr Asp Cys Pro Cys Thr Ile Ser Lys Thr Thr Lys Ile Thr Asp
65                  70                  75                  80

Val Pro Pro Thr Thr His Ser Thr Pro Leu Ala Ala Ser Ala
                85                  90

<210> SEQ ID NO 87
<211> LENGTH: 345
<212> TYPE: DNA

<210> SEQ ID NO 87
<211> LENGTH: 345
<212> TYPE: DNA
<213> ORGANISM: Artificial sequence
<220> FEATURE:
<223> OTHER INFORMATION: Pichia pastoris PpTFP2-nt

<400> SEQUENCE: 87

```
ggccattacg gccggggagc ttacatttta ccgttccgtc actcgcttca ctcaacaaca    60
aaaatgcaat tctctatcgt cgctactttg gctcttgctg gttccgctct ggctgcttac   120
tctaacgtaa cttacactta cgagactacc atcaccgatg ttgtcaccga gctcaccact   180
tactgcccag agccaaccac cttcgttcac aagaacaaga ccatcactgt gaccgcccca   240
accactttga ccatcactga ctgtccttgc accatctcca agaccaccaa gatcaccact   300
gatgttccac caaccaccca ctccacccca ctggccgcct cggcc                   345
```

<210> SEQ ID NO 88
<211> LENGTH: 82
<212> TYPE: PRT
<213> ORGANISM: Artificial sequence
<220> FEATURE:
<223> OTHER INFORMATION: Pichia pastoris PpTFP3-aa

<400> SEQUENCE: 88

```
Met Lys Phe Ser Thr Ala Phe Ala Gly Phe Val Ala Leu Asn Ala Val
1               5                   10                  15
Ser Ile Val Ala Gln Asp Glu Ala Thr Asp Ala His Val Val Thr Thr
            20                  25                  30
Thr Val Thr Thr Ala Ser Thr Glu Thr His Arg Trp Gly Arg Phe Asp
        35                  40                  45
Lys Thr Ser Pro Pro Thr Thr Ser Thr Ser Ser Gly Thr His Arg Trp
    50                  55                  60
Gly Arg Phe Asn Lys Thr Pro Asp Pro Thr Thr Thr Thr Ser Ala Ala
65                  70                  75                  80
Ser Ala
```

<210> SEQ ID NO 89
<211> LENGTH: 273
<212> TYPE: DNA
<213> ORGANISM: Artificial sequence
<220> FEATURE:
<223> OTHER INFORMATION: Pichia pastoris PpTFP3-nt

<400> SEQUENCE: 89

```
ggccattacg gccggggaac atcaagaatg aagttttcca ctgcgtttgc tggctttgtt    60
gccctaaatg ctgtgtccat tgttgctcag gacgaggcta ccgatgctca cgttgtcacc   120
acaactgtga ccaccgcttc cactgagact cacagatggg gaagattcga caagacttct   180
cctcctacaa cttccacttc ttcaggtact cacagatggg gaagatttaa caaaactcca   240
gatcctacca ctaccacctc ggccgcctcg gcc                                273
```

<210> SEQ ID NO 90
<211> LENGTH: 127
<212> TYPE: PRT
<213> ORGANISM: Artificial sequence
<220> FEATURE:
<223> OTHER INFORMATION: Pichia pastoris PpTFP4-aa

<400> SEQUENCE: 90

```
Met Gln Tyr Arg Ser Leu Phe Leu Gly Ser Ala Leu Leu Ala Ala Ala
1               5                   10                  15
Asn Ala Ala Val Tyr Asn Thr Thr Val Thr Asp Val Val Ser Glu Leu
```

```
                    20                  25                  30
Glu Thr Thr Val Leu Thr Ile Thr Ser Cys Ala Glu Asp Lys Cys Ile
                35                  40                  45
Thr Ser Lys Ser Thr Gly Leu Ile Thr Thr Ser Thr Leu Thr Lys His
            50                  55                  60
Gly Val Val Thr Val Val Thr Val Cys Asp Leu Pro Ser Thr Thr
65                  70                  75                  80
Lys Ser Tyr Val Pro Pro Ala Lys Thr Thr Ile Pro Pro Glu
                85                  90                  95
Lys Thr Thr Thr Thr Val Pro Pro Ala Lys Thr Thr Thr Thr Val
                100                 105                 110
Pro Pro Pro Ala Lys Thr Thr Ser Thr Ala Leu Ala Ala Ser Ala
                115                 120                 125
```

<210> SEQ ID NO 91
<211> LENGTH: 444
<212> TYPE: DNA
<213> ORGANISM: Artificial sequence
<220> FEATURE:
<223> OTHER INFORMATION: Pichia pastoris PpTFP4-nt

<400> SEQUENCE: 91

```
ggccattacg gggggaactc actgtttcag tttattccaa ctactttcac tcacttatca      60
aaaatgcaat acagatctct cttttaggt tccgccttat tggccgctgc taacgctgct     120
gtttacaaca ccaccgtcac tgacgttgtt tccgagttgg agaccaccgt tctgactatc     180
acctcttgtg ctgaggacaa gtgtatcacc agtaagtcca ccggattgat cactacctcc     240
accctcacca agcacggtgt tgtcactgtt gtcaccactg tctgtgactt gccaagcacc     300
accaagagct acgtcccacc tgctaagact actactattc ctcctccaga gaagactacc     360
accactgtcc cacctccagc caagactacc accactgtcc cacctccagc caagactact     420
agtaccgccc tggccgcctc ggcc                                            444
```

<210> SEQ ID NO 92
<211> LENGTH: 38
<212> TYPE: DNA
<213> ORGANISM: Artificial sequence
<220> FEATURE:
<223> OTHER INFORMATION: Synthetic YGR279C-F

<400> SEQUENCE: 92

```
ggccattacg gccaaaatgc gtctctctaa cctaattg                              38
```

<210> SEQ ID NO 93
<211> LENGTH: 21
<212> TYPE: DNA
<213> ORGANISM: Artificial sequence
<220> FEATURE:
<223> OTHER INFORMATION: Synthetic YGR279C-R

<400> SEQUENCE: 93

```
tcattggata gaataccccca g                                               21
```

<210> SEQ ID NO 94
<211> LENGTH: 38
<212> TYPE: DNA
<213> ORGANISM: Artificial sequence
<220> FEATURE:
<223> OTHER INFORMATION: Synthetic YLR037C-F

<400> SEQUENCE: 94

```
ggccattacg gccaaaatgg tcaaactaac ttcaattg                              38
```

<210> SEQ ID NO 95
<211> LENGTH: 22
<212> TYPE: DNA
<213> ORGANISM: Artificial sequence
<220> FEATURE:
<223> OTHER INFORMATION: Synthetic YLR037C-R

<400> SEQUENCE: 95

```
ttagtttgga acagcagtgt ag                                              22
```

<210> SEQ ID NO 96
<211> LENGTH: 36
<212> TYPE: DNA
<213> ORGANISM: Artificial sequence
<220> FEATURE:
<223> OTHER INFORMATION: Synthetic YLR110C-F

<400> SEQUENCE: 96

```
ggccattacg gccaaaatgc aattttctac tgtcgc                               36
```

<210> SEQ ID NO 97
<211> LENGTH: 20
<212> TYPE: DNA
<213> ORGANISM: Artificial sequence
<220> FEATURE:
<223> OTHER INFORMATION: Synthetic YLR110C-R

<400> SEQUENCE: 97

```
ttacaacaac aaagcagcgg                                                 20
```

<210> SEQ ID NO 98
<211> LENGTH: 37
<212> TYPE: DNA
<213> ORGANISM: Artificial sequence
<220> FEATURE:
<223> OTHER INFORMATION: Synthetic YOR383C-F

<400> SEQUENCE: 98

```
ggccattacg gccaaaatga aattctcttc cgctttg                              37
```

<210> SEQ ID NO 99
<211> LENGTH: 21
<212> TYPE: DNA
<213> ORGANISM: Artificial sequence
<220> FEATURE:
<223> OTHER INFORMATION: Synthetic YOR383C-R

<400> SEQUENCE: 99

```
ttacaataac atgacggcag c                                               21
```

<210> SEQ ID NO 100
<211> LENGTH: 36
<212> TYPE: DNA
<213> ORGANISM: Artificial sequence
<220> FEATURE:
<223> OTHER INFORMATION: Synthetic YIL011W-F

<400> SEQUENCE: 100

```
ggccattacg gccaaaatgt ctttcactaa aatcgc                               36
```

<210> SEQ ID NO 101
<211> LENGTH: 21
<212> TYPE: DNA

<213> ORGANISM: Artificial sequence
<220> FEATURE:
<223> OTHER INFORMATION: Synthetic YIL011W-R

<400> SEQUENCE: 101
tcataagagc atagcagcgg c                                               21

<210> SEQ ID NO 102
<211> LENGTH: 38
<212> TYPE: DNA
<213> ORGANISM: Artificial sequence
<220> FEATURE:
<223> OTHER INFORMATION: Synthetic YHR214W-F

<400> SEQUENCE: 102
ggccattacg gccaaaatgt tcaatcgttt taacaaat                             38

<210> SEQ ID NO 103
<211> LENGTH: 22
<212> TYPE: DNA
<213> ORGANISM: Artificial sequence
<220> FEATURE:
<223> OTHER INFORMATION: Synthetic YHR214W-R

<400> SEQUENCE: 103
ttacaaaccg gaaacagaac ca                                              22

<210> SEQ ID NO 104
<211> LENGTH: 39
<212> TYPE: DNA
<213> ORGANISM: Artificial sequence
<220> FEATURE:
<223> OTHER INFORMATION: Synthetic YNL160W-F

<400> SEQUENCE: 104
ggccattacg gccaaaatga agttccaagt tgttttatc                            39

<210> SEQ ID NO 105
<211> LENGTH: 21
<212> TYPE: DNA
<213> ORGANISM: Artificial sequence
<220> FEATURE:
<223> OTHER INFORMATION: Synthetic YNL160W-R

<400> SEQUENCE: 105
tcatgggaaa atgctttcca g                                               21

<210> SEQ ID NO 106
<211> LENGTH: 37
<212> TYPE: DNA
<213> ORGANISM: Artificial sequence
<220> FEATURE:
<223> OTHER INFORMATION: Synthetic YGR296C-A-F

<400> SEQUENCE: 106
ggccattacg gccaaaatgg aatctattat cctcagc                              37

<210> SEQ ID NO 107
<211> LENGTH: 21
<212> TYPE: DNA
<213> ORGANISM: Artificial sequence
<220> FEATURE:
<223> OTHER INFORMATION: Synthetic YGR296C-A-R

<400> SEQUENCE: 107
ttaccgtcta gcttccagga g                                               21

<210> SEQ ID NO 108
<211> LENGTH: 39
<212> TYPE: DNA
<213> ORGANISM: Artificial sequence
<220> FEATURE:
<223> OTHER INFORMATION: Synthetic YOL154W-F

<400> SEQUENCE: 108
ggccattacg gccaaaatga agttctcttc cggcaaatc       39

<210> SEQ ID NO 109
<211> LENGTH: 20
<212> TYPE: DNA
<213> ORGANISM: Artificial sequence
<220> FEATURE:
<223> OTHER INFORMATION: Synthetic YOL154W-R

<400> SEQUENCE: 109
agttacctag acagccacca       20

<210> SEQ ID NO 110
<211> LENGTH: 39
<212> TYPE: DNA
<213> ORGANISM: Artificial sequence
<220> FEATURE:
<223> OTHER INFORMATION: Synthetic YPL187W-F

<400> SEQUENCE: 110
ggccattacg gccaaaatga gatttccttc aatttttac       39

<210> SEQ ID NO 111
<211> LENGTH: 19
<212> TYPE: DNA
<213> ORGANISM: Artificial sequence
<220> FEATURE:
<223> OTHER INFORMATION: Synthetic YPL187W-R

<400> SEQUENCE: 111
ttagtacatt ggttggccg       19

<210> SEQ ID NO 112
<211> LENGTH: 34
<212> TYPE: DNA
<213> ORGANISM: Artificial sequence
<220> FEATURE:
<223> OTHER INFORMATION: Synthetic YHR214W-F

<400> SEQUENCE: 112
ggccattacg gccaaaatgt tcaatcgttt taac       34

<210> SEQ ID NO 113
<211> LENGTH: 20
<212> TYPE: DNA
<213> ORGANISM: Artificial sequence
<220> FEATURE:
<223> OTHER INFORMATION: Synthetic YHR214W-

<400> SEQUENCE: 113
cggaaacaga accaccgttg       20

<210> SEQ ID NO 114
<211> LENGTH: 34
<212> TYPE: DNA
<213> ORGANISM: Artificial sequence
<220> FEATURE:

<223> OTHER INFORMATION: Synthetic YKR013W-F

<400> SEQUENCE: 114
ggccattacg gccaaaatga aattttctaa agtc                                34

<210> SEQ ID NO 115
<211> LENGTH: 20
<212> TYPE: DNA
<213> ORGANISM: Artificial sequence
<220> FEATURE:
<223> OTHER INFORMATION: Synthetic YKR013W-R

<400> SEQUENCE: 115
ctcaccaatg acattaccag                                                20

<210> SEQ ID NO 116
<211> LENGTH: 34
<212> TYPE: DNA
<213> ORGANISM: Artificial sequence
<220> FEATURE:
<223> OTHER INFORMATION: Synthetic YHR139C-F

<400> SEQUENCE: 116
ggccattacg gccaaaatga aattcacatc agtg                                34

<210> SEQ ID NO 117
<211> LENGTH: 20
<212> TYPE: DNA
<213> ORGANISM: Artificial sequence
<220> FEATURE:
<223> OTHER INFORMATION: Synthetic YHR139C-R

<400> SEQUENCE: 117
gtaactcgct actacttgtg                                                20

<210> SEQ ID NO 118
<211> LENGTH: 34
<212> TYPE: DNA
<213> ORGANISM: Artificial sequence
<220> FEATURE:
<223> OTHER INFORMATION: Synthetic YIL169C-F

<400> SEQUENCE: 118
ggccattacg gccaaaatgt tcaatcgttt aaac                                34

<210> SEQ ID NO 119
<211> LENGTH: 20
<212> TYPE: DNA
<213> ORGANISM: Artificial sequence
<220> FEATURE:
<223> OTHER INFORMATION: Synthetic YIL169C-R

<400> SEQUENCE: 119
agttgcgctt gcactagatg                                                20

<210> SEQ ID NO 120
<211> LENGTH: 34
<212> TYPE: DNA
<213> ORGANISM: Artificial sequence
<220> FEATURE:
<223> OTHER INFORMATION: Synthetic YOL155C-F

<400> SEQUENCE: 120
ggccattacg gccaaaatgt tcaatcgctt taat                                34

```
<210> SEQ ID NO 121
<211> LENGTH: 20
<212> TYPE: DNA
<213> ORGANISM: Artificial sequence
<220> FEATURE:
<223> OTHER INFORMATION: Synthetic YOL155C-R

<400> SEQUENCE: 121
agaggcagtg gaagccgatg                                                 20

<210> SEQ ID NO 122
<211> LENGTH: 34
<212> TYPE: DNA
<213> ORGANISM: Artificial sequence
<220> FEATURE:
<223> OTHER INFORMATION: Synthetic YMR325W-F

<400> SEQUENCE: 122
ggccattacg gccaaaatgg tcaaattaac ttca                                 34

<210> SEQ ID NO 123
<211> LENGTH: 20
<212> TYPE: DNA
<213> ORGANISM: Artificial sequence
<220> FEATURE:
<223> OTHER INFORMATION: Synthetic YMR325W-R

<400> SEQUENCE: 123
atagcagtgt agataccgtc                                                 20

<210> SEQ ID NO 124
<211> LENGTH: 34
<212> TYPE: DNA
<213> ORGANISM: Artificial sequence
<220> FEATURE:
<223> OTHER INFORMATION: Synthetic YDR134W-F

<400> SEQUENCE: 124
ggccattacg gccaaaatgc aattctctac cgtc                                 34

<210> SEQ ID NO 125
<211> LENGTH: 20
<212> TYPE: DNA
<213> ORGANISM: Artificial sequence
<220> FEATURE:
<223> OTHER INFORMATION: Synthetic YDR134W-R

<400> SEQUENCE: 125
ttacaacaat aaagcggcag                                                 20

<210> SEQ ID NO 126
<211> LENGTH: 34
<212> TYPE: DNA
<213> ORGANISM: Artificial sequence
<220> FEATURE:
<223> OTHER INFORMATION: Synthetic YLR300W-F

<400> SEQUENCE: 126
ggccattacg gccaaaatgc tttcgcttaa aacg                                 34

<210> SEQ ID NO 127
<211> LENGTH: 20
<212> TYPE: DNA
<213> ORGANISM: Artificial sequence
<220> FEATURE:
<223> OTHER INFORMATION: Synthetic YLR300W-R
```

-continued

<400> SEQUENCE: 127
tgatgatggt cgatagtgac                                            20

<210> SEQ ID NO 128
<211> LENGTH: 30
<212> TYPE: DNA
<213> ORGANISM: Artificial sequence
<220> FEATURE:
<223> OTHER INFORMATION: Synthetic SfiA-F

<400> SEQUENCE: 128
ctgagtctca cggccattat ggccaaaatg                                 30

<210> SEQ ID NO 129
<211> LENGTH: 57
<212> TYPE: PRT
<213> ORGANISM: Artificial sequence
<220> FEATURE:
<223> OTHER INFORMATION: Saccharomyces cerevisiae TFP-39-AA

<400> SEQUENCE: 129

Met Arg Leu Ser Asn Leu Ile Ala Ser Ala Ser Leu Leu Ser Ala Ala
1               5                   10                  15

Thr Leu Ala Ala Pro Ala Asn His Glu His Lys Asp Lys Arg Ala Val
            20                  25                  30

Val Thr Thr Thr Val Gln Lys Gln Thr Thr Val Ile Val Asn Gly Ala
        35                  40                  45

Ala Ser Thr Pro Leu Ala Ala Ser Ala
    50                  55

<210> SEQ ID NO 130
<211> LENGTH: 214
<212> TYPE: DNA
<213> ORGANISM: Artificial sequence
<220> FEATURE:
<223> OTHER INFORMATION: Saccharomyces cerevisiae TFP-39-nt

<400> SEQUENCE: 130
ggccattacg gccaaaatgc gtctctctaa cctaattgct tctgcctctc ttttatctgc    60
tgctactctt gctgcccccg ctaaccacga acacaaggac aagcgtgctg tggtcactac   120
cactgttcaa aaacaaacca ctgtcattgt taatggtgcc gcttcaactc ccctggccgc   180
ctcggcctct gctggcctcg ccttagataa aaga                              214

<210> SEQ ID NO 131
<211> LENGTH: 128
<212> TYPE: PRT
<213> ORGANISM: Artificial sequence
<220> FEATURE:
<223> OTHER INFORMATION: Saccharomyces cerevisiae TFP-43-AA

<400> SEQUENCE: 131

Met Gln Phe Ser Thr Val Ala Ser Ile Ala Ala Val Ala Ala Val Ala
1               5                   10                  15

Ser Ala Ala Ala Asn Val Thr Thr Ala Thr Val Ser Gln Glu Ser Thr
            20                  25                  30

Thr Leu Val Thr Ile Thr Ser Cys Glu Asp His Val Cys Ser Glu Thr
        35                  40                  45

Val Ser Pro Ala Leu Val Ser Thr Ala Thr Val Thr Val Asp Asp Val
    50                  55                  60

Ile Thr Gln Tyr Thr Thr Trp Cys Pro Leu Thr Thr Glu Ala Pro Lys 65                  70                  75                  80
Asn Gly Thr Ser Thr Ala Ala Pro Val Thr Ser Thr Glu Ala Pro Lys
                        85                  90                  95

Asn Thr Thr Ser Ala Ala Pro Thr His Ser Val Thr Ser Tyr Thr Gly
            100                 105                 110

Ala Ala Ala Lys Ala Leu Pro Ala Ala Gly Ala Leu Leu Ala Ala Ser
        115                 120                 125

<210> SEQ ID NO 132
<211> LENGTH: 403
<212> TYPE: DNA
<213> ORGANISM: Artificial sequence
<220> FEATURE:
<223> OTHER INFORMATION: Saccharomyces cerevisiae TFP-43-nt

<400> SEQUENCE: 132
ggccattacg gccaaaatgc aattttctac tgtcgcttct atcgccgctg tcgccgctgt     60
cgcttctgcc gctgctaacg ttaccactgc tactgtcagc caagaatcta ccactttggt    120
caccatcact tcttgtgaag accacgtctg ttctgaaact gtctcccag ctttggtttc     180 caccgctacc gtcaccgtcg atgacgttat cactcaatac accacctggt gccattgac     240 cactgaagcc caaagaacg gtacttctac tgctgctcca gttacctcta ctgaagctcc     300
aaagaacacc acctctgctg ctccaactca ctctgtcacc tcttacactg gtgctgctgc    360
taaggctttg ccagctgctg gtgctttgct ggccgcctcg gcc                      403

<210> SEQ ID NO 133
<211> LENGTH: 71
<212> TYPE: PRT
<213> ORGANISM: Artificial sequence
<220> FEATURE:
<223> OTHER INFORMATION: Saccharomyces cerevisiae TFP-44-AA

<400> SEQUENCE: 133

Met Lys Phe Ser Ser Ala Leu Val Leu Ser Ala Val Ala Ala Thr Ala
1               5                   10                  15

Leu Ala Glu Ser Ile Thr Thr Thr Ile Thr Ala Thr Lys Asn Gly His
            20                  25                  30

Val Tyr Thr Lys Thr Val Thr Gln Asp Ala Thr Phe Val Trp Gly Gly
        35                  40                  45

Glu Asp Ser Tyr Ala Ser Ser Thr Ser Ala Ala Glu Ser Ala Ala
    50                  55                  60

Glu Thr Ser Ala Ala Ser Ala
65                  70

<210> SEQ ID NO 134
<211> LENGTH: 229
<212> TYPE: DNA
<213> ORGANISM: Artificial sequence
<220> FEATURE:
<223> OTHER INFORMATION: Saccharomyces cerevisiae TFP-44-nt

<400> SEQUENCE: 134
ggccattacg gccaaaatga aattctcttc cgctttggtt ctatctgctg ttgccgctac     60
tgctcttgct gagagtatca ccaccaccat cactgccacc aagaacggtc atgtctacac    120
taagactgtc acccaagatg ctactttttgt ttggggtggt gaagactctt acgccagcag    180
cacttctgcc gctgaatctt ctgccgccga aacttcggcc gcctcggcc                229

```
<210> SEQ ID NO 135
<211> LENGTH: 119
<212> TYPE: PRT
<213> ORGANISM: Artificial sequence
<220> FEATURE:
<223> OTHER INFORMATION: Saccharomyces cerevisiae TFP-48-AA

<400> SEQUENCE: 135

Met Arg Leu Ser Asn Leu Ile Ala Ser Ala Ser Leu Leu Ser Ala Ala
1               5                   10                  15

Thr Leu Ala Ala Pro Ala Asn His Glu His Lys Asp Lys Arg Ala Val
            20                  25                  30

Val Thr Thr Thr Val Gln Lys Gln Thr Thr Ile Ile Val Asn Gly Ala
        35                  40                  45

Ala Ser Thr Pro Val Ala Leu Glu Glu Asn Ala Val Val Asn Ser
    50                  55                  60

Ala Pro Ala Ala Ala Thr Ser Thr Thr Ser Ser Ala Ala Ser Val Ala
65                  70                  75                  80

Thr Ala Ala Ala Ser Ser Ser Glu Asn Asn Ser Gln Val Ser Ala Ala
                85                  90                  95

Ala Ser Pro Ala Ser Ser Ala Ala Thr Ser Thr Gln Ser Ser Ser
            100                 105                 110

Ser Ser Leu Ala Ala Ser Ala
        115

<210> SEQ ID NO 136
<211> LENGTH: 373
<212> TYPE: DNA
<213> ORGANISM: Artificial sequence
<220> FEATURE:
<223> OTHER INFORMATION: Saccharomyces cerevisiae TFP-48-nt

<400> SEQUENCE: 136
ggccattacg gccaaaatgc gtctctctaa cctaattgct tctgcctctc ttttatctgc    60
tgctactctt gctgctcccg ctaaccacga acacaaggac aagcgtgctg tggtcactac   120
cactgttcaa aaacaaacca ctatcattgt taatggtgcc gcttcaactc cagttgctgc   180
tttggaagaa aatgctgttg tcaactccgc tccagctgcc gctaccagta caacatcgtc   240
tgctgcttct gtagctaccg ctgctgcttc ctcttctgag aacaactcac aagtttctgc   300
tgccgcatct ccagcctcca gctctgctgc tacatctact caatcttcct cttcctccct   360
ggccgcctcg gcc                                                      373

<210> SEQ ID NO 137
<211> LENGTH: 129
<212> TYPE: PRT
<213> ORGANISM: Artificial sequence
<220> FEATURE:
<223> OTHER INFORMATION: Saccharomyces cerevisiae TFP-52-AA

<400> SEQUENCE: 137

Met Lys Phe Gln Val Val Leu Ser Ala Leu Leu Ala Cys Ser Ser Ala
1               5                   10                  15

Val Val Ala Ser Pro Ile Glu Asn Leu Phe Lys Tyr Arg Ala Val Lys
            20                  25                  30

Ala Ser His Ser Lys Asn Ile Asn Ser Thr Leu Pro Ala Trp Asn Gly
        35                  40                  45

Ser Asn Ser Ser Asn Val Thr Tyr Ala Asn Gly Thr Asn Ser Thr Thr
    50                  55                  60
```

```
Asn Thr Thr Thr Ala Glu Ser Ser Gln Leu Gln Ile Ile Val Thr Gly
 65                  70                  75                  80

Gly Gln Val Pro Ile Thr Asn Ser Ser Leu Thr His Thr Asn Tyr Thr
                 85                  90                  95

Arg Leu Phe Asn Ser Ser Ser Ala Leu Asn Ile Thr Glu Leu Tyr Asn
            100                 105                 110

Val Ala Arg Val Val Asn Glu Thr Ile Gln Asp Asn Leu Ala Ala Ser
        115                 120                 125

Ala
```

<210> SEQ ID NO 138
<211> LENGTH: 403
<212> TYPE: DNA
<213> ORGANISM: Artificial sequence
<220> FEATURE:
<223> OTHER INFORMATION: Saccharomyces cerevisiae TFP-52-nt

<400> SEQUENCE: 138

```
ggccattacg gccaaaatga agttccaagt tgttttatct gcccttttgg catgttcatc    60
tgccgtcgtc gcaagcccaa tcgaaaacct attcaaatac agggcagtta aggcatctca   120
cagtaagaat atcaactcca ctttgccggc ctggaatggg tctaactcta gcaatgttac   180
ctacgctaat ggaacaaaca gtactaccaa tactactact gccgaaagca gtcaattaca   240
aatcattgta acaggtggtc aagtaccaat caccaacagt tctttgaccc acacaaacta   300
caccagatta ttcaacagtt cttctgcttt gaacattacc gaattgtaca atgttgcccg   360
tgttgttaac gaaacgatcc aagataacct ggccgcctcg gcc                     403
```

<210> SEQ ID NO 139
<211> LENGTH: 124
<212> TYPE: PRT
<213> ORGANISM: Artificial sequence
<220> FEATURE:
<223> OTHER INFORMATION: Saccharomyces cerevisiae TFP-54-aa

<400> SEQUENCE: 139

```
Met Val Lys Leu Thr Ser Ile Val Ala Gly Val Ala Ala Ile Ala Ala
  1               5                  10                  15

Gly Val Ala Ala Ala Pro Ala Thr Thr Thr Leu Ser Pro Ser Asp Glu
                 20                  25                  30

Arg Val Asn Leu Val Glu Leu Gly Val Tyr Val Ser Asp Ile Arg Ala
            35                  40                  45

His Leu Ala Glu Tyr Tyr Met Phe Gln Ala Ala His Pro Thr Glu Thr
 50                  55                  60

Tyr Pro Val Glu Ile Ala Glu Ala Val Phe Asn Tyr Gly Asp Phe Thr
 65                  70                  75                  80

Thr Met Leu Thr Gly Ile Pro Ala Asp Gln Val Thr Arg Val Ile Thr
                 85                  90                  95

Gly Val Pro Trp Tyr Ser Thr Arg Leu Arg Pro Ala Ile Ser Ser Ala
            100                 105                 110

Leu Ser Lys Asp Gly Ile Tyr Thr Ala Ala Ser Ala
        115                 120
```

<210> SEQ ID NO 140
<211> LENGTH: 388
<212> TYPE: DNA
<213> ORGANISM: Artificial sequence
<220> FEATURE:
<223> OTHER INFORMATION: Saccharomyces cerevisiae TFP-54-nt

<400> SEQUENCE: 140

```
ggccattacg gccaaaatgg tcaaactaac ttcaattgtt gctggtgtcg ctgctattgc    60
tgctggtgtc gctgctgccc cagccaccac tactttatct ccctctgatg aaagagttaa   120
cctggtcgaa ttaggtgtct acgtctcaga tatcagagct catttggctg aatactatat   180
gttccaagct gctcatccaa ctgaaactta cccagttgaa attgctgaag ctgttttcaa   240
ctacggtgat tcaccacta tgttgactgg tattcccgct gatcaagtca ctagagtcat   300
cactggtgtc ccatggtact ccaccagatt gagaccagct atctccagcg ctctatccaa   360
ggacggtatc tacacggccg cctcggcc                                      388
```

<210> SEQ ID NO 141
<211> LENGTH: 35
<212> TYPE: DNA
<213> ORGANISM: Artificial sequence
<220> FEATURE:
<223> OTHER INFORMATION: Synthetic YAR066W-F

<400> SEQUENCE: 141

```
ggccattatg gccaaaatgt tcaatcgttt taaca                               35
```

<210> SEQ ID NO 142
<211> LENGTH: 20
<212> TYPE: DNA
<213> ORGANISM: Artificial sequence
<220> FEATURE:
<223> OTHER INFORMATION: Synthetic YAR066W-R

<400> SEQUENCE: 142

```
gaaccaccgt tgagaatagc                                                20
```

<210> SEQ ID NO 143
<211> LENGTH: 35
<212> TYPE: DNA
<213> ORGANISM: Artificial sequence
<220> FEATURE:
<223> OTHER INFORMATION: Synthetic YFR026C-F

<400> SEQUENCE: 143

```
ggccattatg gccaaaatga cgccctatgc agtag                               35
```

<210> SEQ ID NO 144
<211> LENGTH: 20
<212> TYPE: DNA
<213> ORGANISM: Artificial sequence
<220> FEATURE:
<223> OTHER INFORMATION: Synthetic YFR026C-R

<400> SEQUENCE: 144

```
tcactttcca gagctataag                                                20
```

<210> SEQ ID NO 145
<211> LENGTH: 35
<212> TYPE: DNA
<213> ORGANISM: Artificial sequence
<220> FEATURE:
<223> OTHER INFORMATION: Synthetic YJL158C-F

<400> SEQUENCE: 145

```
ggccattatg gccaaaatgc aattcaaaaa cgtcg                               35
```

<210> SEQ ID NO 146

```
<211> LENGTH: 21
<212> TYPE: DNA
<213> ORGANISM: Artificial sequence
<220> FEATURE:
<223> OTHER INFORMATION: Synthetic YJL158C-R

<400> SEQUENCE: 146
gtcgaccaaa gaaacagctt c                                               21

<210> SEQ ID NO 147
<211> LENGTH: 34
<212> TYPE: DNA
<213> ORGANISM: Artificial sequence
<220> FEATURE:
<223> OTHER INFORMATION: Synthetic YGR106C-F

<400> SEQUENCE: 147
ggccattatg gccaaaatgg tgttcggtca gctg                                 34

<210> SEQ ID NO 148
<211> LENGTH: 22
<212> TYPE: DNA
<213> ORGANISM: Artificial sequence
<220> FEATURE:
<223> OTHER INFORMATION: Synthetic YGR106C-R

<400> SEQUENCE: 148
ccaacgcacc atatgtgata tc                                              22

<210> SEQ ID NO 149
<211> LENGTH: 35
<212> TYPE: DNA
<213> ORGANISM: Artificial sequence
<220> FEATURE:
<223> OTHER INFORMATION: Synthetic YDR077W-F

<400> SEQUENCE: 149
ggccattatg gccaaaatga aattatcaac tgtcc                                35

<210> SEQ ID NO 150
<211> LENGTH: 19
<212> TYPE: DNA
<213> ORGANISM: Artificial sequence
<220> FEATURE:
<223> OTHER INFORMATION: Synthetic YDR077W-R

<400> SEQUENCE: 150
taacatagca acaccagcc                                                  19

<210> SEQ ID NO 151
<211> LENGTH: 35
<212> TYPE: DNA
<213> ORGANISM: Artificial sequence
<220> FEATURE:
<223> OTHER INFORMATION: Synthetic YIL123W-F

<400> SEQUENCE: 151
ggccattatg gccaaaatga aattctcaac tgccg                                35

<210> SEQ ID NO 152
<211> LENGTH: 20
<212> TYPE: DNA
<213> ORGANISM: Artificial sequence
<220> FEATURE:
<223> OTHER INFORMATION: Synthetic YIL123W-R

<400> SEQUENCE: 152
```

```
acagagacgg tacacccgtc                                                    20

<210> SEQ ID NO 153
<211> LENGTH: 36
<212> TYPE: DNA
<213> ORGANISM: Artificial sequence
<220> FEATURE:
<223> OTHER INFORMATION: Synthetic YNL190W-F

<400> SEQUENCE: 153
ggccattatg gccaaaatga agttctcttc tgttac                                  36

<210> SEQ ID NO 154
<211> LENGTH: 22
<212> TYPE: DNA
<213> ORGANISM: Artificial sequence
<220> FEATURE:
<223> OTHER INFORMATION: Synthetic YNL190W-R

<400> SEQUENCE: 154
gcaccggcta cggcagcact ac                                                 22

<210> SEQ ID NO 155
<211> LENGTH: 35
<212> TYPE: DNA
<213> ORGANISM: Artificial sequence
<220> FEATURE:
<223> OTHER INFORMATION: Synthetic YBR078W-F

<400> SEQUENCE: 155
ggccattatg gccaaaatgc aattcaagaa cgctt                                   35

<210> SEQ ID NO 156
<211> LENGTH: 21
<212> TYPE: DNA
<213> ORGANISM: Artificial sequence
<220> FEATURE:
<223> OTHER INFORMATION: Synthetic YBR078W-R

<400> SEQUENCE: 156
cagtgatgaa ccaaccgtct c                                                  21

<210> SEQ ID NO 157
<211> LENGTH: 36
<212> TYPE: DNA
<213> ORGANISM: Artificial sequence
<220> FEATURE:
<223> OTHER INFORMATION: Synthetic YJL178C-F

<400> SEQUENCE: 157
ggccattatg gccaaaatgg tatcgaagac ttggat                                  36

<210> SEQ ID NO 158
<211> LENGTH: 20
<212> TYPE: DNA
<213> ORGANISM: Artificial sequence
<220> FEATURE:
<223> OTHER INFORMATION: Synthetic YJL178C-R

<400> SEQUENCE: 158
aacggcgcta taaccgcctc                                                    20

<210> SEQ ID NO 159
<211> LENGTH: 36
<212> TYPE: DNA
```

```
<213> ORGANISM: Artificial sequence
<220> FEATURE:
<223> OTHER INFORMATION: Synthetic YMR307W-F

<400> SEQUENCE: 159
ggccattatg gccaaaatgt tgtttaaatc cctttc                                36

<210> SEQ ID NO 160
<211> LENGTH: 20
<212> TYPE: DNA
<213> ORGANISM: Artificial sequence
<220> FEATURE:
<223> OTHER INFORMATION: Synthetic YMR307W-R

<400> SEQUENCE: 160
gcaaaaccga caccagcggc                                                  20

<210> SEQ ID NO 161
<211> LENGTH: 35
<212> TYPE: DNA
<213> ORGANISM: Artificial sequence
<220> FEATURE:
<223> OTHER INFORMATION: Synthetic YOR247W-F

<400> SEQUENCE: 161
ggccattatg gccaaaatgc ttcaatccgt tgtct                                 35

<210> SEQ ID NO 162
<211> LENGTH: 20
<212> TYPE: DNA
<213> ORGANISM: Artificial sequence
<220> FEATURE:
<223> OTHER INFORMATION: Synthetic YOR247W-R

<400> SEQUENCE: 162
actggtcgaa ttagtaatcg                                                  20

<210> SEQ ID NO 163
<211> LENGTH: 37
<212> TYPE: DNA
<213> ORGANISM: Artificial sequence
<220> FEATURE:
<223> OTHER INFORMATION: Synthetic YJL159W-F

<400> SEQUENCE: 163
ggccattatg gccaaaatgc aatacaaaaa gactttg                               37

<210> SEQ ID NO 164
<211> LENGTH: 20
<212> TYPE: DNA
<213> ORGANISM: Artificial sequence
<220> FEATURE:
<223> OTHER INFORMATION: Synthetic YJL159W-R

<400> SEQUENCE: 164
aaatcgatag cttccaagtg                                                  20

<210> SEQ ID NO 165
<211> LENGTH: 35
<212> TYPE: DNA
<213> ORGANISM: Artificial sequence
<220> FEATURE:
<223> OTHER INFORMATION: Synthetic YOR085W-F

<400> SEQUENCE: 165
ggccattatg gccaaaatga attggctgtt tttgg                                 35
```

```
<210> SEQ ID NO 166
<211> LENGTH: 20
<212> TYPE: DNA
<213> ORGANISM: Artificial sequence
<220> FEATURE:
<223> OTHER INFORMATION: Synthetic YOR085W-R

<400> SEQUENCE: 166
tttgaatggt gccgataacc                                            20

<210> SEQ ID NO 167
<211> LENGTH: 36
<212> TYPE: DNA
<213> ORGANISM: Artificial sequence
<220> FEATURE:
<223> OTHER INFORMATION: Synthetic YKR042W-F

<400> SEQUENCE: 167
ggccattatg gccaaaatga aattatccgc tctatt                          36

<210> SEQ ID NO 168
<211> LENGTH: 20
<212> TYPE: DNA
<213> ORGANISM: Artificial sequence
<220> FEATURE:
<223> OTHER INFORMATION: Synthetic YKR042W-R

<400> SEQUENCE: 168
gacaaagtta gcagaaccag                                            20

<210> SEQ ID NO 169
<211> LENGTH: 35
<212> TYPE: DNA
<213> ORGANISM: Artificial sequence
<220> FEATURE:
<223> OTHER INFORMATION: Synthetic YEL060C-F

<400> SEQUENCE: 169
ggccattatg gccaaaatga agttagaaaa tactc                           35

<210> SEQ ID NO 170
<211> LENGTH: 20
<212> TYPE: DNA
<213> ORGANISM: Artificial sequence
<220> FEATURE:
<223> OTHER INFORMATION: Synthetic YEL060C-R

<400> SEQUENCE: 170
cttgggtgaa gtaaccgatg                                            20

<210> SEQ ID NO 171
<211> LENGTH: 37
<212> TYPE: DNA
<213> ORGANISM: Artificial sequence
<220> FEATURE:
<223> OTHER INFORMATION: Synthetic YLR390W-A-F

<400> SEQUENCE: 171
ggccattatg gccaaaatgc gtgccaccac tttatta                         37

<210> SEQ ID NO 172
<211> LENGTH: 20
<212> TYPE: DNA
<213> ORGANISM: Artificial sequence
<220> FEATURE:
```

<223> OTHER INFORMATION: Synthetic YLR390W-A-R

<400> SEQUENCE: 172
aacatagcgg caacagcagc                                                    20

<210> SEQ ID NO 173
<211> LENGTH: 35
<212> TYPE: DNA
<213> ORGANISM: Artificial sequence
<220> FEATURE:
<223> OTHER INFORMATION: Synthetic YMR251W-A-F

<400> SEQUENCE: 173
ggccattatg gccaaaatga agttatctca agttg                                   35

<210> SEQ ID NO 174
<211> LENGTH: 18
<212> TYPE: DNA
<213> ORGANISM: Artificial sequence
<220> FEATURE:
<223> OTHER INFORMATION: Synthetic YMR251W-A-R

<400> SEQUENCE: 174
aatcaaaaag gccaaagc                                                      18

<210> SEQ ID NO 175
<211> LENGTH: 99
<212> TYPE: PRT
<213> ORGANISM: Artificial sequence
<220> FEATURE:
<223> OTHER INFORMATION: Saccharomyces cerevisiae TFP-40-aa

<400> SEQUENCE: 175

Met Arg Leu Ser Asn Leu Ile Ala Ser Ala Ser Leu Leu Ser Ala Ala
1               5                   10                  15

Thr Leu Ala Ala Pro Ala Asn His Glu His Lys Asp Lys Arg Ala Val
            20                  25                  30

Val Thr Thr Thr Val Gln Lys Gln Thr Thr Ile Ile Val Asn Gly Ala
        35                  40                  45

Ala Ser Thr Pro Val Ala Ala Leu Glu Glu Asn Ala Val Val Asn Ser
    50                  55                  60

Ala Pro Ala Ala Ala Thr Ser Thr Thr Ser Ser Ala Ala Ser Val Ala
65                  70                  75                  80

Thr Ala Ala Ala Ser Ser Ser Glu Asn Asn Ser Gln Val Ser Val Ala
                85                  90                  95

Ala Ser Ala

<210> SEQ ID NO 176
<211> LENGTH: 313
<212> TYPE: DNA
<213> ORGANISM: Artificial sequence
<220> FEATURE:
<223> OTHER INFORMATION: Saccharomyces cerevisiae TFP-40-nt

<400> SEQUENCE: 176
ggccattacg gccaaaatgc gtctctctaa cctaattgct tctgcctctc ttttatctgc        60
tgctactctt gctgctcccg ctaaccacga acacaaggac aagcgtgctg tggtcactac       120
cactgttcaa aaacaaacca ctatcattgt taatggtgcc gcttcaactc cagttgctgc       180
tttggaagaa aatgctgttg tcaactccgc tccagctgcc gctaccagta caacatcgtc       240
tgctgcttct gtagctaccg ctgctgcttc ctcttctgag aacaactcac aagtttctgt       300

```
ggccgcctcg gcc                                                    313
```

<210> SEQ ID NO 177
<211> LENGTH: 85
<212> TYPE: PRT
<213> ORGANISM: Artificial sequence
<220> FEATURE:
<223> OTHER INFORMATION: Saccharomyces cerevisiae TFP-50-aa

<400> SEQUENCE: 177

```
Met Leu Gln Ser Val Val Phe Phe Ala Leu Leu Thr Phe Ala Ser Ser
1               5                   10                  15

Val Ser Ala Ile Tyr Ser Asn Asn Thr Val Ser Thr Thr Thr Thr Leu
            20                  25                  30

Ala Pro Ser Tyr Ser Leu Val Pro Gln Glu Thr Thr Ile Ser Tyr Ala
        35                  40                  45

Asp Asp Thr Thr Thr Phe Phe Val Thr Ser Val Tyr Ser Thr Ser
    50                  55                  60

Trp Phe Thr Ser Thr Ser Ala Thr Ile Thr Asn Ala Ala Ser Ser
65                  70                  75                  80

Leu Ala Ala Ser Ala
            85
```

<210> SEQ ID NO 178
<211> LENGTH: 271
<212> TYPE: DNA
<213> ORGANISM: Artificial sequence
<220> FEATURE:
<223> OTHER INFORMATION: Saccharomyces cerevisiae TFP-50-nt

<400> SEQUENCE: 178

```
ggccattacg gccaaaatgc ttcaatccgt tgtctttttc gctcttttaa ccttcgcaag     60
ttctgtgtca gcgatttatt caaacaatac tgtttctaca actaccactt tagcgcccag    120
ctactccttg gtgccccaag agactaccat atcgtacgcc gacgacacca ctacctttt    180 tgtcacctca acggtctact ccacgagctg gttcacctca acttcagcca ccattaccaa    240
tgcggcctcc tcctccctgg ccgcctcggc c                                    271
```

<210> SEQ ID NO 179
<211> LENGTH: 116
<212> TYPE: PRT
<213> ORGANISM: Artificial sequence
<220> FEATURE:
<223> OTHER INFORMATION: Saccharomyces cerevisiae TFP-51-aa

<400> SEQUENCE: 179

```
Met Leu Gln Ser Val Val Phe Phe Ala Leu Leu Thr Phe Ala Ser Ser
1               5                   10                  15

Val Ser Ala Ile Tyr Ser Asn Asn Thr Val Ser Thr Thr Thr Thr Leu
            20                  25                  30

Ala Pro Ser Tyr Ser Leu Val Pro Gln Glu Thr Thr Ile Ser Tyr Ala
        35                  40                  45

Asp Asp Thr Thr Thr Phe Phe Ala Thr Ser Val Tyr Ser Thr Ser
    50                  55                  60

Trp Phe Thr Ser Thr Ser Ala Thr Ile Thr Asn Ala Ala Ser Ser
65                  70                  75                  80

Leu Ser Thr Ser Ser Ala Ser Gly Ser Val Thr Pro Glu Ser Thr His
            85                  90                  95
```

```
Glu Ile Thr Ser Thr Ser Thr Ile Thr Ser Thr Ser Leu Leu Thr Leu
            100                 105                 110

Ala Ala Ser Ala
        115

<210> SEQ ID NO 180
<211> LENGTH: 364
<212> TYPE: DNA
<213> ORGANISM: Artificial sequence
<220> FEATURE:
<223> OTHER INFORMATION: Saccharomyces cerevisiae TFP-51-nt

<400> SEQUENCE: 180
ggccattacg gccaaaatgc ttcaatccgt tgtcttttc gctctttaa ccttcgcaag      60 ttctgtgtca gcgatttatt caaacaatac tgtttctaca actaccactt tagcgcccag    120
ctactccttg gtgccccaag agactaccat atcgtacgcc gacgacacca ctacctttt    180 tgccacctca acggtctact ccacgagctg gttcacctca acttcagcca ccattaccaa    240
tgcggcctcc tcctccttgt ccacctcttc ggcctctgga tctgtaaccc cagaatccac    300
ccatgaaatt acctccacct cgactatcac gtccacttcg ctgctaaccc tggccgcctc    360
ggcc                                                                  364

<210> SEQ ID NO 181
<211> LENGTH: 114
<212> TYPE: PRT
<213> ORGANISM: Artificial sequence
<220> FEATURE:
<223> OTHER INFORMATION: Saccharomyces cerevisiae TFP-57-aa

<400> SEQUENCE: 181

Met Phe Asn Arg Phe Asn Lys Leu Gln Ala Ala Leu Ala Leu Val Leu
1               5                   10                  15

Tyr Ser Gln Ser Ala Leu Gly Gln Tyr Tyr Thr Asn Ser Ser Ser Ile
            20                  25                  30

Ala Ser Asn Ser Ser Thr Ala Val Ser Ser Thr Ser Ser Gly Ser Val
        35                  40                  45

Ser Ile Ser Ser Ser Ile Glu Leu Thr Ser Ser Thr Ser Asp Val Ser
    50                  55                  60

Ser Leu Thr Glu Leu Thr Ser Ser Ser Thr Glu Val Ser Ser Ser
65                  70                  75                  80

Ile Ala Pro Ser Thr Ser Ser Glu Val Ser Ser Ile Thr Ser
                85                  90                  95

Ser Gly Ser Ser Val Ser Gly Ser Ser Ser Ile Thr Ser Leu Ala Ala
            100                 105                 110

Ser Ala

<210> SEQ ID NO 182
<211> LENGTH: 358
<212> TYPE: DNA
<213> ORGANISM: Artificial sequence
<220> FEATURE:
<223> OTHER INFORMATION: Saccharomyces cerevisiae TFP-57-nt

<400> SEQUENCE: 182
ggccattacg gccaaaatgt tcaatcgctt taataaactt caagccgctt tggctttggt     60
cctttactcc caaagtgcat tgggccaata ttataccaac agttcctcaa tcgctagtaa    120
cagctccacc gccgtttcgt caacttcatc aggttccgtt ccatcagta gttctattga    180
```

```
gttgacctca tctacttctg atgtctcgag ctctctcact gagttaacgt catcctccac    240
cgaagtctcg agctccattg ctccatcaac ctcgtcctct gaagtctcga gctctattac    300
ttcatcaggc tcttcagtct ccggctcatc ttctattact tccctggccg cctcggcc     358
```

```
<210> SEQ ID NO 183
<211> LENGTH: 199
<212> TYPE: PRT
<213> ORGANISM: Artificial sequence
<220> FEATURE:
<223> OTHER INFORMATION: Saccharomyces cerevisiae TFP-58-aa

<400> SEQUENCE: 183

Met Phe Asn Arg Phe Asn Lys Phe Gln Ala Ala Val Ala Leu Ala Leu
1               5                   10                  15

Leu Ser Arg Gly Ala Leu Gly Asp Ser Tyr Thr Asn Ser Thr Ser Ser
                20                  25                  30

Ala Asp Leu Ser Ser Ile Thr Ser Val Ser Ser Ala Ser Ala Ser Ala
            35                  40                  45

Thr Ala Ser Asp Ser Leu Ser Ser Ser Asp Gly Thr Val Tyr Leu Pro
        50                  55                  60

Ser Thr Thr Ile Ser Gly Asp Leu Thr Val Thr Gly Lys Val Ile Ala
65                  70                  75                  80

Thr Glu Ala Val Glu Val Ala Ala Gly Gly Lys Leu Thr Leu Leu Asp
                85                  90                  95

Gly Glu Lys Tyr Val Phe Ser Ser Asp Leu Lys Val His Gly Asp Leu
                100                 105                 110

Val Val Glu Lys Ser Glu Ala Ser Tyr Glu Gly Thr Ala Phe Asp Val
            115                 120                 125

Ser Gly Glu Thr Phe Glu Val Ser Gly Asn Phe Ser Ala Glu Glu Thr
        130                 135                 140

Gly Ala Val Ser Ala Ser Ile Tyr Ser Phe Thr Pro Ser Ser Phe Lys
145                 150                 155                 160

Ser Ser Gly Asp Ile Ser Leu Ser Leu Ser Lys Ala Lys Lys Gly Glu
                165                 170                 175

Val Thr Phe Ser Pro Tyr Ser Asn Ala Gly Thr Phe Ser Leu Ser Asn
                180                 185                 190

Ala Ile Leu Ala Ala Ser Ala
            195
```

```
<210> SEQ ID NO 184
<211> LENGTH: 613
<212> TYPE: DNA
<213> ORGANISM: Artificial sequence
<220> FEATURE:
<223> OTHER INFORMATION: Saccharomyces cerevisiae TFP-58-nt

<400> SEQUENCE: 184
ggccattacg gccaaaatgt tcaatcgttt taacaaattc caagctgctg tcgctttggc    60
cctactctct cgcggcgctc tcggtgactc ttacaccaat agcacctcct ccgcagactt    120
gagttctatc acttccgtct cgtcagctag tgcaagtgcc accgcttccg actcactttc    180
ttccagtgac ggtaccgttt atttgccatc cacaacaatt agcggtgatc tcacagttac    240
tggtaaagta attgcaaccg aggccgtgga agtcgctgcc ggtggtaagt tgactttact    300
tgacggtgaa aaatacgtct tctcatctga tctaaaagtt cacggtgatt tggttgtcga    360
aaagtctgaa gcaagctacg aaggtaccgc cttcgacgtt tctggtgaga cttttgaagt    420
```

```
ttccggtaac ttcagtgctg aagaaactgg cgctgtctcc gcatctatct attcattcac    480
acctagctcg ttcaagagca gcggtgacat ttctttgagt tgtcaaagg ccaagaaggg     540 tgaagtcacc tttctccat actctaacgc tggtaccttt tctttgtcaa atgctattct    600
ggccgcctcg gcc                                                        613
```

```
<210> SEQ ID NO 185
<211> LENGTH: 55
<212> TYPE: PRT
<213> ORGANISM: Artificial sequence
<220> FEATURE:
<223> OTHER INFORMATION: Saccharomyces cerevisiae TFP-59-aa

<400> SEQUENCE: 185

Met Asn Trp Leu Phe Leu Val Ser Leu Val Phe Phe Cys Gly Val Ser
1               5                   10                  15

Thr His Pro Ala Leu Ala Met Ser Ser Asn Arg Leu Leu Lys Leu Ala
            20                  25                  30

Asn Lys Ser Pro Lys Lys Ile Ile Pro Leu Lys Asp Ser Ser Phe Glu
        35                  40                  45

Asn Ile Leu Ala Ala Ser Ala
    50                  55

<210> SEQ ID NO 186
<211> LENGTH: 181
<212> TYPE: DNA
<213> ORGANISM: Artificial sequence
<220> FEATURE:
<223> OTHER INFORMATION: Saccharomyces cerevisiae TFP-59-nt

<400> SEQUENCE: 186
```

```
ggccattacg gccaaaatga attggctgtt tttggtctcg ctggttttct tctgcggcgt     60
gtcaacccat cctgccctgg caatgtccag caacagacta ctaaagctgg ctaataaatc    120
tcccaagaaa attatacctc tgaaggactc aagttttgaa acatcctgg ccgcctcggc    180 c                                                                     181
```

```
<210> SEQ ID NO 187
<211> LENGTH: 34
<212> TYPE: DNA
<213> ORGANISM: Artificial sequence
<220> FEATURE:
<223> OTHER INFORMATION: Synthetic T1-F

<400> SEQUENCE: 187
ggccattacg gccaaaatgt tcaatcgttt taac                                  34

<210> SEQ ID NO 188
<211> LENGTH: 37
<212> TYPE: DNA
<213> ORGANISM: Artificial sequence
<220> FEATURE:
<223> OTHER INFORMATION: Synthetic T1-R

<400> SEQUENCE: 188
ttgtagtgtt gactggagca ccgagagcgc cgcgaga                               37

<210> SEQ ID NO 189
<211> LENGTH: 35
<212> TYPE: DNA
<213> ORGANISM: Artificial sequence
<220> FEATURE:
<223> OTHER INFORMATION: Synthetic T2-F
```

<400> SEQUENCE: 189
ggccattacg gccaaaatga cgccctatgc agtag                                35

<210> SEQ ID NO 190
<211> LENGTH: 37
<212> TYPE: DNA
<213> ORGANISM: Artificial sequence
<220> FEATURE:
<223> OTHER INFORMATION: Synthetic T2-R

<400> SEQUENCE: 190
ttgtagtgtt gactggagct gcgctcactg ttacaat                              37

<210> SEQ ID NO 191
<211> LENGTH: 34
<212> TYPE: DNA
<213> ORGANISM: Artificial sequence
<220> FEATURE:
<223> OTHER INFORMATION: Synthetic T3-F

<400> SEQUENCE: 191
ggccattacg gccaaaatgc aattcaaaaa cgtc                                 34

<210> SEQ ID NO 192
<211> LENGTH: 37
<212> TYPE: DNA
<213> ORGANISM: Artificial sequence
<220> FEATURE:
<223> OTHER INFORMATION: Synthetic T3-R

<400> SEQUENCE: 192
ttgtagtgtt gactggagca gcagaagcag tggcgga                              37

<210> SEQ ID NO 193
<211> LENGTH: 34
<212> TYPE: DNA
<213> ORGANISM: Artificial sequence
<220> FEATURE:
<223> OTHER INFORMATION: Synthetic T4-F

<400> SEQUENCE: 193
ggccattacg gccaaaatga gatttgcaga attc                                 34

<210> SEQ ID NO 194
<211> LENGTH: 38
<212> TYPE: DNA
<213> ORGANISM: Artificial sequence
<220> FEATURE:
<223> OTHER INFORMATION: Synthetic T4-R

<400> SEQUENCE: 194
ttgtagtgtt gactggagca gccatccccc cgcctaac                             38

<210> SEQ ID NO 195
<211> LENGTH: 18
<212> TYPE: DNA
<213> ORGANISM: Artificial sequence
<220> FEATURE:
<223> OTHER INFORMATION: Synthetic MF-pro-F

<400> SEQUENCE: 195
gctccagtca acactaca                                                   18

<210> SEQ ID NO 196

<211> LENGTH: 36
<212> TYPE: DNA
<213> ORGANISM: Artificial sequence
<220> FEATURE:
<223> OTHER INFORMATION: Synthetic MF-R

<400> SEQUENCE: 196
ggccgaggcg gccgataccc cttcttcttt agcagc       36

<210> SEQ ID NO 197
<211> LENGTH: 34
<212> TYPE: DNA
<213> ORGANISM: Artificial sequence
<220> FEATURE:
<223> OTHER INFORMATION: Synthetic MF-Pre-F

<400> SEQUENCE: 197
ggccattacg gccaaaatgg tatcgaagac ttgg       34

<210> SEQ ID NO 198
<211> LENGTH: 36
<212> TYPE: DNA
<213> ORGANISM: Artificial sequence
<220> FEATURE:
<223> OTHER INFORMATION: Synthetic KR-IGF-F

<400> SEQUENCE: 198
ctcgccttag ataaaagagg accggagacg ctctgc       36

<210> SEQ ID NO 199
<211> LENGTH: 36
<212> TYPE: DNA
<213> ORGANISM: Artificial sequence
<220> FEATURE:
<223> OTHER INFORMATION: Synthetic IGF-R

<400> SEQUENCE: 199
cactccgttc aagtcgactc aagctgactt ggcagg       36

<210> SEQ ID NO 200
<211> LENGTH: 88
<212> TYPE: PRT
<213> ORGANISM: Artificial sequence
<220> FEATURE:
<223> OTHER INFORMATION: Synthetic TFP-5-aa

<400> SEQUENCE: 200

Met Phe Asn Arg Phe Asn Lys Phe Gln Ala Ala Val Ala Leu Ala Leu
1               5                   10                  15

Leu Ser Arg Gly Ala Leu Gly Ala Pro Val Asn Thr Thr Thr Glu Asp
                20                  25                  30

Glu Thr Ala Gln Ile Pro Ala Glu Ala Val Ile Gly Tyr Leu Asp Leu
            35                  40                  45

Glu Gly Asp Phe Asp Val Ala Val Leu Pro Phe Ser Asn Ser Thr Asn
        50                  55                  60

Asn Gly Leu Leu Phe Ile Asn Thr Thr Ile Ala Ser Ile Ala Ala Lys
65                  70                  75                  80

Glu Glu Gly Val Ala Ala Ser Ala
                85

<210> SEQ ID NO 201
<211> LENGTH: 280
<212> TYPE: DNA
<213> ORGANISM: Artificial sequence -continued

```
<220> FEATURE:
<223> OTHER INFORMATION: Synthetic TFP-5-NT

<400> SEQUENCE: 201
ggccattacg gccaaaatgt tcaatcgttt taacaaattc caagctgctg tcgctttggc    60
cctactctct cgcggcgctc tcggtgctcc agtcaacact acaacagaag atgaaacggc   120
acaaattccg gctgaagctg tcatcggtta cttagattta aaggggatt tcgatgttgc    180 tgttttgcca ttttccaaca gcacaaataa cgggttattg tttataaata ctactattgc   240
cagcattgct gctaaagaag aagggtggc cgcctcggcc                          280

<210> SEQ ID NO 202
<211> LENGTH: 84
<212> TYPE: PRT
<213> ORGANISM: Artificial sequence
<220> FEATURE:
<223> OTHER INFORMATION: Synthetic TFP-6-aa

<400> SEQUENCE: 202

Met Thr Pro Tyr Ala Val Ala Ile Thr Val Ala Leu Leu Ile Val Thr
1               5                   10                  15

Val Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ala Ala Ser Ala

<210> SEQ ID NO 203
<211> LENGTH: 268
<212> TYPE: DNA
<213> ORGANISM: Artificial sequence
<220> FEATURE:
<223> OTHER INFORMATION: Synthetic TFP-6-NT

<400> SEQUENCE: 203
ggccattacg gccaaaatga cgccctatgc agtagcaatt accgtggcct tactaattgt    60
aacagtgagc gcagctccag tcaacactac aacagaagat gaaacggcac aaattccggc   120
tgaagctgtc atcggttact tagatttaga aggggatttc gatgttgctg ttttgccatt   180
ttccaacagc acaaataacg gttattgtt tataaatact actattgcca gcattgctgc    240
taaagaagaa ggggtggccg cctcggcc                                      268

<210> SEQ ID NO 204
<211> LENGTH: 86
<212> TYPE: PRT
<213> ORGANISM: Artificial sequence
<220> FEATURE:
<223> OTHER INFORMATION: Synthetic TFP-7-aa

<400> SEQUENCE: 204

Met Gln Phe Lys Asn Val Ala Leu Ala Ala Ser Val Ala Ala Leu Ser
1               5                   10                  15

Ala Thr Ala Ser Ala Ala Pro Val Asn Thr Thr Thr Glu Asp Glu Thr
            20                  25                  30

Ala Gln Ile Pro Ala Glu Ala Val Ile Gly Tyr Leu Asp Leu Glu Gly
```

```
                35                  40                  45
Asp Phe Asp Val Ala Val Leu Pro Phe Ser Asn Ser Thr Asn Asn Gly
         50                  55                  60

Leu Leu Phe Ile Asn Thr Thr Ile Ala Ser Ile Ala Ala Lys Glu Glu
 65                  70                  75                  80

Gly Val Ala Ala Ser Ala
                 85

<210> SEQ ID NO 205
<211> LENGTH: 274
<212> TYPE: DNA
<213> ORGANISM: Artificial sequence
<220> FEATURE:
<223> OTHER INFORMATION: Synthetic TFP-7-NT

<400> SEQUENCE: 205
ggccattacg gccaaaatgc aattcaaaaa cgtcgcccta gctgcctccg ttgctgctct      60
atccgccact gcttctgctg ctccagtcaa cactacaaca gaagatgaaa cggcacaaat    120
tccggctgaa gctgtcatcg gttacttaga tttagaaggg gatttcgatg ttgctgtttt    180 gccatttttcc aacagcacaa ataacgggtt attgtttata aatactacta ttgccagcat    240
tgctgctaaa gaagaagggg tggccgcctc ggcc                                  274

<210> SEQ ID NO 206
<211> LENGTH: 83
<212> TYPE: PRT
<213> ORGANISM: Artificial sequence
<220> FEATURE:
<223> OTHER INFORMATION: Synthetic TFP-8-aa

<400> SEQUENCE: 206

Met Arg Phe Ala Glu Phe Leu Val Val Phe Ala Thr Leu Gly Gly Gly
  1               5                  10                  15

Met Ala Ala Pro Val Asn Thr Thr Thr Glu Asp Glu Thr Ala Gln Ile
             20                  25                  30

Pro Ala Glu Ala Val Ile Gly Tyr Leu Asp Leu Glu Gly Asp Phe Asp
         35                  40                  45

Val Ala Val Leu Ser Phe Ser Asn Ser Thr Asn Asn Gly Leu Leu Phe
     50                  55                  60

Ile Asn Thr Thr Ile Ala Ser Ile Ala Ala Lys Glu Glu Gly Val Ala
 65                  70                  75                  80

Ala Ser Ala

<210> SEQ ID NO 207
<211> LENGTH: 265
<212> TYPE: DNA
<213> ORGANISM: Artificial sequence
<220> FEATURE:
<223> OTHER INFORMATION: Synthetic TFP-8-NT

<400> SEQUENCE: 207
ggccattacg gccaaaatga gatttgcaga attcttggtg gtatttgcca cgttaggcgg      60
ggggatggct gctccagtca acactacaac agaagatgaa acggcacaaa ttccggctga    120
agctgtcatc ggttacttag atttagaagg ggatttcgat gttgctgttt tgtcattttc    180
caacagcaca ataacgggt tattgtttat aaatactact attgccagca ttgctgctaa    240
agaagaaggg gtggccgcct cggcc                                            265
```

<210> SEQ ID NO 208
<211> LENGTH: 84
<212> TYPE: PRT
<213> ORGANISM: Artificial sequence
<220> FEATURE:
<223> OTHER INFORMATION: Synthetic TFP-32-aa

<400> SEQUENCE: 208

```
Met Arg Phe Pro Ser Ile Phe Thr Ala Val Leu Phe Ala Ala Ser Ser
1               5                   10                  15
Ala Leu Ala Ala Pro Val Asn Thr Thr Thr Glu Asp Glu Thr Ala Gln
            20                  25                  30
Ile Pro Ala Glu Ala Val Ile Gly Tyr Leu Asp Leu Glu Gly Asp Phe
        35                  40                  45
Asp Val Ala Val Leu Pro Phe Ser Asn Ser Thr Asn Asn Gly Leu Leu
    50                  55                  60
Phe Ile Asn Thr Thr Ile Ala Ser Ile Ala Ala Lys Glu Glu Gly Val
65                  70                  75                  80
Ala Ala Ser Ala
```

<210> SEQ ID NO 209
<211> LENGTH: 268
<212> TYPE: DNA
<213> ORGANISM: Artificial sequence
<220> FEATURE:
<223> OTHER INFORMATION: Synthetic TFP-32-NT

<400> SEQUENCE: 209

```
ggccattacg gccaaaatga gatttccttc aatttttact gcagtttat tcgcagcatc      60
ctccgcatta gctgctccag tcaacactac aacagaagat gaaacggcac aaattccggc    120
tgaagctgtc atcggttact tagatttaga aggggatttc gatgttgctg ttttgccatt    180
ttccaacagc acaaataacg ggttattgtt tataaatact actattgcca gcattgctgc    240
taaagaagaa ggggtggccg cctcggcc                                       268
```

<210> SEQ ID NO 210
<211> LENGTH: 36
<212> TYPE: DNA
<213> ORGANISM: Artificial sequence
<220> FEATURE:
<223> OTHER INFORMATION: Synthetic KR-hP10-F

<400> SEQUENCE: 210

```
ctcgccttag ataaaagagc tattaagaaa gcccac                               36
```

<210> SEQ ID NO 211
<211> LENGTH: 35
<212> TYPE: DNA
<213> ORGANISM: Artificial sequence
<220> FEATURE:
<223> OTHER INFORMATION: Synthetic hP10-Sal-R

<400> SEQUENCE: 211

```
ctccgttcaa gtcgacttaa tgtcctggga agagg                                35
```

<210> SEQ ID NO 212
<211> LENGTH: 37
<212> TYPE: DNA
<213> ORGANISM: Artificial sequence
<220> FEATURE:
<223> OTHER INFORMATION: Synthetic KR-IL32g-F

<400> SEQUENCE: 212

```
ctcgccttag ataaaagaat gtgcttcccg aaggtcc                                    37
```

<210> SEQ ID NO 213
<211> LENGTH: 36
<212> TYPE: DNA
<213> ORGANISM: Artificial sequence
<220> FEATURE:
<223> OTHER INFORMATION: Synthetic IL32g-SalI-R

<400> SEQUENCE: 213

```
cactccgttc aagtcgactc attttgagga ttgggg                                     36
```

<210> SEQ ID NO 214
<211> LENGTH: 4
<212> TYPE: PRT
<213> ORGANISM: Artificial sequence
<220> FEATURE:
<223> OTHER INFORMATION: Synthetic kex2p protease recognition sequence

<400> SEQUENCE: 214

Leu Asp Lys Arg
1

<210> SEQ ID NO 215
<211> LENGTH: 4
<212> TYPE: PRT
<213> ORGANISM: Artificial sequence
<220> FEATURE:
<223> OTHER INFORMATION: Synthetic Factor Xa recognition sequence

<400> SEQUENCE: 215

Ile Glu Gly Arg
1

<210> SEQ ID NO 216
<211> LENGTH: 4
<212> TYPE: PRT
<213> ORGANISM: Artificial sequence
<220> FEATURE:
<223> OTHER INFORMATION: Synthetic subtilisin recognition sequence

<400> SEQUENCE: 216

Ala Ala His Tyr
1

<210> SEQ ID NO 217
<211> LENGTH: 7
<212> TYPE: PRT
<213> ORGANISM: Artificial sequence
<220> FEATURE:
<223> OTHER INFORMATION: Synthetic tobacco etch virus recognition
      sequence

<400> SEQUENCE: 217

Glu Asn Leu Tyr Phe Gln Gly
1               5

<210> SEQ ID NO 218
<211> LENGTH: 7
<212> TYPE: PRT
<213> ORGANISM: Artificial sequence
<220> FEATURE:
<223> OTHER INFORMATION: Synthetic thrombin recognition sequence

<400> SEQUENCE: 218

Glu Asn Leu Tyr Phe Gln Gly

<210> SEQ ID NO 219
<211> LENGTH: 105
<212> TYPE: PRT
<213> ORGANISM: Artificial sequence
<220> FEATURE:
<223> OTHER INFORMATION: Saccharomyces cerevisiae TFP-1-aa

<400> SEQUENCE: 219

Met Phe Asn Arg Phe Asn Lys Phe Gln Ala Ala Val Ala Leu Ala Leu
1               5                   10                  15

Leu Ser Arg Gly Ala Leu Gly Asp Ser Tyr Thr Asn Ala Thr Ser Ser
            20                  25                  30

Ala Asp Leu Ser Ser Ile Thr Ser Val Ser Ala Ser Ala Ser Ala
        35                  40                  45

Thr Ala Ser Asp Ser Leu Ser Ser Ser Asp Gly Thr Val Tyr Leu Pro
    50                  55                  60

Ser Thr Thr Ile Ser Gly Asp Leu Thr Val Thr Gly Lys Val Ile Ala
65                  70                  75                  80

Thr Glu Ala Val Glu Val Ala Ala Gly Gly Lys Leu Thr Leu Leu Asp
                85                  90                  95

Gly Glu Lys Tyr Val Phe Ser Ser Asp
            100                 105

<210> SEQ ID NO 220
<211> LENGTH: 430
<212> TYPE: DNA
<213> ORGANISM: Artificial sequence
<220> FEATURE:
<223> OTHER INFORMATION: Saccharomyces cerevisiae TFP-1-NT

<400> SEQUENCE: 220
gatcgtcata ttcactcttg ttctcataat agcagtccaa gttttcatct ttgcaagctt      60
tactatttct ttcttttat tggtaaactc tcgcccatta caaaaaaaaa agagatgttc      120
aatcgtttta acaaattcca agctgctgtc gctttggccc tactctctcg cggcgctctc      180
ggtgactctt acaccaatag cacctcctcc gcagacttga gttctatcac ttccgtctcg      240
tcagctagtg caagtgccac cgcttccgac tcactttctt ccagtgacgg taccgtttat      300
ttgccatcca acaattag cggtgatctc acagttactg gtaaagtaat tgcaaccgag       360
gccgtggaag tcgctgccgg tggtaagttg actttacttg acggtgaaaa atacgtcttc      420
tcatctgatc                                                             430

<210> SEQ ID NO 221
<211> LENGTH: 117
<212> TYPE: PRT
<213> ORGANISM: Artificial sequence
<220> FEATURE:
<223> OTHER INFORMATION: Saccharomyces cerevisiae TFP-2-aa

<400> SEQUENCE: 221

Met Thr Pro Tyr Ala Val Ala Ile Thr Val Ala Leu Leu Ile Val Thr
1               5                   10                  15

Val Ser Ala Leu Gln Val Asn Asn Ser Cys Val Ala Phe Pro Pro Ser
            20                  25                  30

Asn Leu Arg Gly Lys Asn Gly Asp Gly Thr Asn Glu Gln Tyr Ala Thr
        35                  40                  45

Ala Leu Leu Ser Ile Pro Trp Asn Gly Pro Pro Glu Ser Leu Arg Asp

```
                50                  55                  60
Ile Asn Leu Ile Glu Leu Glu Pro Gln Val Ala Leu Tyr Leu Leu Glu
 65                  70                  75                  80

Asn Tyr Ile Asn His Tyr Tyr Asn Thr Thr Arg Asp Asn Lys Cys Pro
                 85                  90                  95

Asn Asn His Tyr Leu Met Gly Gly Gln Leu Gly Ser Ser Ser Asp Asn
                100                 105                 110

Arg Ser Leu Asn Asp
        115

<210> SEQ ID NO 222
<211> LENGTH: 424
<212> TYPE: DNA
<213> ORGANISM: Artificial sequence
<220> FEATURE:
<223> OTHER INFORMATION: Saccharomyces cerevisiae TFP-2-NT

<400> SEQUENCE: 222
gatctcattg gattcaagag aaagaaactc tatactggcg ccaaattagc agtgtcaaat     60
ttcgaaaagg tgatgacgcc ctatgcagta gcaattaccg tggccttact aattgtaaca    120
gtgagcgcac tccaggtcac aattcatgtg tcgcttttcc gccaatcaaa tctcagaggc    180
aaaaatggag acggtactaa tgaacagtat gcaactgcac tactttctat tccctggaat    240
ggacctcctg agtcattgag ggatattaat cttattgaac tcgaaccgca agttgcactc    300
tatttgctcg aaaattatat taaccattac tacaacacca caagagacaa taagtgccct    360
aataaccact acctaatggg agggcagttg ggtagctcat cggataatag gagtttgaac    420
gatc                                                                424

<210> SEQ ID NO 223
<211> LENGTH: 104
<212> TYPE: PRT
<213> ORGANISM: Artificial sequence
<220> FEATURE:
<223> OTHER INFORMATION: Saccharomyces cerevisiae TFP-3-aa

<400> SEQUENCE: 223

Met Gln Phe Lys Asn Val Ala Leu Ala Ala Ser Val Ala Ala Leu Ser
 1               5                  10                  15

Ala Thr Ala Ser Ala Glu Gly Tyr Thr Pro Gly Glu Pro Trp Ser Thr
                 20                  25                  30

Leu Thr Pro Thr Gly Ser Ile Ser Cys Gly Ala Ala Glu Tyr Thr Thr
                 35                  40                  45

Thr Phe Gly Ile Ala Val Gln Ala Ile Thr Ser Ser Lys Ala Lys Arg
         50                  55                  60

Asp Val Ile Ser Gln Ile Gly Asp Gly Gln Val Gln Ala Thr Ser Ala
 65                  70                  75                  80

Ala Thr Ala Gln Ala Thr Asp Ser Gln Ala Gln Ala Thr Thr Thr Ala
                 85                  90                  95

Thr Pro Thr Ser Ser Glu Lys Ile
                100

<210> SEQ ID NO 224
<211> LENGTH: 642
<212> TYPE: DNA
<213> ORGANISM: Artificial sequence
<220> FEATURE:
<223> OTHER INFORMATION: Saccharomyces cerevisiae TFP-3-NT
```

-continued

<400> SEQUENCE: 224

```
gatcccgcct agcccttcca gcttttcttt ttccccttttt gctacggtcg agacacggtc    60
gcccaaaaga aacgggtcag cgtgtactgc gccaaaaaaa ttcgcgccga tttaagctaa   120
acgtccacaa acaaaaacaa aaataagaaa taggttgaca gtgggtgaaa aattctcgaa   180
ggtttcatct ccaaacagtc agtatataag tattcgggaa agagagccaa tctatcttgt   240
ggtgggtcta tcttaacctt ctcttttttgg cagtagtaat tgtaaatcaa gacacataaa   300
actatttcac tcgctaaact tacatctaaa atgcaattca aaaacgtcgc cctagctgcc   360
tccgttgctg ctctatccgc cactgcttct gctgaaggtt acactccagg tgaaccatgg   420
tccaccttaa ccccaaccgg ctccatctct tgtggtgctg ccgaatacac taccaccttt   480
ggtattgctg ttcaagctat tacctcttca aaagctaaga gagacgttat ctctcaaatt   540
ggtgacggtc aagtccaagc cacttctgct gctactgctc aagccaccga tagtcaagcc   600
caagctacta ctaccgctac cccaaccagc tccgaaaaga tc                      642
```

<210> SEQ ID NO 225
<211> LENGTH: 50
<212> TYPE: PRT
<213> ORGANISM: Artificial sequence
<220> FEATURE:
<223> OTHER INFORMATION: Saccharomyces cerevisiae TFP-4-aa

<400> SEQUENCE: 225

```
Met Arg Phe Ala Glu Phe Leu Val Val Phe Ala Thr Leu Gly Gly Gly
1               5                  10                  15
Met Ala Ala Pro Val Glu Ser Leu Ala Gly Thr Gln Arg Tyr Leu Val
            20                  25                  30
Gln Met Lys Glu Arg Phe Thr Thr Glu Lys Leu Cys Ala Leu Asp Asp
        35                  40                  45
Lys Ile
    50
```

<210> SEQ ID NO 226
<211> LENGTH: 179
<212> TYPE: DNA
<213> ORGANISM: Artificial sequence
<220> FEATURE:
<223> OTHER INFORMATION: Saccharomyces cerevisiae TFP-4-NT

<400> SEQUENCE: 226

```
gatccgcttt ttattgcttt gctttgctaa tgagatttgc agaattcttg gtggtatttg    60
ccacgttagg cggggggatg gctgcaccgg ttgagtctct ggccgggacc caacggtatc   120
tggtgcaaat gaaggagcgg ttcaccacag agaagctgtg tgctttggac gacaagatc    179
```

<210> SEQ ID NO 227
<211> LENGTH: 35
<212> TYPE: DNA
<213> ORGANISM: Artificial sequence
<220> FEATURE:
<223> OTHER INFORMATION: Synthetic PpTFP1-F

<400> SEQUENCE: 227

```
agtggccatt acggccaaaa tgcaattcaa cagtg                               35
```

<210> SEQ ID NO 228
<211> LENGTH: 39
<212> TYPE: DNA
<213> ORGANISM: Artificial sequence

```
<220> FEATURE:
<223> OTHER INFORMATION: Synthetic PpTFP1-R

<400> SEQUENCE: 228
tagggccgag gcggccagtg tggccgatgg gtcccattg                              39

<210> SEQ ID NO 229
<211> LENGTH: 35
<212> TYPE: DNA
<213> ORGANISM: Artificial sequence
<220> FEATURE:
<223> OTHER INFORMATION: Synthetic PpTFP2-F

<400> SEQUENCE: 229
agtggccatt acggccaaaa tgcaattctc tatcg                                  35

<210> SEQ ID NO 230
<211> LENGTH: 38
<212> TYPE: DNA
<213> ORGANISM: Artificial sequence
<220> FEATURE:
<223> OTHER INFORMATION: Synthetic PpTFP2-R

<400> SEQUENCE: 230
tagggccgag gcggccagtg gggtggagtg ggtggttg                               38

<210> SEQ ID NO 231
<211> LENGTH: 37
<212> TYPE: DNA
<213> ORGANISM: Artificial sequence
<220> FEATURE:
<223> OTHER INFORMATION: Synthetic PpTFP3-F

<400> SEQUENCE: 231
agtggccatt acggccaaaa tgaagttttc cactgcg                                37

<210> SEQ ID NO 232
<211> LENGTH: 38
<212> TYPE: DNA
<213> ORGANISM: Artificial sequence
<220> FEATURE:
<223> OTHER INFORMATION: Synthetic PpTFP3-R

<400> SEQUENCE: 232
tagggccgag gcggccaggg tagtggtagg atctggag                               38

<210> SEQ ID NO 233
<211> LENGTH: 35
<212> TYPE: DNA
<213> ORGANISM: Artificial sequence
<220> FEATURE:
<223> OTHER INFORMATION: Synthetic PpTFP4-F

<400> SEQUENCE: 233
agtggccatt acggccaaaa tgcaatacag atctc                                  35
```